(12) United States Patent
Komiya et al.

(10) Patent No.: US 7,756,327 B2
(45) Date of Patent: Jul. 13, 2010

(54) IMAGE PROCESSING SYSTEM HAVING MULTIPLE IMAGING MODES

(75) Inventors: Yasuhiro Komiya, Hino (JP); Toru Wada, Niiza (JP); Osamu Konno, Iruma (JP); Takeyuki Ajito, Hachioji (JP); Tomoyuki Nakamura, Hino (JP)

(73) Assignee: Olympus Corporation, Tokyo (JP)

( * ) Notice: Subject to any disclaimer, the term of this patent is extended or adjusted under 35 U.S.C. 154(b) by 618 days.

(21) Appl. No.: 10/521,779

(22) PCT Filed: Jul. 24, 2003

(86) PCT No.: PCT/JP03/09381

§ 371 (c)(1),
(2), (4) Date: Jan. 21, 2005

(87) PCT Pub. No.: WO2004/036162

PCT Pub. Date: Apr. 29, 2004

(65) Prior Publication Data

US 2006/0152586 A1 Jul. 13, 2006

(30) Foreign Application Priority Data

Jul. 26, 2002 (JP) ............................. 2002-218864

(51) Int. Cl.
 G06K 9/00 (2006.01)
 H04N 5/225 (2006.01)
 H04N 9/04 (2006.01)
 H04N 9/07 (2006.01)
 G03B 29/00 (2006.01)
 G03B 41/00 (2006.01)

(52) U.S. Cl. ..................... 382/162; 382/154; 382/128; 348/207.99; 348/207.1; 348/266; 396/14; 396/16

(58) Field of Classification Search ................... 396/14, 396/16; 348/207.99, 207.1, 207.11, 266, 348/222.1; 382/100, 128, 154, 162
See application file for complete search history.

(56) References Cited

U.S. PATENT DOCUMENTS 4,011,571 A 3/1977 Okuzawa (Continued)

FOREIGN PATENT DOCUMENTS

DE 199 62 779 A1 6/2001

(Continued)

OTHER PUBLICATIONS

Occupational Health Services-Dictionary Page; www.occupational-health-services.co.uk/dictionary.html, pp. 1 of 7.*

(Continued)

Primary Examiner—Bhavesh M Mehta
Assistant Examiner—Mia M Thomas
(74) Attorney, Agent, or Firm—Frishauf, Holtz, Goodman & Chick, P.C.

(57) ABSTRACT

An image processing system is used for dentistry. Upon creating a false tooth of a patient (59), a plurality of illuminating light of LEDs with different wavelengths emit light and a photographing apparatus (1A) photographs a tooth portion of the patient (59), thereby obtaining image data. The image data is sent to a dentistry filing system (2A) serving as a processing apparatus, and color reproducing data is obtained by calculation. The color reproducing data is sent to a dentistry factory (55) via a public line. Data is searched from a database (56) for calculating a ceramic compounding ratio, compound data of the ceramic false tooth is obtained, matching the color of the tooth portion of the patient (59), and the false tooth approximate to the tooth color of the patient (59) is created.

20 Claims, 53 Drawing Sheets

U.S. PATENT DOCUMENTS

| | | | |
|---|---|---|---|
| 4,300,823 A | 11/1981 | Yamanaka et al. | |
| 4,845,553 A | 7/1989 | Konomura et al. | |
| 4,959,679 A | 9/1990 | Yamamoto et al. | |
| 5,051,823 A * | 9/1991 | Cooper et al. | 348/66 |
| 5,381,207 A | 1/1995 | Kazumi | |
| 5,408,268 A | 4/1995 | Shipp | |
| 5,503,559 A * | 4/1996 | Vari | 433/224 |
| 5,523,786 A | 6/1996 | Parulski | |
| 5,654,756 A | 8/1997 | Takahashi et al. | |
| 5,690,486 A * | 11/1997 | Zigelbaum | 433/29 |
| 5,766,006 A * | 6/1998 | Murljacic | 433/26 |
| 5,995,763 A | 11/1999 | Posa et al. | |
| 6,006,041 A | 12/1999 | Mizumaki et al. | |
| 6,038,024 A * | 3/2000 | Berner | 356/326 |
| 6,055,325 A | 4/2000 | Garini et al. | |
| 6,111,650 A * | 8/2000 | Rawicz et al. | 356/402 |
| 6,144,805 A * | 11/2000 | Ogino | 396/81 |
| 6,201,880 B1 * | 3/2001 | Elbaum et al. | 382/100 |
| 6,276,933 B1 * | 8/2001 | Melnyk et al. | 433/26 |
| 6,306,421 B1 * | 10/2001 | Kunz et al. | 424/423 |
| 6,341,957 B1 * | 1/2002 | Momot et al. | 433/215 |
| 6,359,680 B1 | 3/2002 | Rubbert | |
| 6,396,873 B1 | 5/2002 | Goldstein et al. | |
| 6,413,207 B1 * | 7/2002 | Minami | 600/109 |
| 6,431,870 B1 | 8/2002 | Sachdeva | |
| 6,454,437 B1 | 9/2002 | Kelly | |
| 6,600,832 B1 * | 7/2003 | Nakayama et al. | 382/162 |
| 6,672,868 B1 * | 1/2004 | Momot et al. | 433/29 |
| 6,714,657 B1 * | 3/2004 | Jacobs et al. | 382/100 |
| 6,721,009 B1 | 4/2004 | Iizuka | |
| 6,749,310 B2 | 6/2004 | Pohlert et al. | |
| 6,776,614 B2 | 8/2004 | Wiechmann et al. | |
| 6,807,297 B1 | 10/2004 | Tankovich et al. | |
| 6,856,354 B1 * | 2/2005 | Ohsawa | 348/370 |
| 6,940,545 B1 | 9/2005 | Ray et al. | |
| 6,954,227 B2 * | 10/2005 | Yoda | 348/222.1 |
| 6,967,644 B1 | 11/2005 | Kobayashi | |
| 7,033,172 B2 * | 4/2006 | Hansen et al. | 433/29 |
| 7,058,213 B2 * | 6/2006 | Rubbert et al. | 382/128 |
| 7,097,450 B2 * | 8/2006 | Jung et al. | 433/26 |
| 7,106,511 B2 * | 9/2006 | Grot et al. | 359/566 |
| 7,106,958 B2 * | 9/2006 | Kerschbaumer et al. | 396/16 |
| 7,118,374 B2 * | 10/2006 | Culp | 433/26 |
| 7,133,154 B2 * | 11/2006 | Sugiyama | 358/1.9 |
| 7,136,093 B1 * | 11/2006 | Itoh et al. | 348/207.11 |
| 7,144,248 B2 * | 12/2006 | Irwin | 433/29 |
| 7,215,803 B2 * | 5/2007 | Marshall | 382/128 |
| 7,255,558 B2 * | 8/2007 | Babayoff et al. | 433/29 |
| 7,342,668 B2 | 3/2008 | Quadling et al. | |
| 7,355,721 B2 | 4/2008 | Quadling et al. | |
| 7,393,209 B2 * | 7/2008 | Lehmann | 433/26 |
| 7,538,878 B2 * | 5/2009 | Jung et al. | 356/419 |
| 7,576,845 B2 | 8/2009 | Asakura et al. | |
| 2002/0015933 A1 * | 2/2002 | Berner et al. | 433/26 |
| 2002/0054208 A1 | 5/2002 | Goldstein et al. | |
| 2002/0071124 A1 | 6/2002 | Schwarz | |
| 2002/0080276 A1 | 6/2002 | Mori et al. | |
| 2002/0099295 A1 | 7/2002 | Gil et al. | |
| 2002/0102009 A1 * | 8/2002 | Jones et al. | 382/100 |
| 2002/0114505 A1 | 8/2002 | Mahon et al. | |
| 2002/0168784 A1 | 11/2002 | Sundrehagen et al. | |
| 2002/0177751 A1 * | 11/2002 | Ueno et al. | 600/160 |
| 2002/0191102 A1 * | 12/2002 | Yuyama et al. | 348/370 |
| 2003/0011767 A1 | 1/2003 | Imura et al. | |
| 2003/0107652 A1 * | 6/2003 | Williams | 348/207.99 |
| 2003/0206279 A1 | 11/2003 | Kimura et al. | |
| 2004/0076921 A1 * | 4/2004 | Gofman et al. | 433/29 |
| 2004/0125996 A1 | 7/2004 | Eddowes et al. | |
| 2005/0026703 A1 | 2/2005 | Fukawa | |
| 2005/0084144 A1 | 4/2005 | Feldman | |
| 2005/0231592 A1 | 10/2005 | Cable et al. | |
| 2005/0254704 A1 * | 11/2005 | Komiya et al. | 382/162 |
| 2005/0256383 A1 * | 11/2005 | Gandjbakhche et al. | 600/315 |
| 2006/0251408 A1 * | 11/2006 | Konno et al. | 396/14 |
| 2006/0280360 A1 | 12/2006 | Holub | |
| 2007/0064119 A1 * | 3/2007 | Komiya et al. | 348/222.1 |
| 2008/0192235 A1 | 8/2008 | Komiya et al. | |
| 2008/0259336 A1 | 10/2008 | Konno | |
| 2008/0284902 A1 | 11/2008 | Konno et al. | |
| 2008/0292295 A1 | 11/2008 | Konno et al. | |
| 2009/0067695 A1 | 3/2009 | Komiya et al. | |
| 2009/0102964 A1 | 4/2009 | Yuyama et al. | |

FOREIGN PATENT DOCUMENTS

| | | |
|---|---|---|
| EP | 1 072 884 A2 | 1/2001 |
| JP | 03-090123 A | 4/1991 |
| JP | 03-090128 A | 4/1991 |
| JP | 7-120324 A | 5/1995 |
| JP | 7-322103 A | 12/1995 |
| JP | 08-065690 A | 3/1996 |
| JP | 08-079770 A | 3/1996 |
| JP | 8-149352 A | 6/1996 |
| JP | 09-172649 A | 6/1997 |
| JP | 9-178564 A | 7/1997 |
| JP | 10-042302 A | 2/1998 |
| JP | 10-051796 A | 2/1998 |
| JP | 11-055444 A | 2/1999 |
| JP | 11-104061 A | 4/1999 |
| JP | 11-146265 A | 5/1999 |
| JP | 11-196301 A | 7/1999 |
| JP | 11-225953 A | 8/1999 |
| JP | 11-331493 A | 11/1999 |
| JP | 2000-152264 A | 5/2000 |
| JP | 2000-152269 A | 5/2000 |
| JP | 2000-296114 A | 10/2000 |
| JP | 2000-338950 A | 12/2000 |
| JP | 2000-341499 A | 12/2000 |
| JP | 2000-341681 A | 12/2000 |
| JP | 2001-024971 A | 1/2001 |
| JP | 2002-009879 A | 1/2002 |
| JP | 2002-112960 A | 4/2002 |
| JP | 2002-158948 A | 5/2002 |
| JP | 2002-232769 A | 8/2002 |
| JP | 2003-021859 A | 1/2003 |
| JP | 2003-023643 A | 1/2003 |
| JP | 2003-087806 A | 3/2003 |
| JP | 2003-189068 A | 7/2003 |
| JP | 2003-309856 A | 10/2003 |
| JP | 2003-333608 A | 11/2003 |
| WO | WO 01/29542 A1 | 4/2001 |
| WO | WO 01/55956 A1 | 8/2001 |
| WO | WO0155956 * | 8/2001 |
| WO | WO 02/12847 A1 | 2/2002 |
| WO | WO 02/21847 A1 * | 2/2002 |
| WO | WO 2004/012461 A1 | 7/2003 |
| WO | WO 2004/036162 A1 | 4/2004 |

OTHER PUBLICATIONS

Related U.S. Appl. No. 10/521,778, filed Jan. 21, 2005; Inventor: Komiya et al.

Japanese Office Action dated Apr. 1, 2008 issued in a counterpart Japanese Application of related co-pending U.S. Appl. No. 10/521,778.

English language Translation of Japanese Office Action dated Apr. 1, 2008, issued in a counterpart Japanese Application.

Korean Office Action issued in Korean Application No. 10-2005-7001462 (which corresponds to the present application) and partial English translation thereof.

Korean Office Action Issued in Korean Application No. 10-2006-7021448 (which is a Divisional of the Korean application which corresponds to the present application) and partial English translation thereof.

A Japanese Language Office Action dated Apr. 30, 2008, issued in a counterpart Japanese Application.
English language translation of Japanese Office Action dated Apr. 30, 2008, issued in a counterpart Japanese Application.
English language Translation of Japanese Office Action dated Apr. 1, 2008, issued in a counterpart Japanese Application No. 2004-544728.
Chinese Office Action mailed May 9, 2008 issued in counterpart Chinese Appln. No. 038179350.
Related U.S. Appl. No. 12/141,778, filed Jun. 18, 2008.
Related U.S. Appl. No. 12/141,812, filed Jun. 18, 2008.
Divisional U.S. Appl. No. 12/062,399, filed Apr. 3, 2008.
Divisional U.S. Appl. No. 12/264,056, filed Nov. 3, 2008.
Related U.S. Appl. No. 11/486,455, filed Jul. 13, 2006.
Related U.S. Appl. No. 12/141,839, filed Jun. 18, 2008.

Japanese Office Action dated Sep. 29, 2009 and English translation thereof issued in Japanese Application No. 2007-268275, which is a counterpart of related U.S. Appl. No. 11/486,455.
Karremann, R., "Farbmessung and Farbregelung in der Papierproduktion", Technisches Messen TM, R. Oldenbourg Verlag. Munchen, DE, vol. 59, No. 5, May 1, 1992, pp. 209-213.
Supplementary European Search Report dated Nov. 5, 2009 (6 pages), issued in European Application Serial No. 03808856.3, which is a counterpart of related U.S. Appl. No. 12/062,399.
Japanese Office Action dated Dec. 22, 2009 and English translation thereof issued in a counterpart Japanese Application No. 2007-268275, which is a counterpart of related U.S. Appl. No. 11/486,455.

* cited by examiner

FIG.2
(A) 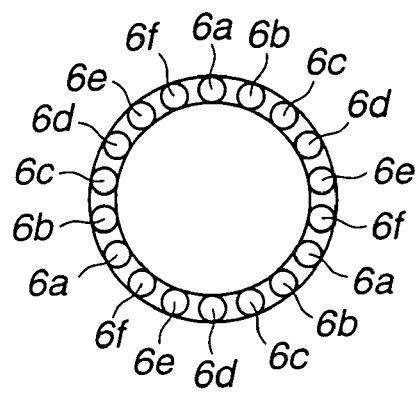
(B) 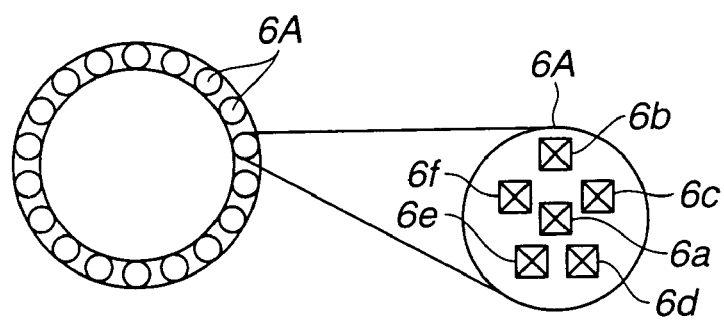
(C) 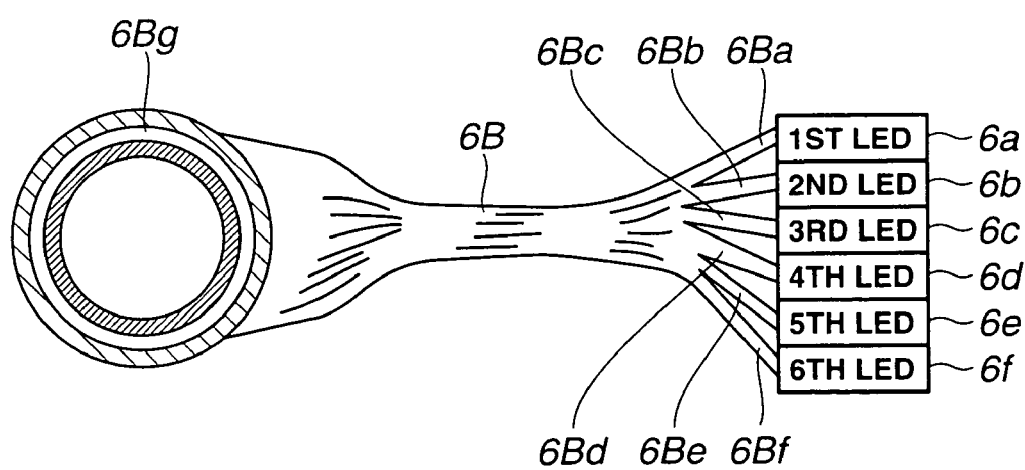

FIG.10

LIGHT-EMITTING MODE (EXAMPLE)

| LED No. | PRIMARY COLOR No. | 1 LIGHT-ON ALL LEDS | 2 LIGHT-ON ONE LED | 3 LIGHT-ON ONE PRIMARY-COLOR LED | 4 LIGHT-ON LEDS GROUP | 5 LIGHT-ON B-LEDS GROUP | 6 LIGHT-ON G-LEDS GROUP | 7 LIGHT-ON R-LEDS GROUP | 8 LIGHT-ON ONE B-LEDS | 9 LIGHT-ON ONE G-LEDS | 10 LIGHT-ON ONE R-LEDS |
|---|---|---|---|---|---|---|---|---|---|---|---|
| 1 | 1 | O | O (EXAMPLE) | O | O | O | | | | | |
| 2 | 2 | O | | (EXAMPLE) | O | O | | | | | |
| 3 | 3 | O | | | O | | O | | | | |
| 4 | 4 | O | | | O | | O | | | | |
| 5 | 5 | O | | | O | | | O | | | |
| 6 | 6 | O | | | O | | | O | | | |
| 7 | 1 | O | | O | (EXAMPLE) | O | | | | | |
| 8 | 2 | O | | | | O | | | | | |
| 9 | 3 | O | | | | | O | | | | |
| 10 | 4 | O | | | | | O | | | | |
| 11 | 5 | O | | | | | | O | | | |
| 12 | 6 | O | | | | | | O | | | |
| 13 | 1 | O | | O | | | | | O | | |
| 14 | 2 | O | | | | | | | O | | |
| 15 | 3 | O | | | | | | | | O | |
| 16 | 4 | O | | | | | | | | O | |
| 17 | 5 | O | | | | | | | | | O |
| 18 | 6 | O | | | | | | | | | O |

FIG.18
(A)
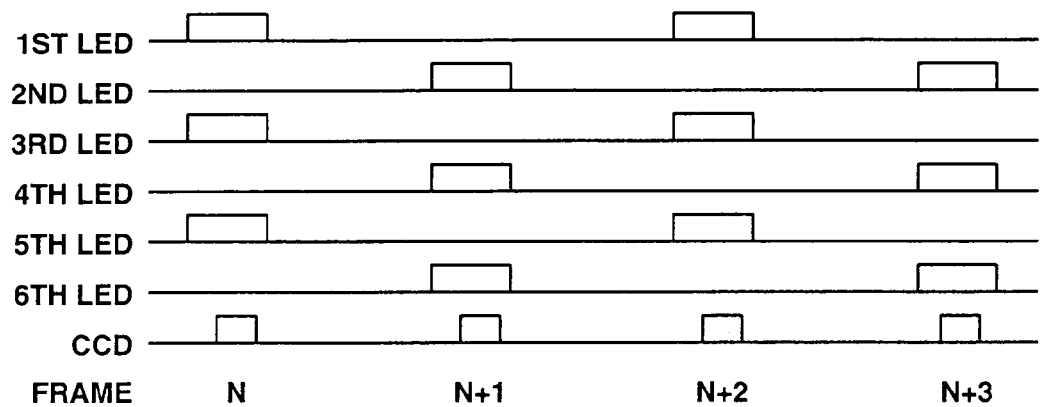
(B)
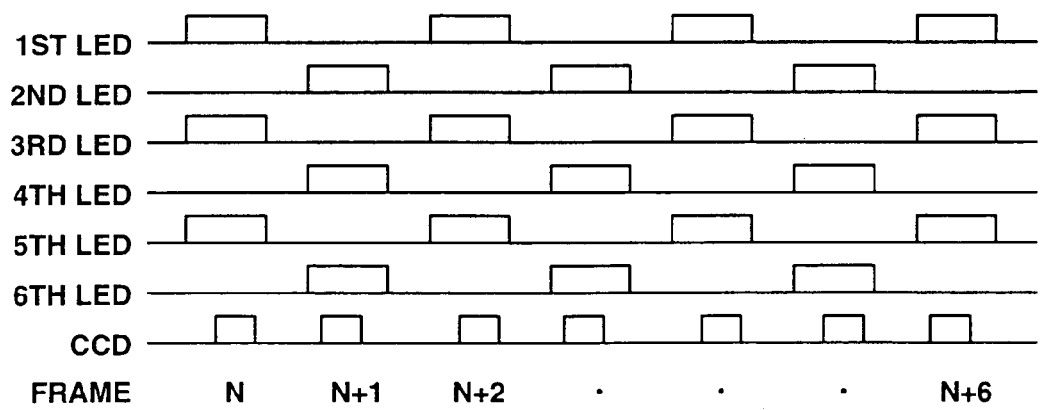

FIG.23
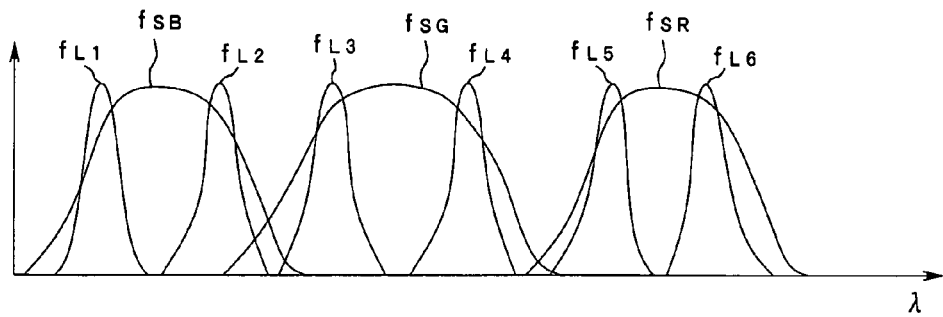
FIG.24
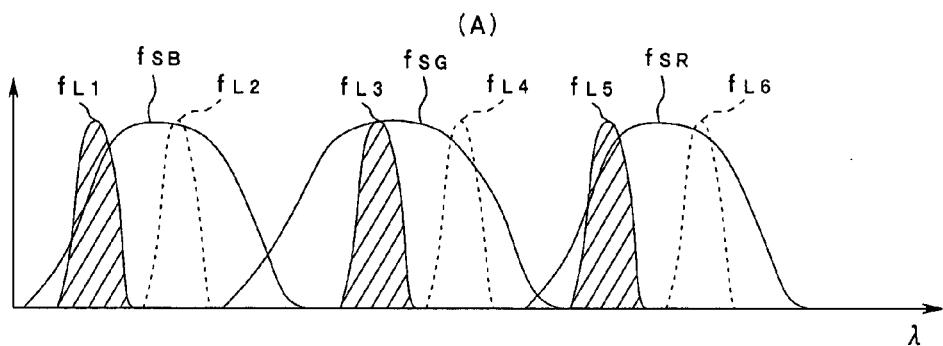
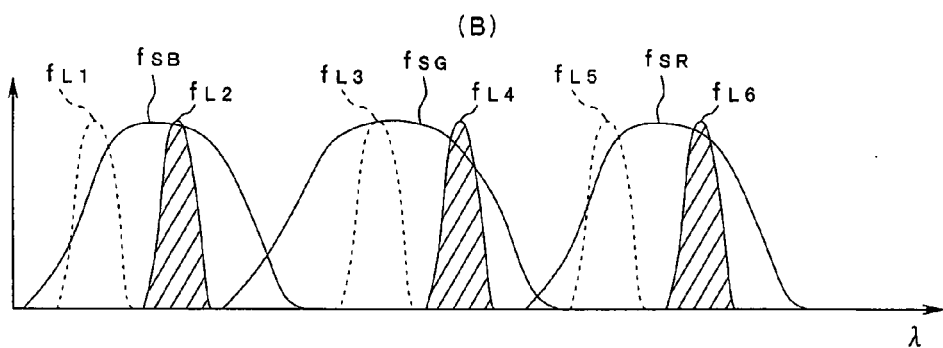
FIG.25
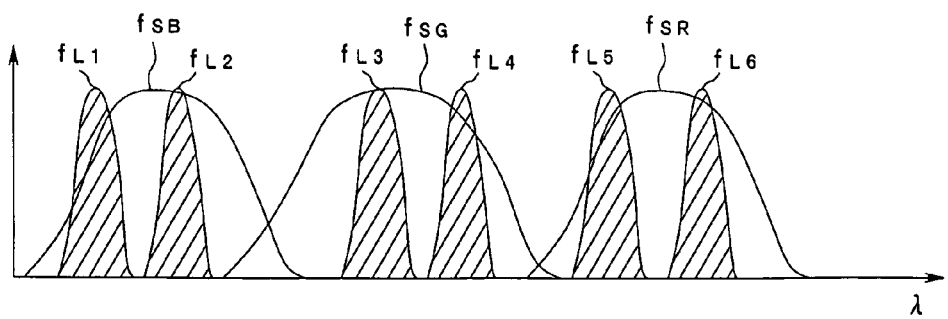

FIG.31
(A)
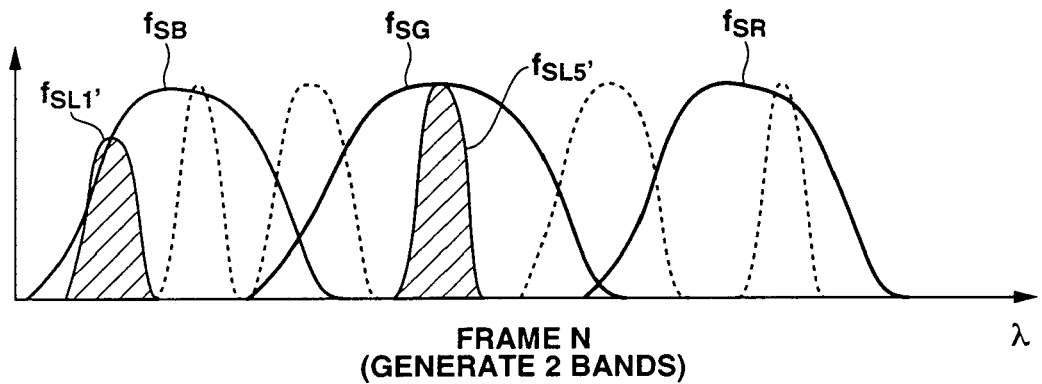
FRAME N
(GENERATE 2 BANDS)
(B)
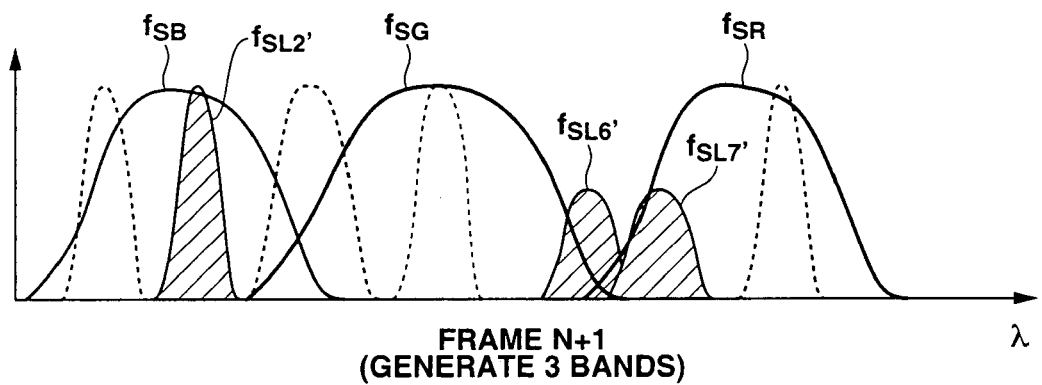
FRAME N+1
(GENERATE 3 BANDS)
(C)
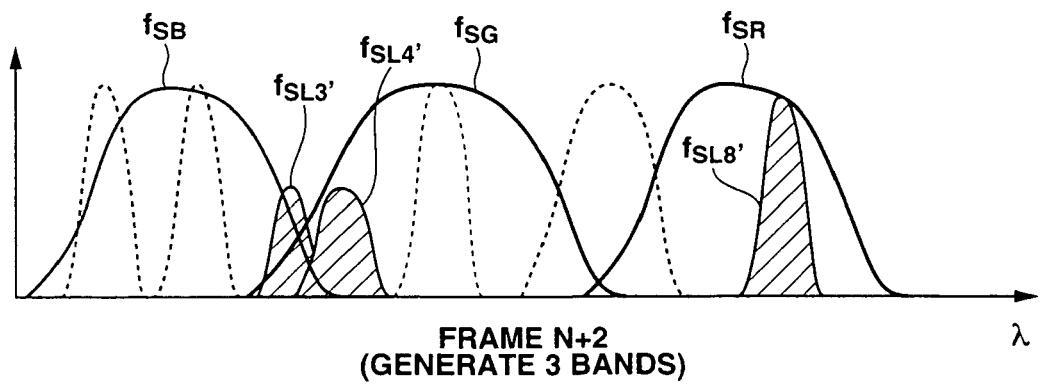
FRAME N+2
(GENERATE 3 BANDS)

FIG.58
(A)
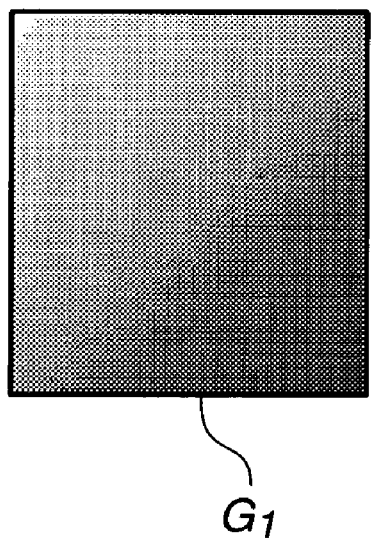
$G_1$
(B)
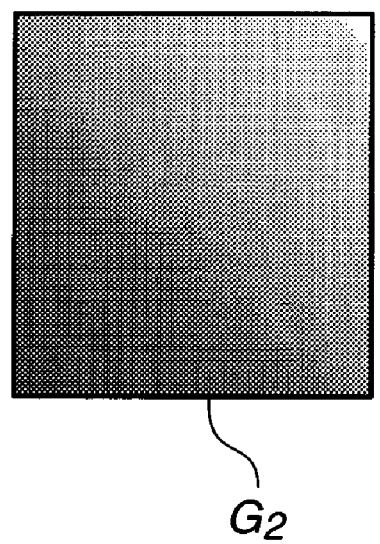
$G_2$

FIG.59
(A)
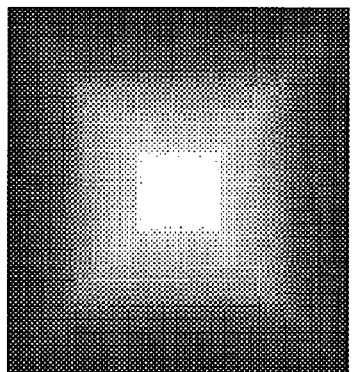
$G_3$
(B)
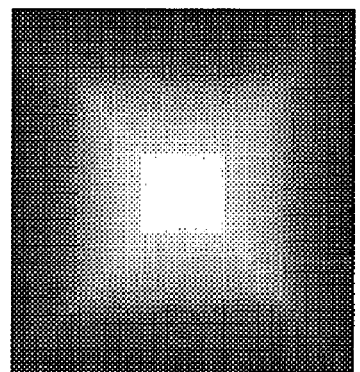
$G_4$

IMAGE PROCESSING SYSTEM HAVING MULTIPLE IMAGING MODES

This application is a U.S. National Phase Application under 35 USC 371 of International Application PCT/JP03/09381 filed Jul. 24, 2003.

TECHNICAL FIELD

The present invention relates to an image processing system, and more particularly, to an image processing system which captures spectroscopic spectrum image information of a subject, and reproduces the color of the subject image from the captured image at high fidelity level, performs inspection or determines the subject image.

BACKGROUND ART

Recently, the increase in concern over the beautification and health is confirmed. For the purpose of beautification, the demand for whitening is increased. Conventionally, a camera system for skin check is used for diagnosis in the dermatology, esthetic salon, beauty counseling, and the like. In the dermatology among them, the peculiarity of the skin surface is checked as the diagnosis thereof based on an image of the crista cutis or sulcus cutis and then the counseling is performed. Japanese Unexamined Patent Application Publication No. 8-149352 and Japanese Unexamined Patent Application Publication No. 7-322103 disclose cameras for skin check.

In the conventional artificial dentition in the dental care, the color grade is determined by comparing the color of a false tooth with the tooth color of a patient by the shading guide to determine the color of the false tooth.

The above-mentioned dermatology and the dentistry require the accurate color reproduction. In one conventional color reproducing system at high fidelity level disclosed in Japanese Unexamined Patent Application Publication No. 2000-152269, a camera is used to photograph an image of a subject under multi-spectrums of exterior lighting. The above-mentioned color reproducing system captures multi-band data and reproduces the color at high fidelity level by the rotation of many rotatable spectroscopic filters to accurately estimate a subject spectroscopic spectrum.

In addition to the dermatology and the dentistry, the paint color of a vehicle and a building, the spectroscopic characteristics of food, and the dyeing of cloths require a technology for reproducing the color of the subject with accuracy for the using purpose of the diagnosis, examination, confirmation, and determination. Further, the examining operability, small size, light weight, and handy size are required for the above devices.

However, the cameras for skin check disclosed in Japanese Unexamined Patent Application Publication No. 8-149352 and Japanese Unexamined Patent Application Publication No. 7-322103 are handy, however, do not reproduce the color at high fidelity level. Further, in the color reproducing system at high fidelity level using a rotatably filter disclosed in Japanese Unexamined Patent Application Publication No. 2000-152269, the weight is heavy because the system is fixedly arranged and another illumination sensor is necessary for the color reproduction because of the exterior lighting.

In the conventional dentistry, the tooth color is selected by the comparison using the shading guide indicating the color shading as mentioned above. This determination is subjective and is influenced by the deterioration and change in room light, thereby causing an error.

SUMMARY OF THE INVENTION

According to one aspect of the invention, an image processing system comprises: an image capturing unit, and an image processing unit. The image capturing unit comprises: an illuminating light source including a plurality of light-emitting devices which respectively emit illumination lights having a plurality of different characteristics of spectroscopic distributions; an image pick-up optical system which forms an image of a subject illuminated by the illuminating light source; an image pick-up device which picks up the subject image formed by the image pick-up optical system and obtains a subject signal; and a control unit which controls light emission by the plurality of light-emitting devices and image pick-up by the image pick-up device and which switches between a spectroscopic image capturing mode which obtains a still image of a subject spectroscopic image and a moving image capturing mode which obtains a moving image thereof. In the spectroscopic image capturing mode, the control unit controls the plurality of light-emitting devices to sequentially emit light according to the characteristics of spectroscopic distributions by a plurality of times interlocking the light emission with an exposure timing of the image pick-up device thereby causing the image pick-up device to obtain a plurality of subject spectroscopic images. In the moving image capturing mode, the control unit is arranged to (i) cause light emission of a light-emitting device for a single specific primary color or cause light emission of light-emitting devices for a plurality of specific primary colors selected from the plurality of light-emitting devices, (ii) cause simultaneous light emission of all of the plurality of light-emitting devices, or (iii) cause sequential light emission of a group of R devices, a group of S devices, and a group of B devices selected from the plurality of light-emitting devices, group by group, and to cause the image pick-up device to obtain a moving image. The image processing unit comprises an image identification calculating unit (also referred to as an image determining and calculating unit herein) which calculates grade data to be used to determine a grade of a color of the subject based on one or more of the subject spectroscopic images captured in the spectroscopic image capturing mode from among the images captured by the image capturing unit.

According to a second invention, in the first invention, the image processing unit further calculates, classifies, or analyzes a predetermined class of the subject based on the image signal stored in the image memory unit.

According to a third invention, in the first invention, the image capturing unit further comprises an illuminating detecting sensor which senses characteristics of spectroscopic distributions of ambient light, an external strobe light-emitting device is attachable to the image capturing unit, a sensing unit of the illuminating detecting sensor is optically connected to a light guide path of strobe light upon the external strobe light-emitting device is attached to the image capturing unit.

According to a fourth invention, in the first invention, the image capturing unit further comprises reflected light rejecting means which prevents the illuminating light source from being photographed directly into the subject.

According to a fifth invention, in the first invention, the image capturing unit further comprises an optical member which reduces the illuminating unhomogeneity between the illuminating light source and the subject.

According to a sixth invention, in the first invention, the image capturing unit further comprises a connecting contact portion for interlocking with an external illuminating device, and the external illuminating device connected via the connecting contact portion is lit-on in the light-on sequence similar to that of the illuminating light sources.

According to a seventh invention, in the first invention, the plurality of illuminating light sources comprise at least one of a light source with the center wavelength of 780 to 900 nm or a light source with the center wavelength of 300 to 380 nm.

According to an eighth invention, in the first invention, the image capturing unit and the image processing unit are integrally formed.

According to a ninth invention, in the first invention, the image capturing unit includes a color chip for calibration in the image processing unit.

According to a tenth invention, in the first invention, the image capturing unit uses a portable terminal device having a photographing function, and an illuminating light source unit having a plurality of illuminating light sources as one unit having different characteristics of spectroscopic distributions is attachable to the portable terminal device having the photographing function.

According to an eleventh invention, in the first invention, the image processing unit comprises image filing software, and image data photographed upon operating the photographing operating unit is recorded to a predetermined portion of the image filing software.

According to a twelfth invention, in the first invention, the image capturing unit further comprises subject portion sensing means which obtains positional information of the subject.

According to a thirteenth invention, in the first invention, the image capturing unit further comprises a temperature measuring unit.

According to a fourteenth invention, in the first invention, the image capturing unit further comprises a pulse rate measuring unit.

According to a fifteenth invention, in the first invention, the image capturing unit further comprises an auscultation function.

According to a sixteenth invention, in the first invention, the image capturing unit further comprises distance measuring means which manages the size of the subject in the photographed image.

BRIEF DESCRIPTION OF THE DRAWINGS

FIG. 2 is a diagram showing an example of the arrangement and an example configuration of LEDs according to the first embodiment;

FIG. 10 is a diagram showing an example for a lighting-on method when three LEDs are arranged for each of six primary colors according to the first embodiment;

FIG. 18 is a timing chart showing reading states in a full mode and a reading double-speed mode according to the second embodiment;

FIG. 23 is a graph showing the light-emitting spectrums of the LEDs and the spectroscopic sensitivity characteristics of a CCD passing through a color filter array according to the third embodiment;

FIG. 24 is a graph showing the spectroscopic characteristics of spectroscopic images of the frames upon creating 6-band spectroscopic images according to the third embodiment;

FIG. 25 is a graph showing the spectroscopic characteristics of the spectroscopic images of the frames upon creating a monitoring image according to the third embodiment;

FIG. 31 is a graph showing the spectroscopic characteristics of the spectroscopic images of frames, upon creating the 8-band spectroscopic images according to the third embodiment;

FIG. 50(A) is a diagram showing the arrangement of the regular-reflection subject, the LEDs of colors, a CCD in the image forming operation, and FIG. 50(B) is a diagram showing an image having a regular-reflection portion.

FIG. 58 is a diagram showing shading states of an LED light source before correction by a photographing apparatus in the image processing system shown in FIG. 57, wherein FIGS. 58(A) and 58(B) are diagrams showing the shading state of different LEDs.

FIG. 59 a diagram showing shading states of the LED light source after correction by the photographing apparatus in the image processing system shown in FIG. 57, wherein FIGS. 59(A) and 59(B) are diagrams showing the shading states of the LEDs.

BEST MODE FOR CARRYING OUT THE INVENTION

Hereinbelow, a description is given of embodiments of the present invention with reference to the drawings.

Figure 1:
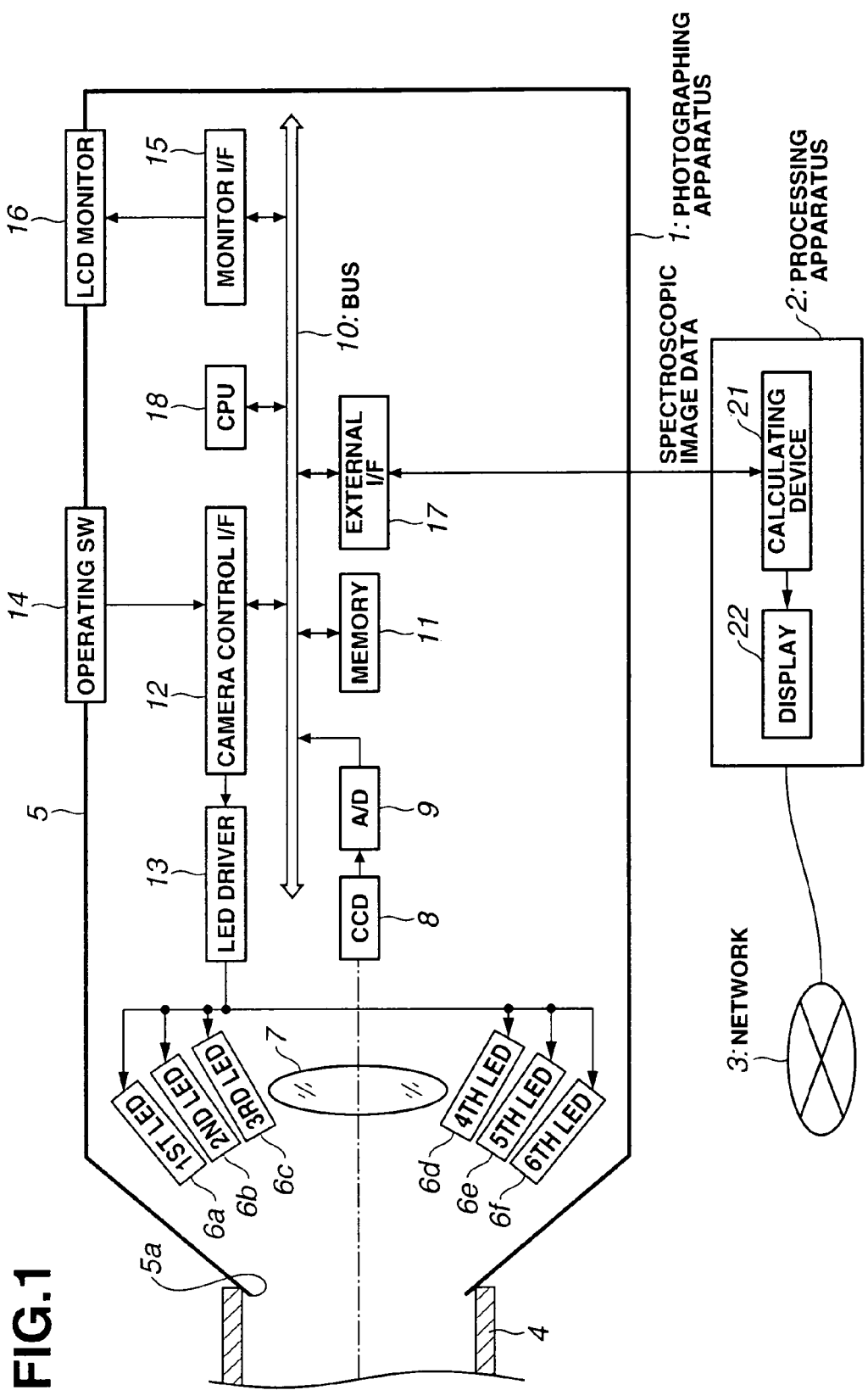
FIG. 1 is a block diagram showing the configuration of an image processing system according to a first embodiment of the present invention.

FIGS. 1 to 16 relate to a first embodiment, FIG. 1 is a block diagram showing the configuration of an image processing system.

The image processing system comprises: a photographing apparatus 1 which can take a picture of a subject spectroscopic image by illuminating a subject with illuminating light having a plurality of independent varying wavelength bands in a visible light area; and a processing apparatus 2 which is connected to the photographing apparatus 1 and processes the subject spectroscopic image outputted from the photographing apparatus 1. The processing apparatus 2 is connected to a network 3 if necessary.

In the photographing apparatus 1 according to the first embodiment, the image pick-up operation of a still image and the image pick-up operation of a moving image are performed. That is, in the image pick-up operation of the still image, illuminating light having six types of wavelength bands (six primary-color illuminating light) is sequentially irradiated to the subject, and six subject-spectroscopic-images are captured as the still images. In the image pick-up operation of the moving image, at least one piece of illuminating light is selected from the six primary-color illuminating light, three R-, G-, and B-illuminating light is set and is sequentially irradiated, and the images are captured as a surface-sequential moving image.

Further, the photographing apparatus 1 comprises: a casing 5 having a projecting port 5a which projects the illuminating light, as will be described later, and on which reflecting light from the subject is incident; an abutting portion 4 which is detachably attached to the projecting port 5a of the casing 5 and is cylindrically-shaped, containing a material with the flexibility for shielding so as to prevent the mixing the ambient light and the illuminating light projected to the subject via the projecting port 5a; first to sixth LEDs 6a to 6f serving as light-emitting devices which are built-in the casing 5 and emit the illuminating light by the light-on so as to illuminate the subject; an image pick-up optical system 7 which is built-in the casing 5 and creates a subject image illuminated by the first to sixth LEDs 6a to 6f; a CCD 8 serving as an image pick-up device, included in an image pick-up device unit which picks-up the subject image formed by the image pick-up optical system 7 and outputs an image signal; an A/D converter 9 which converts an analog signal outputted from the CCD 8 into a digital signal; a memory 11 which temporarily stores the subject spectroscopic image outputted from the A/D converter 9 and transmitted via a bus 10, as will be described later, and which is used as a working area of a CPU 18 as will be described later; an operating switch 14 serving as a photographing operating unit, including various operating switches and operating buttons for inputting a starting instruction of the spectroscopic image photographing operation and inputting a starting or ending instruction of the moving image photographing operation; a camera control I/F 12 which transmits the instructing input from the operating switch 14 to the CPU 18, as will be described later, issues a command for the control of light emission of the first to sixth LEDs 6a to 6f based on the instruction from the CPU 18, and controls the image pick-up operation of the photographing apparatus 1; an LED driver 13 which controls the light emission of a light-emission starting timing and a light-emission ending timing of the first to sixth LEDs 6a to 6f based on the instruction from the camera control I/F 12; a monitor I/F 15 which controls the operation for displaying, on an LCD monitor 16 which will be described later, the subject spectroscopic images (still images) stored in the memory 11 or the moving image picked-up by the CCD 8; the LCD monitor 16 which displays the image outputted form the monitor I/F 15; an external I/F 17 which outputs, to the processing apparatus 2, the subject spectroscopic images stored in the memory 11 and control data from the processing apparatus 2 or inputs communication data from the processing apparatus 2; and the CPU 18 serving as a control unit which systematically controls the photographing apparatus 1 including the A/D converter 9, the memory 11, the camera control I/F 12, the monitor I/F 15, the external I/F 17, the CPU 18 which will be described later, and the above-mentioned circuits.

The processing apparatus 2 comprises: a calculating device 21 which comprises, e.g., a personal computer or the like, receives the subject spectroscopic image outputted from the external I/F 17, calculates three XYZ excitation values by using an input profile as will be described later, and generates a display signal for obtaining, from a display 22 that will be described later, substantially the same three XYZ excitation values as the three XYZ excitation values presumed to be given by the subject with a display profile based on the calculated three XYZ excitation values; and the display 22 which displays the image on which the colors are reproduced at the high fidelity level by using the display signal outputted from the calculating device 21. Although not shown, the processing apparatus 2 comprises a network interface for connecting to the network 3 and the like.

Incidentally, the photographing apparatus 1 and the processing apparatus 2 may be connected by wiring. Alternatively, the photographing apparatus 1 and the processing apparatus 2 may be connected by radio frequency using Bluetooth or radio LAN or may be integrally configured.

Figure 3:
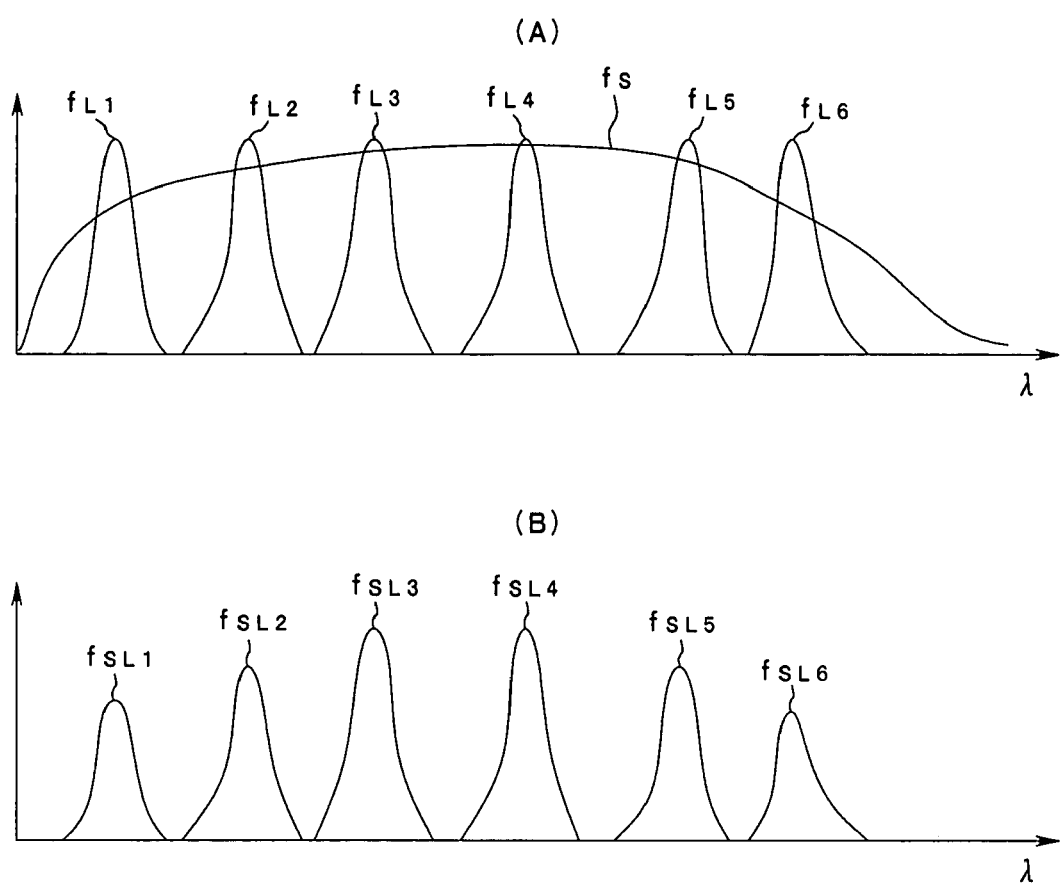
FIG. 3 is a graph showing spectroscopic sensitivity characteristics of a CCD, light-emitting spectrums of the LEDs, and spectroscopic characteristics of them according to the first embodiment.

FIG. 3 is a graph showing the spectroscopic sensitivity characteristics of the CCD 8, the light-emitting spectrums of the first to sixth LEDs 6a to 6f, and the spectroscopic characteristics thereof.

Referring to FIG. 3(A), the first to sixth LEDs 6a to 6f serving as the light-emitting devices have varied independent light-emitting spectrums. The light of the first LED 6a shown by a curve fL1 is blue having the small amount of violet, for example. The light of the second LED 6b shown by a curve fL2 is blue having the small amount of green, for example. The light of the third LED 6c shown by a curve fL3 is green having the small amount of blue, for example. The light of the fourth LED 6d shown by a curve fL4 is green having the small amount of yellow, for example. The light of the fifth LED 6e shown by a curve fL5 is orange, for example. The light of the sixth LED 6f shown by a curve fL6 is red, for example.

In the shown example, the light-emitting spectrums of the first to sixth LEDs 6a to 6f are completely separated without overlaying each other. However, the light-emitting spectrums of the first to sixth LEDs 6a to 6f may be partly overlaid. Further, the number of types of LEDs is not limited to six and an arbitrary number of types of LEDs may be properly combined.

The spectrums of the illuminating light of the LEDs may be arrayed at an equal wavelength interval (at which peaks, for example, are aligned at an equal interval in the wavelength direction), at an equal wavelength ratio interval (at which the peaks or the like are aligned at a predetermined ratio interval in the wavelength direction), at a specific array for specific purpose (by which the peaks or the like are specifically aligned in the wavelength direction for the specific purpose), by the setting to be sequentially multiplying a specific wavelength-color (by which the peaks or the like are aligned at the position for sequentially multiplying the wavelength by using the specific wavelength as a basic wavelength), by the arrangement of a specific polarizing color (by which the blight expressed by the peaks aligned in the wavelength direction is polarized in the specific direction), or by the arrangement of light extended to outside the visible light area (by which the light expressed by the peaks aligned in the wavelength direction reaches an area outside the visible light area). The spectrum alignment matching the using purpose may be selected.

The light-emitting device uses the LED serving as a semiconductor light-emitting device with high luminance that is light in weight, compact in size, and is easily obtained because of its relatively inexpensive price. However, the light-emitting device is not limited to this and may be a semiconductor laser such as an LD (laser diode) or another light-emitting device.

According to the first embodiment, the CCD 8 is a monochrome-type one. As shown by a curve fS in FIG. 3(A), the sensor sensitivity entirely covers the visible light area. The image pick-up device uses a monochrome-type CCD. However, the image pick-up device is not limited to this and may use a color-type CCD as will be described later, a CMOS-type CCD, or other image pick-up devices.

Referring to FIG. 3(B), curves fSL1 to fSL6 show the spectroscopic sensitivity characteristics, when the CCD 8 receives the light of the subject images illuminated by the first to sixth LEDs 6a to 6f. The difference of wavelengths having the total spectroscopic sensitivity characteristics is electrically processed later or is corrected as the input profile of the photographing apparatus 1.

FIG. 2 is a diagram showing an example configuration and an example of the arrangement of the LEDs.

Referring to FIG. 2(A), the first to sixth LEDs 6a to 6f comprise six primary colors. Three sets of the first to sixth LEDs 6a to 6f (three sets for each color) are sequentially arranged like a ring. The arranging sequence shown in FIG. 2(A) is one example, the present invention is not limited to this and can be widely applied to an arbitrary arrangement such as inverse sequence and random arrangement.

Referring to FIG. 2(B), a plurality of light-emitting portions 6A are arranged like a ring. The first to sixth LEDs 6a to 6f are arranged such that the light-emitting portions 6A include the six primary colors. In the example shown in FIG. 2(B), one light-emitting portion 6A includes all the six primary colors, but the present invention is not limited to this and the six primary colors are separately arranged to a plurality of light-emitting portions 6A, e.g., three primary colors are arranged to the two light-emitting portions 6A.

Referring to FIG. 2(C), one ends 6Ba to 6Bf of a fiber bundle 6B are connected to the first to sixth LEDs 6a to 6f and the other end 6Bg of the fiber bundle 6B is formed like a ring. Thus, the illuminating light emitted from the first to sixth LEDs 6a to 6f is incident on the bundle fiber ends 6Ba to 6Bf. The bundle fiber end comprises a plurality of fine fibers. At an emitting portion 6Bg of the bundle fiber, the fine fibers of the LEDs are mixed and thus the light is irradiated to the subject by using the fibers as an even light source like a ring. The influence of total reflection from the subject is suppressed.

The arrangement of the LEDs is not limited to the examples shown in FIG. 2. As long as the CCD 8 does not disturb the image pick-up operation, the arrangement of the LEDs can may be like a ring one, cross one, rectangular one, random one, and another proper one.

Next, a description is given of two image capturing modes in the photographing apparatus 1.

As mentioned above, the photographing apparatus 1 picks-up the moving image as the normal RGB images and the still image as the subject spectroscopic images of the six primary colors for reproducing the color at the high fidelity level. In a capturing mode of a monitoring image, the moving image is picked-up. In a capturing mode of a spectroscopic image, the still image is picked-up.

The two modes are switched by pressing a photographing button 14a (refer to FIG. 16) comprising a pressing button switch included in the operating switch 14.

That is, the capturing mode of the monitoring image is automatically set by switching-on a power switch, and the subject image is displayed on the LED monitor 16 as the moving image. In this state, the portion in the subject for photographing the spectroscopic image is searched and the photographing apparatus 1 is positioned. Thus, the portion in the subject to be photographed is within the image pick-up range and the photographing apparatus 1 is positioned. By pressing the photographing button 14a (refer to FIG. 16), the capturing mode of the monitoring image is switched to the capturing mode of the spectroscopic image and the subject spectroscopic image is captured as the still image.

After capturing the subject spectroscopic image, the mode is returned to the capturing mode of the monitoring image and the portion in the subject for next capturing spectroscopic image is searched.

Although not shown, a result of analyzing the spectroscopic image or the color reproduction using the captured spectroscopic image is displayed on the LCD monitor 16 or the display 22 by another setting just after capturing the spectroscopic image.

Figure 4:
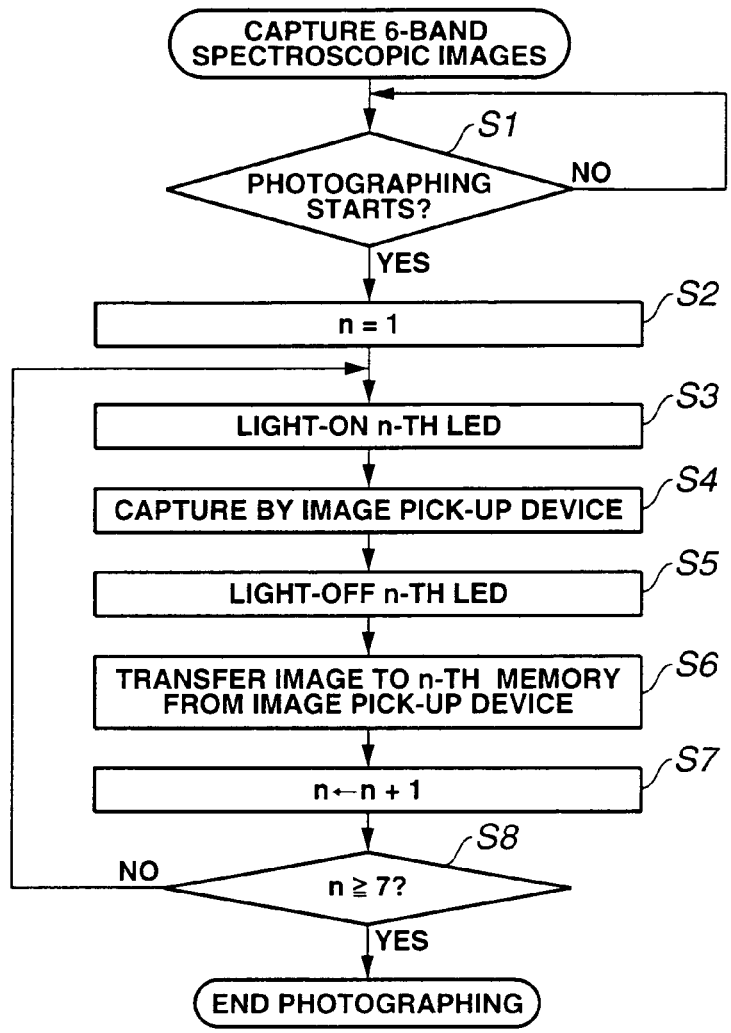
FIG. 4 is a flowchart showing the operations of the light emission of the LEDs for capturing 6-band spectroscopic images and the image capturing by an image pick-up device according to the first embodiment.
Figure 5:
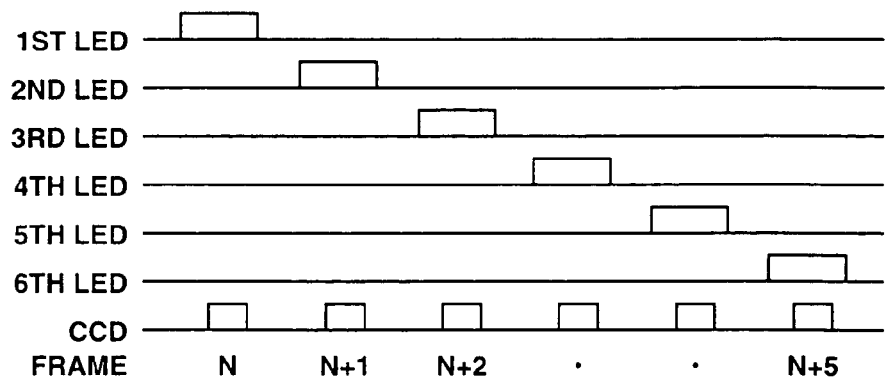
FIG. 5 is a timing chart showing a state of the operations of the light emission of the LEDs and the image capturing by the image pick-up device upon capturing the 6-band spectroscopic images according to the first embodiment.
Figure 6:
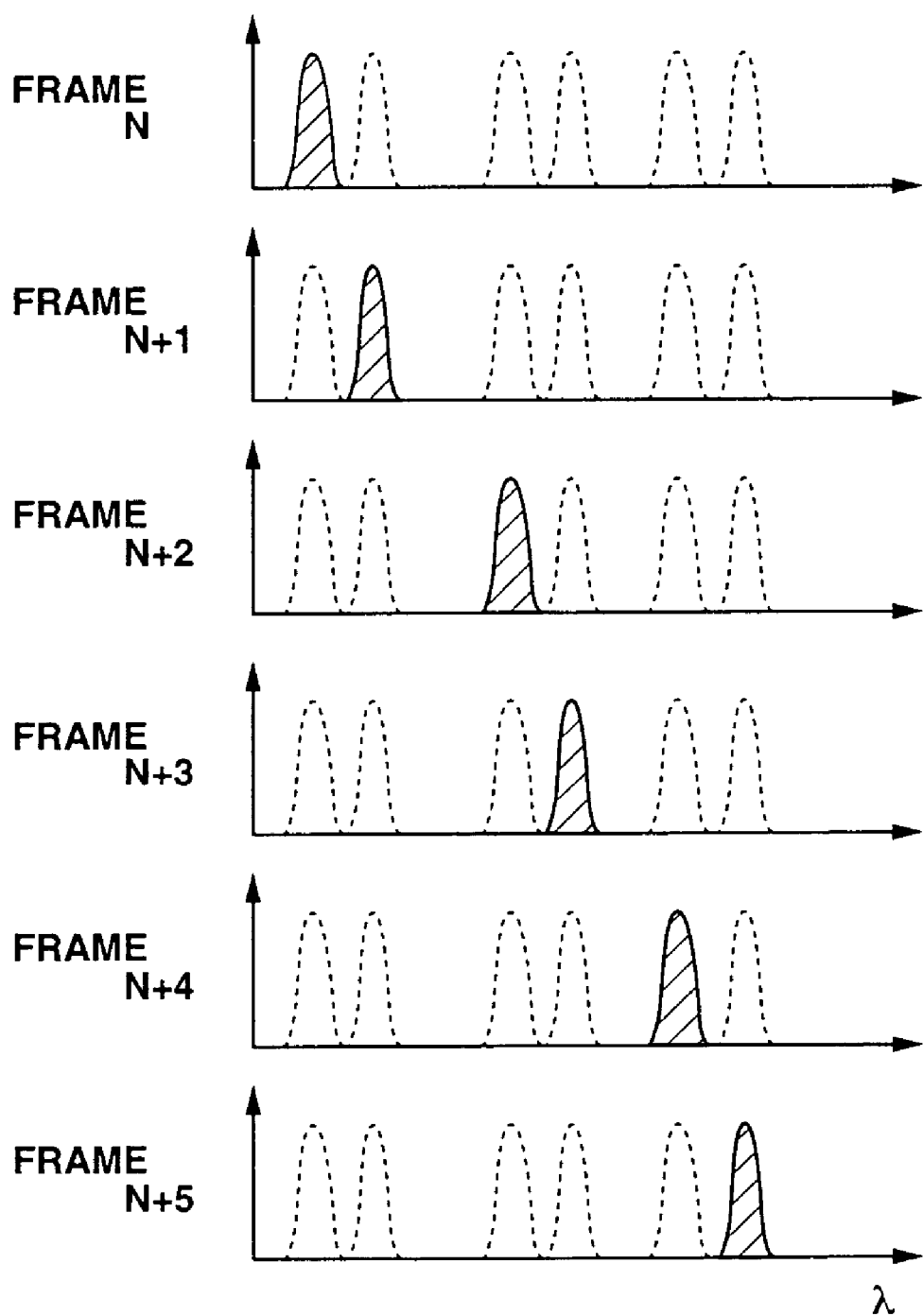
FIG. 6 is a graph showing band characteristics of frames in the operation for capturing the 6-band spectroscopic images according to the first embodiment.

Next, a description is given of the operation of the capturing mode of the spectroscopic image in the image processing system with reference to FIGS. 4 to 6. FIG. 4 is a flowchart showing the operations for light emission of LEDs and for image capturing by the image pick-up device upon capturing the 6-band spectroscopic images. FIG. 5 is a timing chart showing a state of the operations for light emission of the LEDs and for image capturing by the image pick-up device upon capturing the 6-band spectroscopic images. FIG. 6 is a graph showing the band characteristics of the frames upon capturing the 6-band spectroscopic images.

By pressing the photographing button 14a (refer to FIG. 16), the capturing mode of the monitoring image is switched to the capturing mode of the spectroscopic image and then it is determined whether or not the image pick-up operation of the spectroscopic image starts (step S1). When the image pick-up operation of the spectroscopic image promptly starts by pressing the photographing button 14a, the determination may not be performed. However, when the photographing button 14a comprises a two-step pressing button and adjusts the focusing or the amount of exposure at the first pressing step serving as half pressing and starts the exposure at the second pressing step serving as the complete pressing, in step S1, it is determined whether or not the operation is to be executed at the second pressing step.

Next, one is set to a variable n (step S2) and the n-th LED is lit-on (step S3). Since n is set to 1, the first LED 6a is lit-on. The illumination light using the first LED 6a is irradiated to the subject via the projecting port 5a of the casing 5. In this case, since the abutting portion 4 is softly abutted to the subject surface so as to prevent the flow-in of the ambient light, the only the illumination light from the first LED 6a is projected to the subject. The reflecting light from the subject is formed onto the CCD 8 by using the image pick-up optical system 7.

After starting the light-on operation of the first LED 6a, the image pick-up operation of the CCD 8, specifically, the storaging of charges starts (refer to FIG. 5) (step S4).

After ending the image pick-up operation using the CCD 8, then, the first LED 6a is lit-off (step S5). The image data is read from the CCD 8, is converted into digital data by the A/D converter 9, and is stored in a predetermined storage area (n-th memory, here, first memory) in the memory 11 (step S6). When the 6-band spectroscopic images are picked-up, the memory 11 has the storage areas serving as the first to sixth memories, and the spectroscopic images are sequentially stored in the storage areas.

Then, the variable n is incremented (step S7). Herein, the variable n is incremented from one to two.

It is determined whether or not the variable n is seven or more (step S8). Since the variable n is 2 yet here, the processing returns to step S3 whereupon the second LED 6b is lit-on. After that, the operation in steps S3 to S7 is performed.

After the sixth LED 6f is lit-on when the variable n is 6 and the operation to step S6 ends, the 6-band spectroscopic image is captured as shown in FIG. 6 and is stored in the memory 11. In step S7, the variable n is incremented to 7, then, in step S8, it is determined that the variable n reaches 7 and the operation for capturing the 6-band spectroscopic images ends.

Figure 7:
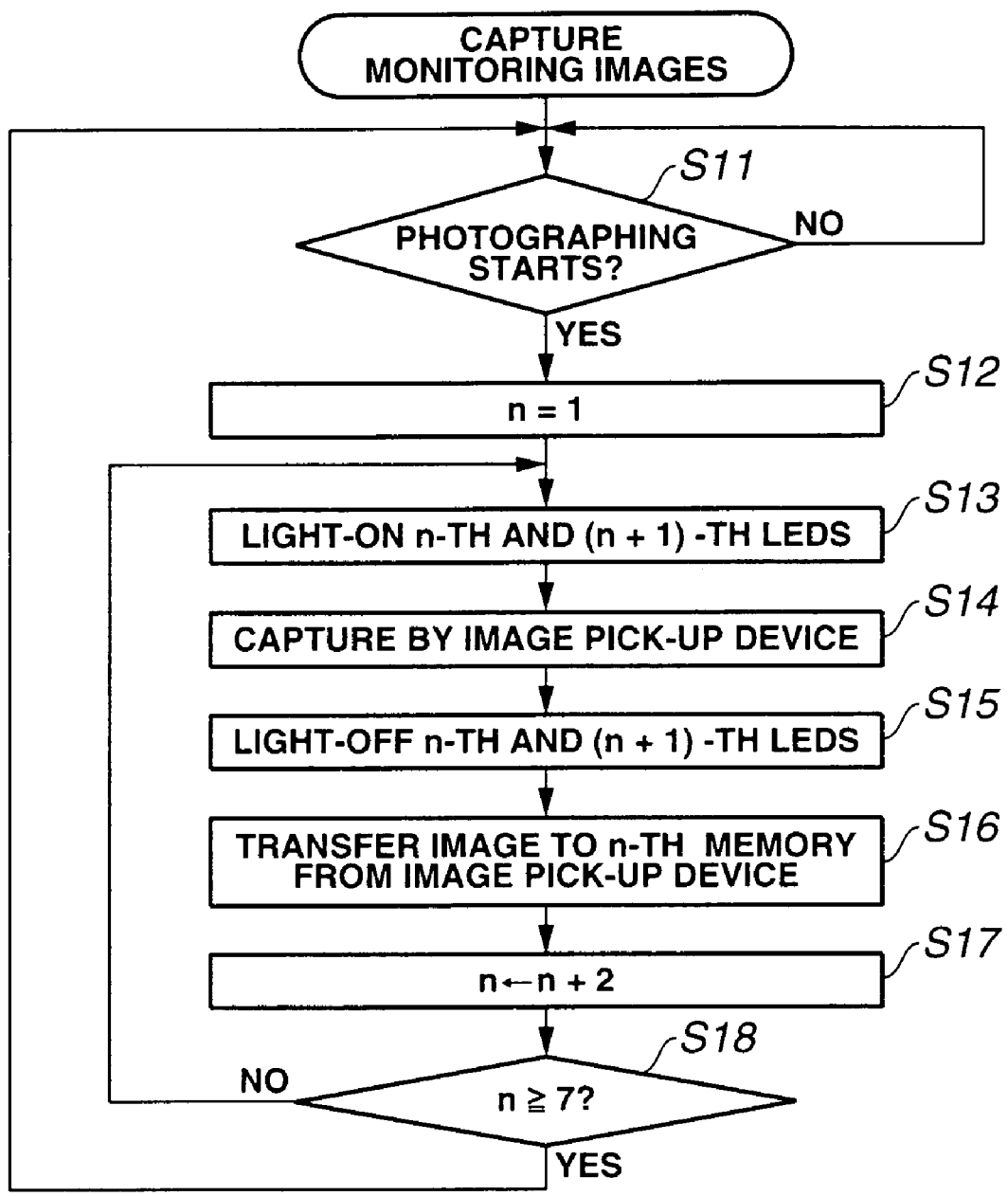
FIG. 7 is a flowchart showing the operations of the light emission of the LEDs and the image capturing by the image pick-up device according to the first embodiment.
Figure 8:
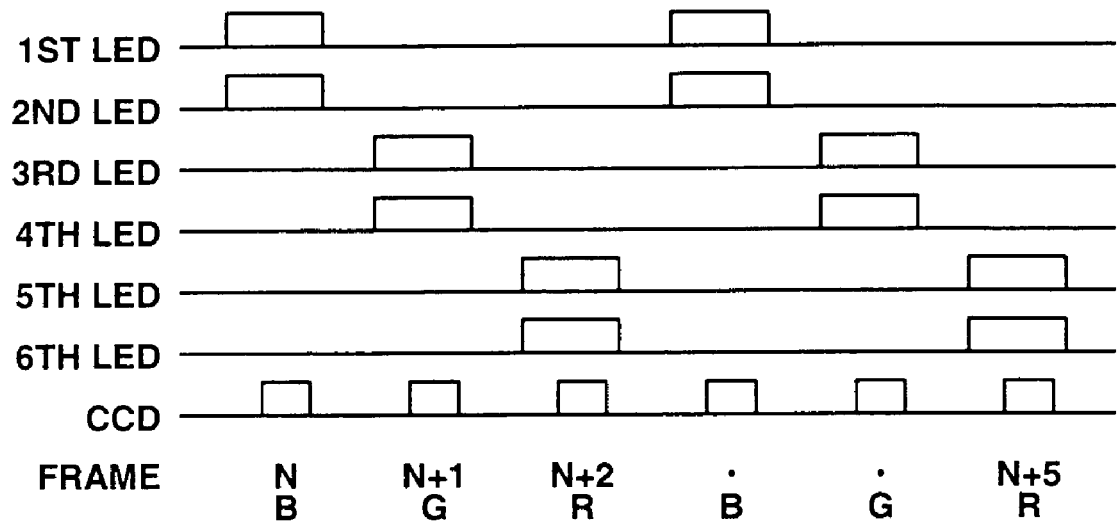
FIG. 8 is a timing chart showing a state of the operations of the light emission of the LEDs and the image capturing by the image pick-up device upon capturing a monitoring image according to the first embodiment.
Figure 9:
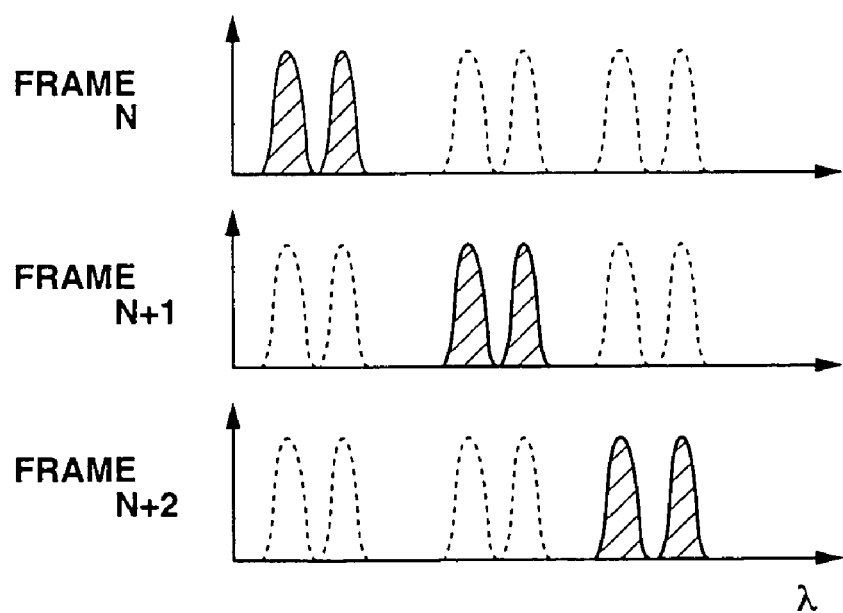
FIG. 9 is a graph showing band characteristics of the frames upon capturing the monitoring image according to the first embodiment.

Although not shown, the image capturing timings by the LEDs and the CCD are not limited to the foregoing. Identically, the LEDs are lit-on after starting capturing the image by the image pick-up device and the image capturing by the image pick-up device ends after the LEDs are lit-off Next, a description is given of the operation in the capturing mode of the monitoring image in the image processing system with reference to FIGS. 7 to 9. FIG. 7 is a flowchart showing the operation for light emission of the LEDs and for image capturing by the image pick-up device upon capturing the monitoring image. FIG. 8 is a timing showing a state of the operation for light emission of the LEDs and for image capturing by the image pick-up device upon capturing the monitoring image. FIG. 9 is a graph showing the band characteristics of the frames upon capturing the monitoring image.

In the capturing mode of the monitoring image, in the illuminating light of the six primary colors from the first to sixth LEDs 6a to 6f, the first LED 6a and the second LED 6b emit the light corresponding to the range of blue (B), the third LED 6c and the fourth LED 6d emit the light corresponding to the range of green (G), and the fifth LED 6e and the sixth LED 6f emit the light corresponding to the range of red (R), thereby capturing the RGB images serving as the moving image by the frame sequential method.

Herein, the primary colors of the light emission are selected for using on general RGB images. However, the present invention is not limited to this and another primary color of the light emission may be selected for using on specific application.

The capturing mode of the monitoring image is set by switching-on the power switch or the mode is returned to the capturing mode of the monitoring image by ending the capturing mode of the spectroscopic image. Then, the start of the image pick-up operation of the monitoring image is waited (step S11).

Herein, the image pick-up operation promptly starts and the variable n is set to one (step S12). The n-th LED and the (n+1)-th LED are lit-on (step S13). Since the variable n is set to one, the first LED 6a and the second LED 6b are lit-on.

After starting the light-on operation of the first LED 6a and the second LED 6b, the image pick-up operation by the CCD 8 starts (refer to FIG. 8) (step S14).

After ending the image pick-up operation by the CCD 8, the first LED 6a and the second LED 6b are lit-off (step S15). The image data is read from the CCD 8, is converted into the digital data by the A/D converter 9, and is stored in a predetermined storage area (n-th memory, here, first memory) in the memory 11 via the bus 10 (step S16).

Then, the variable n is increased by two (step S17). The variable n is increased from 1 to 3.

It is determined whether or not the variable n is 7 or more (step S18). Here, since the variable n is 3 yet, the processing returns to step S13 whereupon the third LED 6c and the fourth LED 6d are lit-on. The operation in steps S13 to S17 is performed.

Thus, the variable n is 5 and further the processing returns to step S13 whereupon the fifth LED 6e and the sixth LED 6f are lit-on. The operation to step S16 ends. The RGB images with the band characteristics shown in FIG. 9 are sequentially captured in order of R, G, and B, and are stored in the first memory, third memory, and fifth memory in the memory 11. The variable n is incremented to 7 in step S17 and therefore it is determined in step S18 that the variable n reaches 7.

After capturing the RGB images, the processing returns to step S11 whereupon it is determined whether or not the next RGB images are captured. When the capturing mode of the monitoring image is sequentially set, the next RGB images are captured. This operation is repeated, thereby capturing the RGB moving images.

Although not shown, the image capturing timings of the LEDs and CCD are not limited to this. Identically, the LEDs are lit-on after starting capturing the image by the image pick-up device and the operation for capturing the image by the image pick-up device ends after lighting-off the LEDs.

The above-mentioned image data stored in the memory 11 is then read, is converted into the image signal for display on the monitor, and is outputted and displayed on the LCD monitor 16 via the monitor I/F 15. Further, the setting of the image processing system is changed, thereby displaying the image data on the display 22 of the processing apparatus 2.

In order to ensure the illuminance, the LEDs for the six primary colors are divided into three groups including the two LEDs, namely, R devices, G devices, and B devices. However, the present invention is not limited to this. For example, the LED for one primary color may be emitted for the light, specifically, the first LED 6a may be emitted with respect to the light B (blue), the third LED 6c may emit the light G (green), and the fifth LED 6e may be emitted with respect to the light R (red). In this case, the LED may be selected such that the spectroscopic characteristics of the LEDs match the RGB light emission.

Only the LED for one primary color or the LEDs for a plurality of primary colors may be lit-on, thereby capturing a monochrome monitoring image. Consequently, the image can be displayed at a high speed on the monitor.

FIG. 10 is a diagram showing an example of lighting-on the LEDs when the three LEDs for each of six primary colors are arranged.

The light-emitting mode includes a case of lighting-on all the LEDs, a case of lighting-on one LED for one primary color, a case of lighting-on the three LEDs for one primary color, a case of lighting-on the LEDs for six primary colors one by one, a case of lighting-on the six LEDs of blue (B) in the eighteen LEDs for six primary colors, a case of lighting-on the six LEDs of green (G) in the eighteen LEDs for six primary colors, a case of lighting-on the six LEDs of red (R) in the eighteen LEDs for six primary colors, a case of lighting-on the three LEDs of blue (B) in the eighteen LEDs for six primary colors, a case of lighting-on the three LEDs of green (G) in the eighteen LEDs for six primary colors, or a case of lighting-on the three LEDs of red (R) in the eighteen LEDs for six primary colors. As mentioned above, the devices for each color simultaneously emit the light and the devices collected at each position simultaneously emit the light.

The photographing apparatus 1 according to the first embodiment picks-up the image of the subject either on contact or on noncontact with the subject. However, in order to accurately reproduce the image, it is necessary to prevent the influence from the light generated by devices other than the photographing apparatus 1.

Therefore, in the case of picking-up the subject image in the noncontact state, the illumination of the exterior lighting needs to be lit-off.

In the case of the subject image which is photographed in the contact state, such as the image of the painting surface, skin surface, or close image, the abutting portion 4 that is cylindrically shaped is softly abutted to the subject (refer to FIG. 1) as mentioned above. The shielding performance is ensured.

Figure 11:
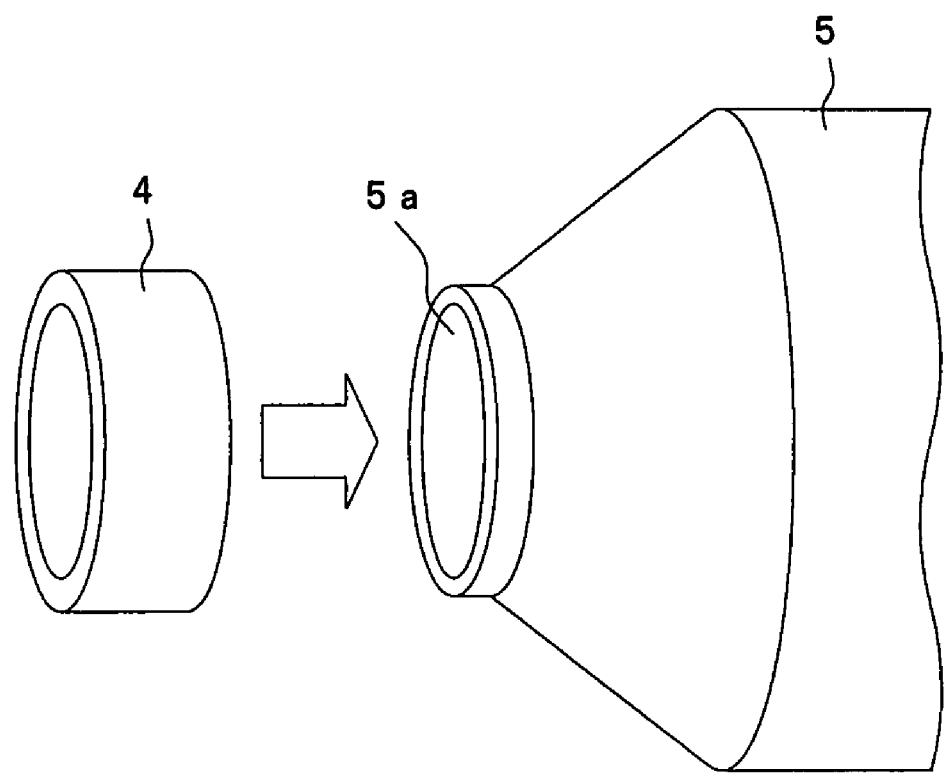
FIG. 11 is a perspective view showing an abutting portion which is detachable to a projecting portion of a casing according to the first embodiment.

Since the abutting portion 4 is used in the image pick-up operation in the contact state, referring to FIG. 11, the abutting portion 4 is detachable and disposable member in view of the sanitation for preventing the bacterial contamination or dirt when the subject is the human body and in view of preventing the transfer of dirt when the subject is a painting plate. FIG. 11 is a perspective view showing the abutting portion 4 that is detachable to the projecting port 5a of the casing 5.

The abutting portion 4 contains a heat insulator when the subject is at the high temperature or low temperature, an electric insulator when the subject is electrostatic or conductive, a solution-proof material when the subject is dipped in the solution, or a glass window for projecting the illuminating light and receiving the reflecting light. Since the abutting portion 4 is a single detachable part, the abutting portion 4 is easily formed, including the various above-mentioned materials. Further, an observing window that is opened and is closed to the abutting portion 4 is easily arranged to observe the subject surface by the naked eyes.

According to the first embodiment, one specific primary color or a plurality of primary colors are used from among the plurality of primary colors whose light is emitted by the LEDs, thereby enabling the use for the examination or determination for specific application.

A description is given of the color reproduction in the processing apparatus 2.

The subject spectroscopic image is recorded to the memory 11 by the image pick-up operation of the photographing apparatus 1, is sent to the processing apparatus 2 via the external I/F 17, and is recorded to an image memory unit 32 (refer to FIG. 12) incorporated in the processing apparatus 2. Then, the calculating device 21 that is operated by predetermined software performs the color reproduction or image processing of the recorded image. The processing result is displayed on the display 22 of the processing apparatus 2 or is transferred and is displayed on the LCD monitor 16.

Figure 12:
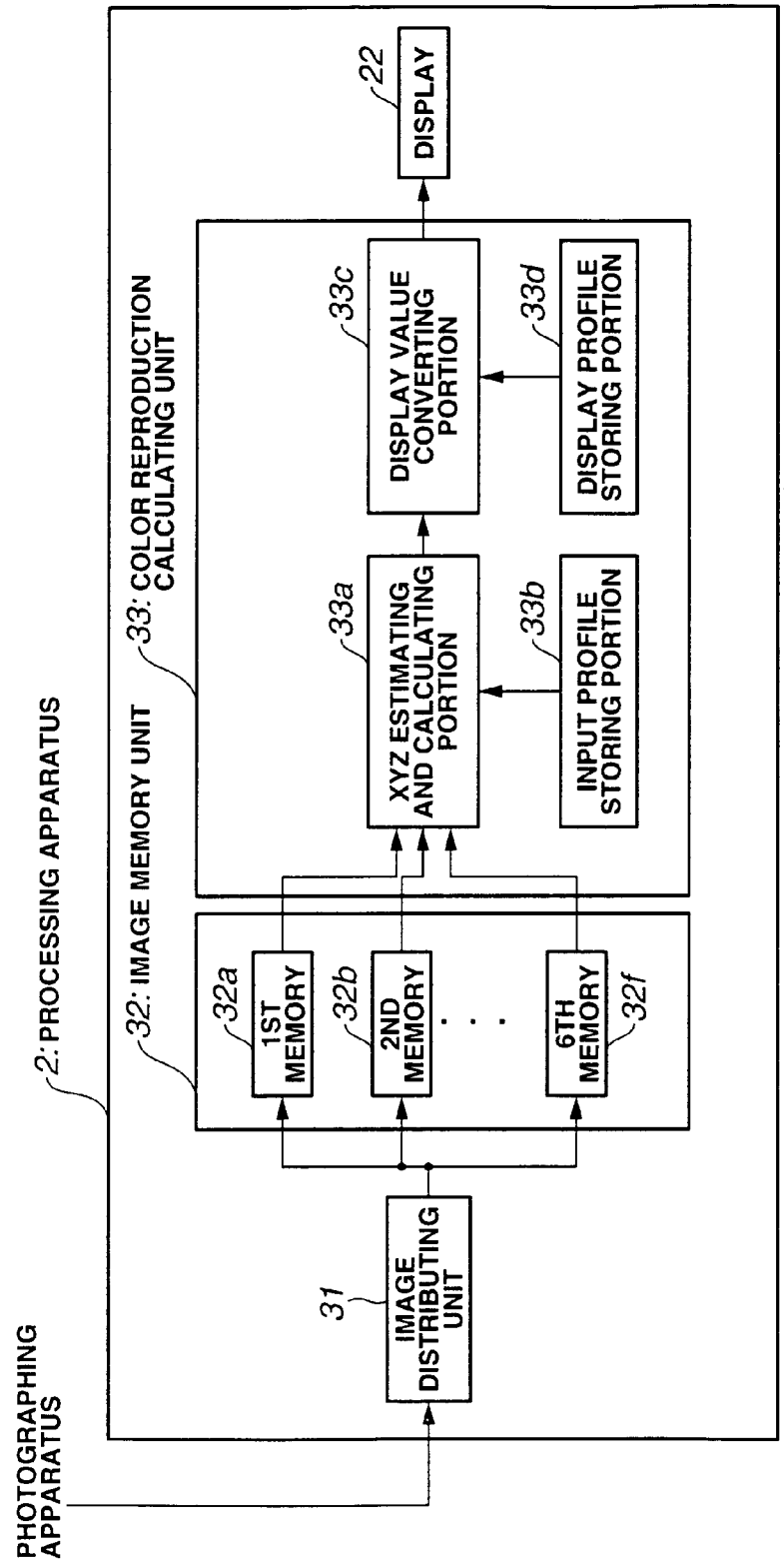
FIG. 12 is a block diagram showing the configuration of the color reproduction for displaying on a display in a processing apparatus according to the first embodiment.

FIG. 12 is a block diagram showing the configuration for performing color reproduction to display on the display 22 in the processing apparatus 2.

The processing apparatus 2 comprises: an image distributing unit 31 which distributes the storage areas in the image memory unit 32 depending on which of the first to sixth LEDs 6a to 6f illuminates the subject spectroscopic images inputted from the photographing apparatus 1; the image memory unit 32 having first to sixth memories 32a to 32f serving as the storage memories for storing the subject spectroscopic images distributed by the image distributing unit 31; and a color reproduction calculating unit 33 which reads the subject spectroscopic image stored in the image memory unit 32 and calculates and outputs display image data for displaying the image that is color-reproduced at the high fidelity level on the display 22. The components 31 to 33 are included in the calculating device 21 shown in FIG. 1. Further, the processing apparatus 2 comprises the display 22 which displays the image that is color-reproduced at the high fidelity level based on the display image data outputted from the color reproduction calculating unit 33.

The color reproduction calculating unit 33 comprises: an input profile storing portion 33b which stores a profile on the photographing apparatus 1; an XYZ estimating and calculating portion 33a which reads the subject spectroscopic images stored in the first to sixth memories 32a to 32f in the image memory unit 32 and creates the image data having three XYZ excitation values by the estimation and calculation using the input profile stored in the input profile storing portion 33b and a predetermined equal-color function set therein; a display profile storing portion 33d which stores a profile on the display 22; and a display value converting portion 33c which creates the display image data for being outputted on the display 22 by the calculation using the image data of the three XYZ excitation values estimated by the XYZ estimating and calculating portion 33a and the display profile stored in the display profile storing portion 33d.

The input profile stored in the input profile storing portion 33b is as disclosed in, e.g., Japanese Unexamined Patent Application Publication No. 2000-341499. The input profile is calculated based on the characteristics and setting of the photographing apparatus 1 including the spectroscopic sensitivity of the CCD 8 used for the image pick-up operation (image input device), spectrum data of the illuminating light upon photographing the subject (information on the illuminating light for photographing), spectrum data of the illuminating light at the installing position of the display 22 for observing the created subject image (information on the illuminating light for observation), information such as static characteristics of the spectroscopic reflectance of the photographed subject (information on the subject characteristics).

Figure 14:
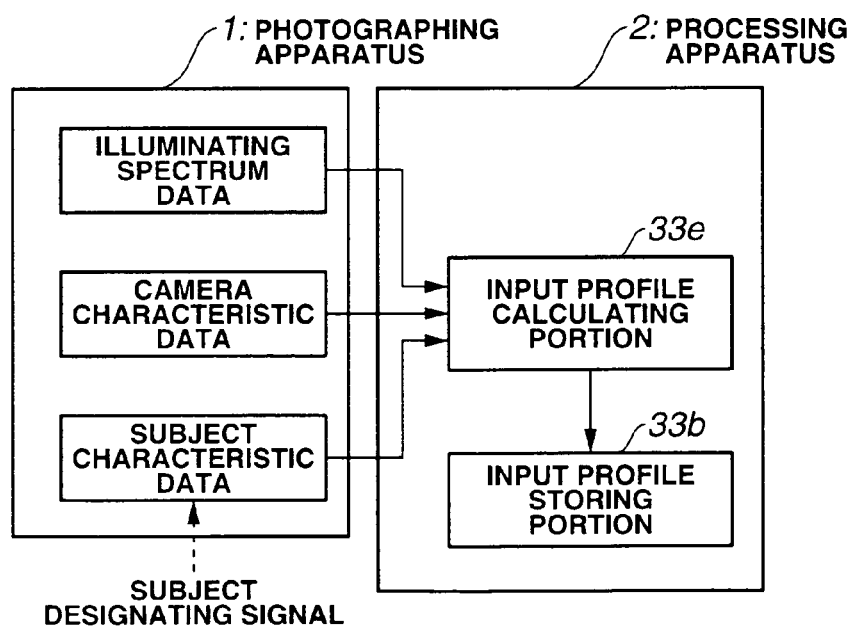
FIG. 14 is a block diagram showing an example configuration for creating an input profile in a processing apparatus according to the first embodiment.

FIG. 14 is a block diagram showing an example configuration for creating the input file in the processing apparatus 2.

Referring to FIG. 14, the input profile may be created based on the data obtained from the photographing apparatus 1 in the processing apparatus 2.

The data obtained by the photographing apparatus 1 includes illumination light spectrum data, camera characteristic data, subject characteristic data, and the like.

The illumination spectrum data is spectrum data on the illumination upon picking-up the image of the subject, for example, and becomes spectrum data of the first to sixth LEDs 6a to 6f included in the photographing apparatus 1 in the contact state. In the non-contact state, the illumination spectrum data includes spectrum data of the external illumination upon photographing the subject.

The camera characteristic data includes characteristics of the image pick-up optical system 7 including a focusing level, image pick-up characteristics of the CCD 8, shutter speed, stop value, and various characteristics.

The subject characteristics include spectroscopic statistic data and the like when the subject is the tooth, skin, or painting material, for example. The operating switch 14 may include in this case a subject designation operating portion to create the input profile with high precision and thus a subject designating signal for designating the subject may be inputted.

Referring to FIG. 14, the processing apparatus 2 which creates the input profile based on the data comprises: an input profile calculating portion 33e which reads the illumination spectrum data, the camera characteristic data, and the subject characteristic data and thus creates the input profile; and the input profile storing portion 33b which stores the input profile created by the input profile calculating portion 33e.

With the above-mentioned configuration, the color can be adaptively reproduced at the high fidelity level even when the photographing apparatus 1 connected to the processing apparatus is changed to the different individual one or different type of device (e.g., the image pick-up optical system 7 is changed) and even when the environment illumination for photographing is changed or the subject serving as the photographing target is variously changed.

The display profile stored in the display profile storing portion 33d is calculated based on information such as a chromaticity value of a display primary-color value of the display 22 (e.g., RGB primary color values when the display 22 is an RGB monitor) and the tone curve of the display 22. The display may be a multi-primary-color reproducing system disclosed in Japanese Unexamined Patent Application Publication No. 2000-338950.

Figure 13:
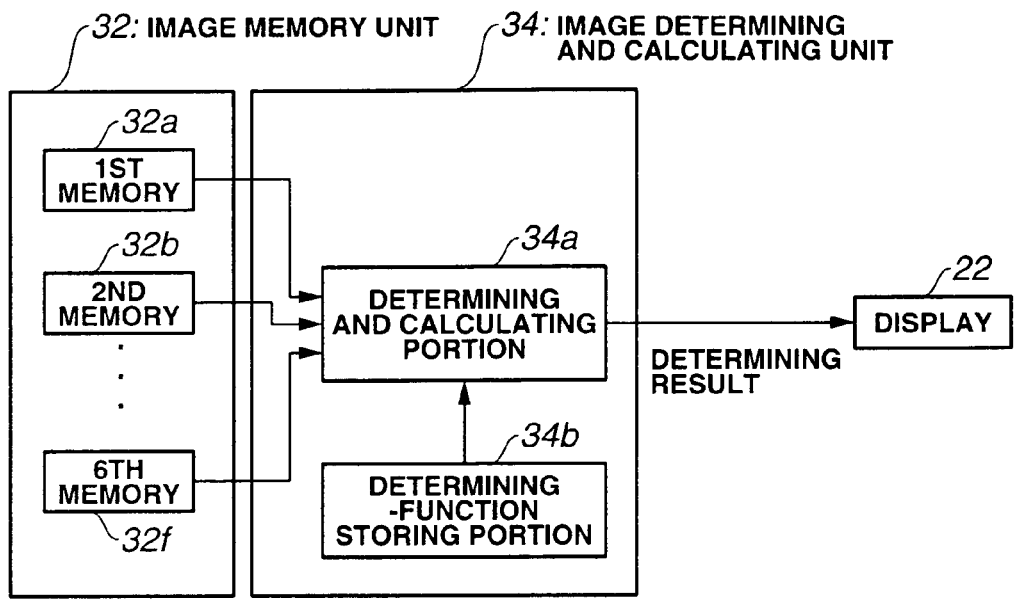
FIG. 13 is a block diagram showing an example configuration for determining an image of a subject based on the captured subject spectroscopic image according to the first embodiment.

FIG. 13 is a block diagram showing an example configuration for image determination of the subject based on the captured subject spectroscopic image.

The subject spectroscopic image stored in the first to sixth LEDs 32a to 32f in the image memory unit 32 is read and is determined on the subject image by an image determining and calculating unit 34. The determining result is outputted and is displayed on the display 22. The image may be determined and may be calculated via a network and the result may be displayed on the LCD monitor 16.

The image determining and calculating unit 34 comprises: a determining function storing portion 34b which stores a determining function for various classification/determination/diagnosis on the subject; and a determining and calculating portion 34a which calculates, by using the determining function, all the six subject spectroscopic images stored in the first to sixth memories 32a to 32f in the image memory unit 32 or at least one subject spectroscopic image selected from the six ones, thus calculates the determining result, and creates image data for displaying the determining result to be displayed on the display 22.

The determining function can be variously replaced depending on for which application the image processing system is used. Therefore, the determining function storing portion 34b may comprise a rewritable or write-once storage medium which can rewrite or add the determining function used depending on the application. An example of the above-mentioned determining function is a function disclosed in Japanese Unexamined Patent Application Publication No. 7-120324.

The image determining and calculating unit 34 shown in FIG. 13 may be provided in the processing apparatus 2, in place of the color-reproduction calculating unit 33 shown in FIG. 12. Alternatively, the image determining and calculating unit 34 shown in FIG. 13 and the color-reproduction calculating unit 33 shown in FIG. 12 may be provided in the processing apparatus 2 and thus the processing may be simultaneously executed or may be performed by selectively switching the necessary one.

Figure 15:
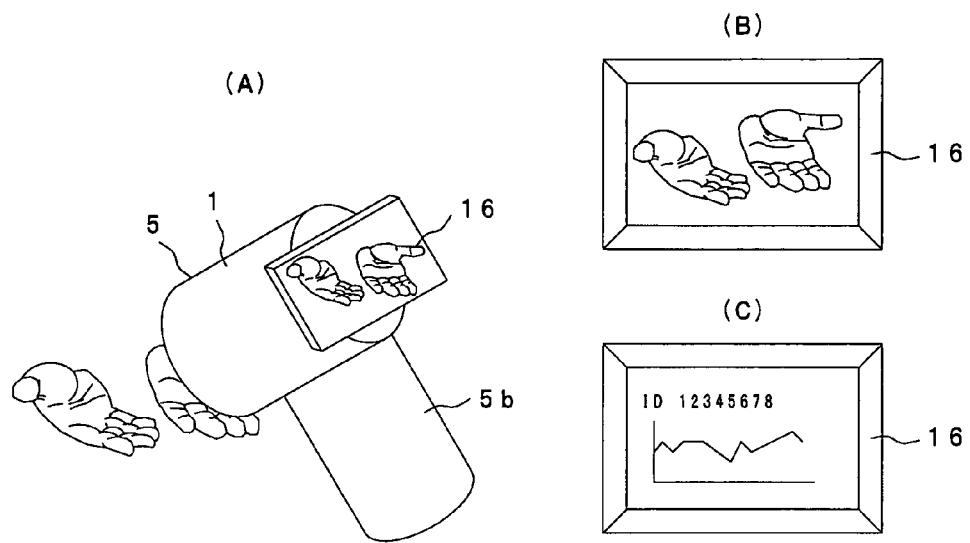
FIG. 15 is a diagram showing a display example on an LCD monitor in a photographing apparatus according to the first embodiment.

Next, FIG. 15 is a diagram showing a display example of the LCD monitor 16 in the photographing apparatus 1.

Referring to FIG. 15(A), the LCD monitor 16 is arranged to the top of a grip portion 5b on the rear side of the casing 5 in the photographing apparatus 1, and displays an image as shown in FIG. 15(B) or 15(C). Herein, an image of the hand is picked-up as an example.

FIG. 15(B) shows a state displaying the moving image picked-up in the capturing mode of the monitoring image. The LCD monitor 16 has a function of a finder.

FIG. 15(C) shows a state for displaying the determining result of the subject image by the image determining and calculating unit 34. The LCD monitor 16 displays an ID number of the subject (e.g., patient number in a diagnostic supporting system in the medical field) and a graph indicating a numerical analysis result obtained by the image determination (e.g., curing process). In addition to the foregoing, the LCD monitor 16 displays various information including a color-reproducing image, patient medical record, various data, and charts.

The LCD monitor 16 functions as a finder upon selecting the photographed portion and functions as a monitor upon displaying a result of color reproduction and a result of classification/determination/diagnosis.

In many cases, the display 22 of the processing apparatus 2 has a wider area and higher definition, as compared with those of the LCD monitor 16 arranged to the handy photographing apparatus 1. Therefore, the display 22 may display the activation, condition setting, GUI for inputting information such as subject ID, patient career, subject information such as previous information, and the processing result, of processing software executed depending on the purpose in the processing apparatus 2.

An external database is connected to the network 3, for example. The subject information may be obtained to the processing apparatus 2 from the external database, or the processing result in the processing apparatus 2 may be stored into the external database. In this case, in order to ensure the security, the identification can be mutually performed upon connecting the processing apparatus 2 and the external system via the network 3 or the identification can be performed in accordance with the security level which is added to the subject data.

Figure 16:
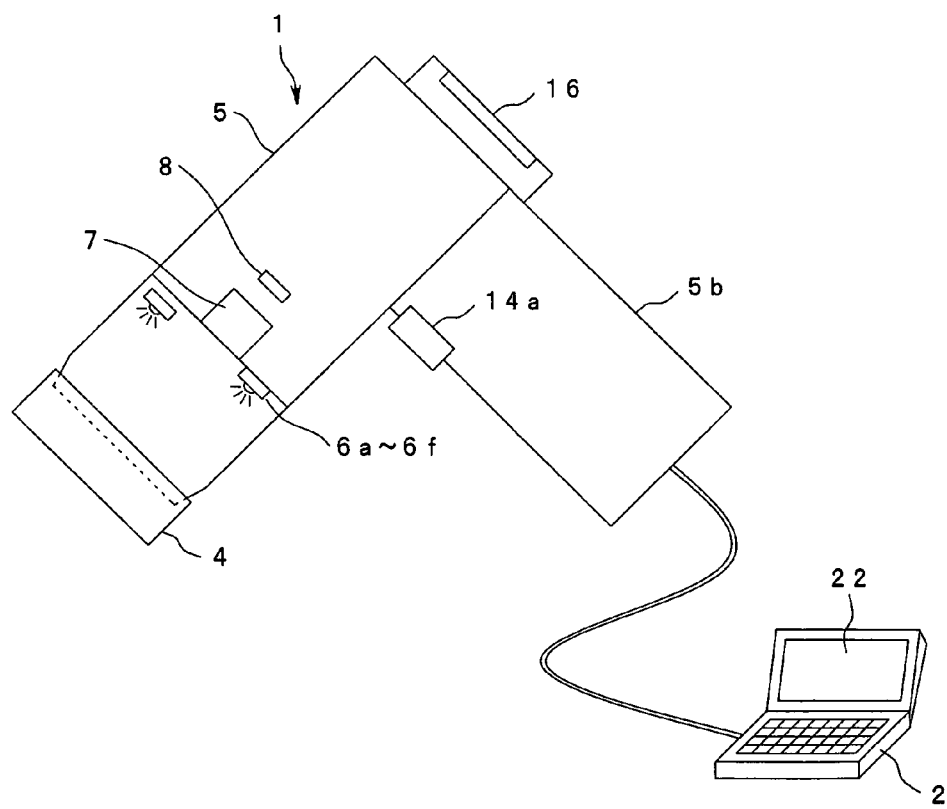
FIG. 16 is a diagram showing an example of a state of using the image processing system according to the first embodiment.

FIG. 16 is a diagram showing a state of using the image processing system.

The photographing apparatus 1 is compact in size and light in weight. For example, the photographing apparatus 1 performs the image pick-up operation by abutting the front end side of the casing 5 having the image pick-up system to a photographing target portion of the subject by gripping the grip portion 5b with one hand.

As mentioned above, the abutting portion 4 is a detachable and disposable member, and shields the external light which irradiates the photographing target portion of the subject.

A photographing button 14a included in the operating switch 14 is arranged on the top of the grip portion 5b, e.g., the position operable with the forefinger. The portion to be photographed is specified on the LCD monitor 16 and then the photographing button 14a is pressed down, thereby shifting the capturing mode of the monitoring image to the capturing mode of the spectroscopic image to perform the image pick-up operation of the spectroscopic image.

The captured spectroscopic images are subjected to data processing in the processing apparatus 2 and is displayed on the display 22. As mentioned above, the processing result of the processing apparatus 2 may be displayed on the LCD monitor 16 in the photographing apparatus 1 by the setting and the like if necessary.

In the example shown in FIG. 16, the processing apparatus 2 is shown as a notebook type personal computer with a display. In this case, the processing apparatus 2 may be connected to the network 3 via an interface (I/F) such as RS-232C, USB, or IEEE1394 provided in the notebook type personal computer.

According to the first embodiment, the photographing apparatus in the image processing system comprises six LEDs having different spectroscopic distributions in the visible light area. The subject spectroscopic image is picked-up by emitting the light of the six LEDs while shading the ambient light. In this case, the photographing apparatus is reduced in size because the compact light semiconductor light-emitting device such as the LED is used as the light source, and the photographing apparatus may be a handy one.

The processing of the processing apparatus enables the display to display the image with the color reproduced at the high fidelity level.

The designation of the LED for emitting the light and the light-emitting sequence of the LEDs enables to pick-up images of not only the normal RGB moving images but also images used for various purposes.

Further, the use of the monochrome CCD slightly reduces the costs. The image data of colors is captured one screen by one screen without causing a lacking of pixel. Therefore, the interpolation is omitted.

Figure 17:
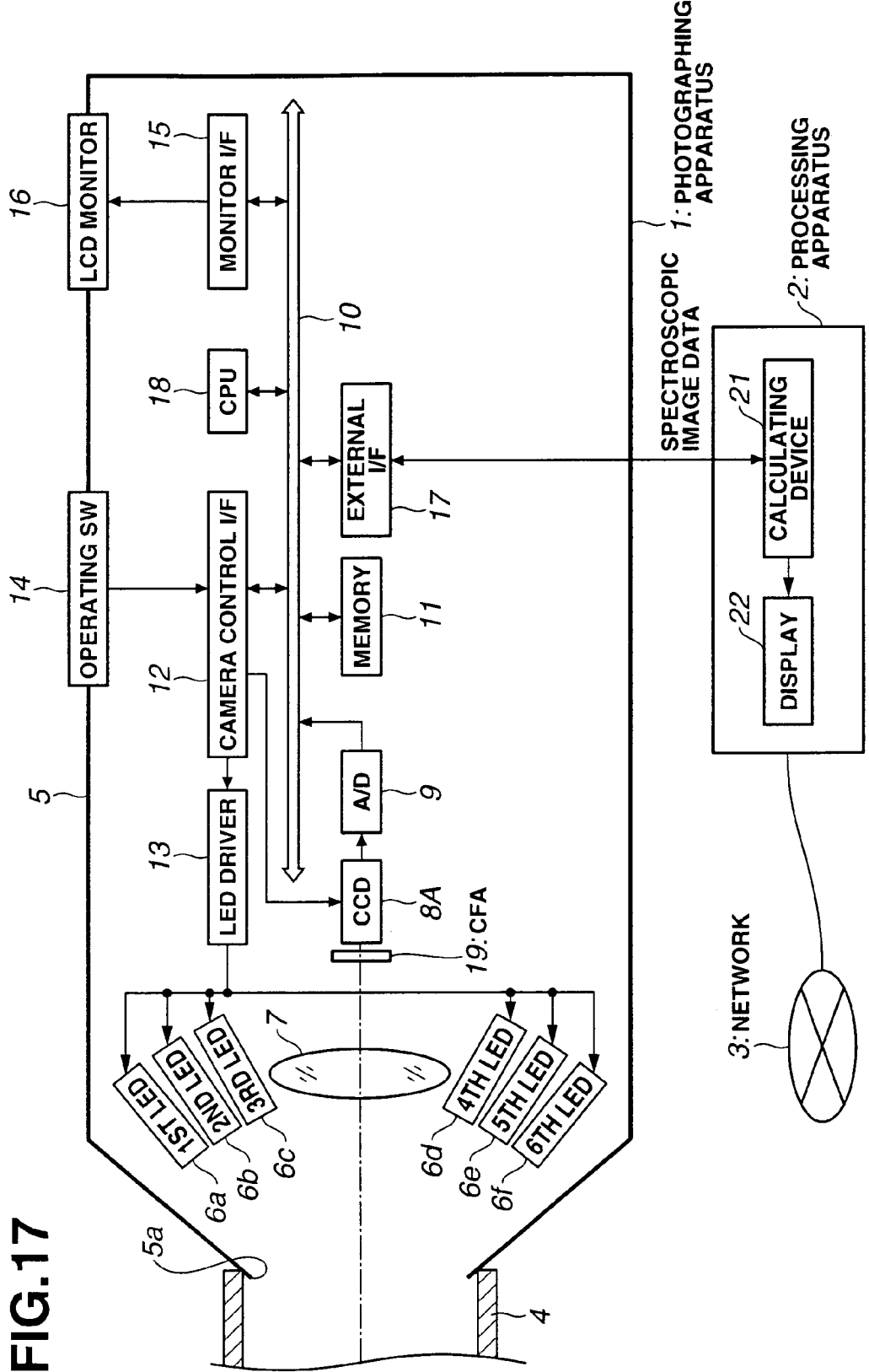
FIG. 17 is a block diagram showing the configuration of an image processing system according to the second embodiment of the present invention.
Figure 19:
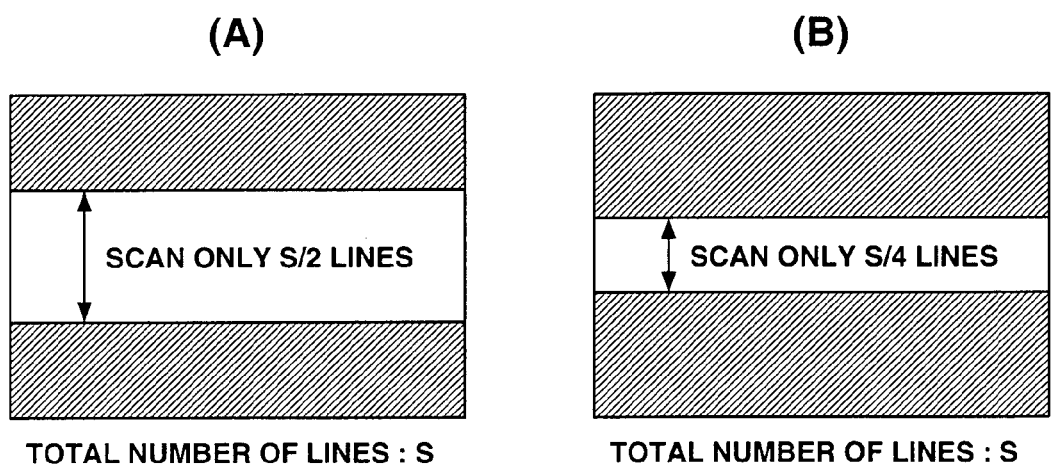
FIG. 19 is a diagram showing a state of lines read in a 2/4-line double-speed mode and a 2/8-line four-time speed mode according to the second embodiment.
Figure 20:
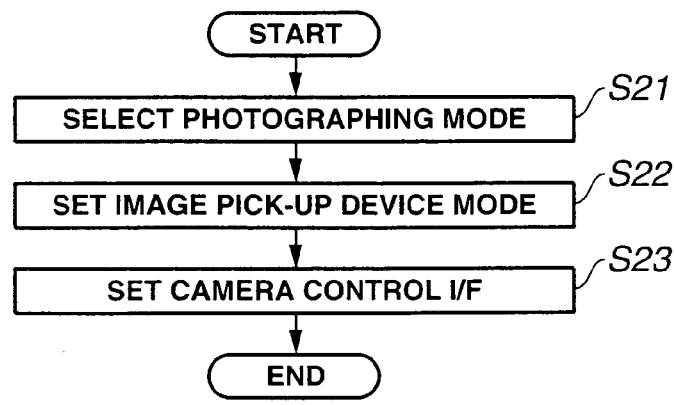
FIG. 20 is a flowchart showing the operation for setting a photographing mode according to the second embodiment.

FIGS. 17 to 20 relate to a second embodiment of the present invention. FIG. 17 is a block diagram showing the configuration of an image processing system. FIG. 18 is a timing chart showing reading states in a full mode and a double-speed mode. FIG. 19 is a diagram showing a state of lines read in a 2/4-line double-speed mode and a 2/8-line four-time speed mode. FIG. 20 is a flowchart showing the operation for setting a photographing mode.

According to the second embodiment, the same components as those according to the first embodiment are designated by the same reference numerals and are not described. Mainly, only different portions are described.

The second embodiment uses the basic configuration according to the first embodiment. Further, according to the second embodiment, it is possible to adjust an image reading speed from a color CCD having a color filter array (CFA) 19 in front of the image processing system.

The image reading speed corresponds to a display speed, and the display speed cannot be faster than the image reading speed.

Generally, in the case of monitoring the image, preferably, the display interval is 30 images/sec or more. As a number N of primary colors increases, the display interval becomes long in proportion to the increase, and a flickering state and the large image positional shift due to difference of time to capture a primary color image are caused.

Therefore, according to the second embodiment, referring to FIG. 17, a camera control I/F 12A adjusts the image reading speed from a CCD 8A so that the long display interval is prevented and the display interval is constant irrespective of the read number N of primary colors.

A description is given of the operation for setting the photographing mode with reference to FIG. 20.

An operation for selecting the photographing mode is inputted from the operating switch 14 (step S21) and the CPU 18 detects the input and then records the set photographing mode and the information thereon to a part of recording area in the memory 11 (step S22). Further, the CPU 18 issues a control command for changing the photographing mode to the camera control I/F 12A (step S23).

The camera control I/F 12A receives the instruction, controls the driving operation of the CCD 8A, and changes the photographing mode. In this case, the camera control I/F 12A controls the LED driver 13 intrelockingly to the operation of the CCD 8A, thereby adjusting the amount of light emission of the first to sixth LEDs 6a to 6f together.

The photographing mode set by the photographing apparatus 1 is as follows, for example.
(1) Full mode
(2) Reading double-speed mode
(3) 2/4 line double-speed mode
(4) 2/8 line four-time-speed mode
(5) 2/16 line eight-time-speed mode
(6) First center-portion scanning mode
(7) Second center-portion scanning mode
(8) Third center-portion scanning mode
(9) Fourth center-portion scanning mode
(10) First center-portion high-speed scanning mode
(11) Second center-portion high-speed scanning mode Referring to FIG. 18(A), the "full mode" is a normal mode for sequentially reading all the pixels of all scanning lines of the CCD 8A at the normal speed. Here, the frames include the frame for simultaneously emitting the light of the first LED 6a, the third LED 6c, and the fifth LED 6e, and the frame for simultaneously emitting the light of the second LED 6b, the fourth LED 6d, and the sixth LED 6f. Means for capturing the six-primary-color image by the above-mentioned light emission will be described later according to the third embodiment.

As compared with the normal mode shown in FIG. 18(A), the "reading double-speed mode" is a mode for sequentially reading all the pixels of all the scanning lines of the CCD 8A at the double speed of the normal one as shown in FIG. 18(B). Although the reading speed of the double speed is explained as an example, the present invention is not limited to this and may be a proper-multiple time or a variable multiple time.

The "2/4 line double-speed mode" is a mode for reducing, to the half, the time for reading one frame by scanning only two lines every four lines. Although the resolution in the vertical direction is half, the image in the entire effective area is obtained.

The "2/8 line four-time-speed mode" is a mode for reducing, to ¼ time of the normal mode, the time for reading one frame by scanning only 2 lines every eight lines.

The "2/16 line eight-time-speed mode" is a mode for reducing, to ⅛ time of the normal mode, the time for reading one frame by scanning only 2 lines every 16 lines.

Referring to FIG. 19(A), the "first center-portion scanning mode" is a mode for reducing, to the half, the time for reading one frame by scanning only a portion of an S/2 (here, reference symbol S denotes the number of all the scanning lines) line in the center portion within the effective area.

Referring to FIG. 19(B), the "second center-portion scanning mode" is a mode for reducing, to ¼ speed, the time for reading one frame by scanning only a portion of an S/4 (here, reference symbol S denotes the number of all the scanning lines) line in the center portion within the effective area.

Similarly, the "third center-portion scanning mode" is a mode for reducing, to ⅛ speed, the time for reading one frame by scanning only a portion of the S/8 line in the center within the effective area.

Similarly, the "fourth center-portion scanning mode" is a mode for reducing, to 1/16 speed, the time for reading one frame by scanning only a portion of the S/16 line in the center within the effective area.

Referring to FIG. 19(A), the "first center-portion high-speed scanning mode" is a mode for reducing, to ¼ speed, the time for reading one frame by scanning only a portion of the S/2 line in the center portion within the effective area at the double speed of the normal one.

Referring to FIG. 19(B), the "second center-portion high-speed scanning mode" is a mode for reducing, to ⅛ speed, the time for reading one frame by scanning only a portion of the S/4 line in the center portion within the effective area at the double speed of the normal one.

The present invention is not limited to those and another means can scan the lines at the high speed. The photographing mode is summarized as follows, including the foregoing.

First, simply, the scanning speed is made fast. This is achieved by adjusting the timing of a trigger timing for instructing the reading start. For example, when the display time of one frame is 1/30 sec, the increase in speed is accomplished by setting the timing of the trigger signal so that the reading time of the prima colors (here, N primary colors) is 1/30/N.

Secondly, the scanning speed is made fast by thinning-out operation. The above first speed increasing means causes the limitation on the fast speed due to the image pick-up device. On the contrary, in the case of thinning out the lines, although the image quality is deteriorated, the speed can be made increased by stable scanning operation. Therefore, the degradation of a frame rate is prevented and the flickering state on the display is prevented. As the thinning-out example, the lines are thinned-out based on a pixel unit in addition to the thinning-out operation for a predetermined period or a predetermined range based on a line unit. When the image pick-up device is an XY address type one, only a desired pixel is precisely read.

Thirdly, the speed is made increased by varying the frame rate depending on the primary color. In CCDs including a standard RGB color filter or the like, in many cases, the green (G) pixels close to a luminance signal are arranged double number of red (R) or blue (B) pixels. In consideration thereof, it is possible to read the frame having the pixels close to the green (G) ones in the six primary colors, corresponding to the double number of frames of the color other than the green, i.e., the red and blue. The present invention is not limited to this and many frames of the specific primary color may be read or a reading rate may be varied step by step in accordance with the necessity.

According to the second embodiment, the same advantages as those according to the first embodiment are obtained. Further, the constant display speed is ensured by changing the reading speed. In the case of the color reproduction at the high fidelity level, the moving image with natural motion is displayed.

Figure 21:
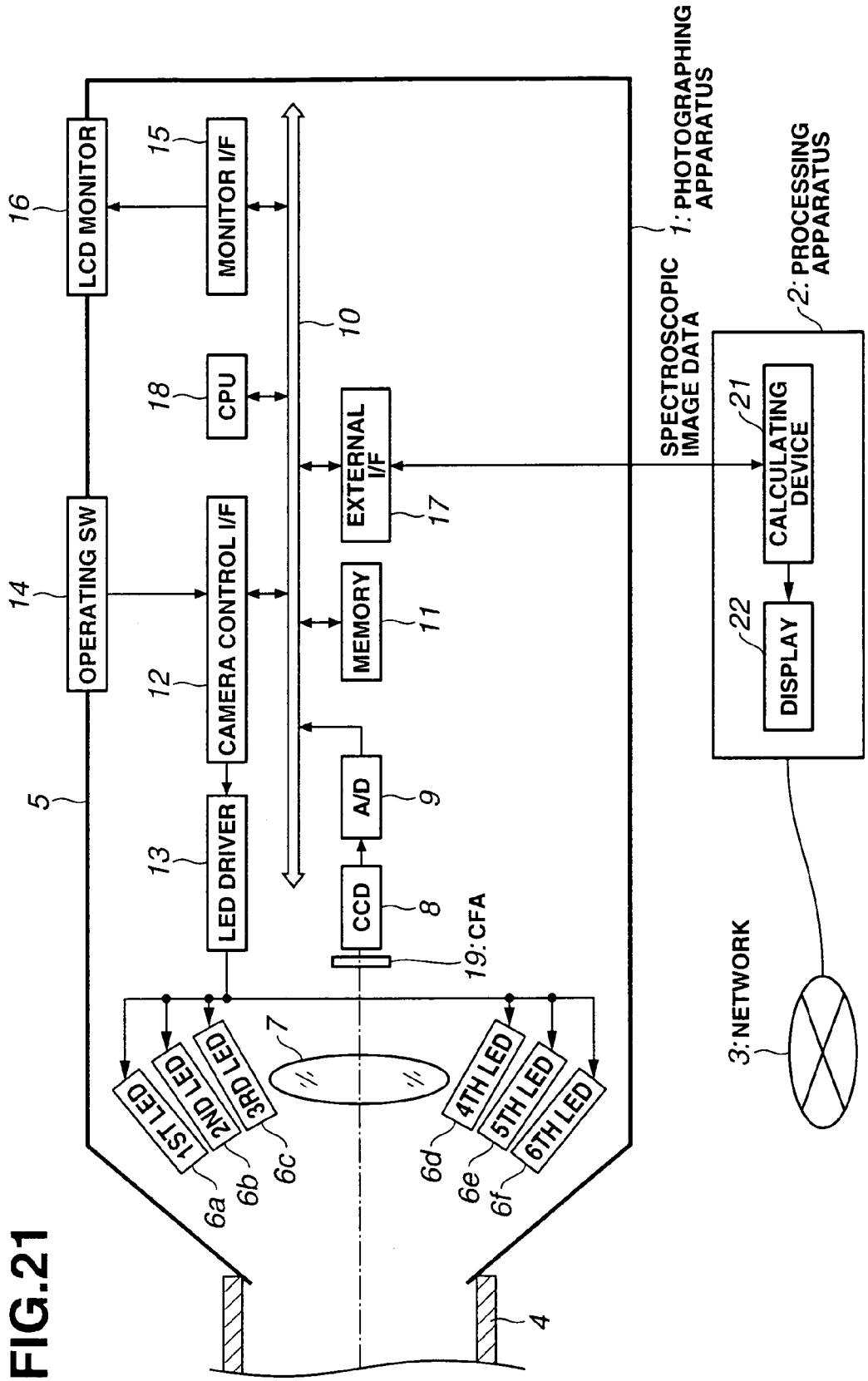
FIG. 21 is a block diagram showing the configuration of an image processing system according to the third embodiment of the present invention.
Figure 22:
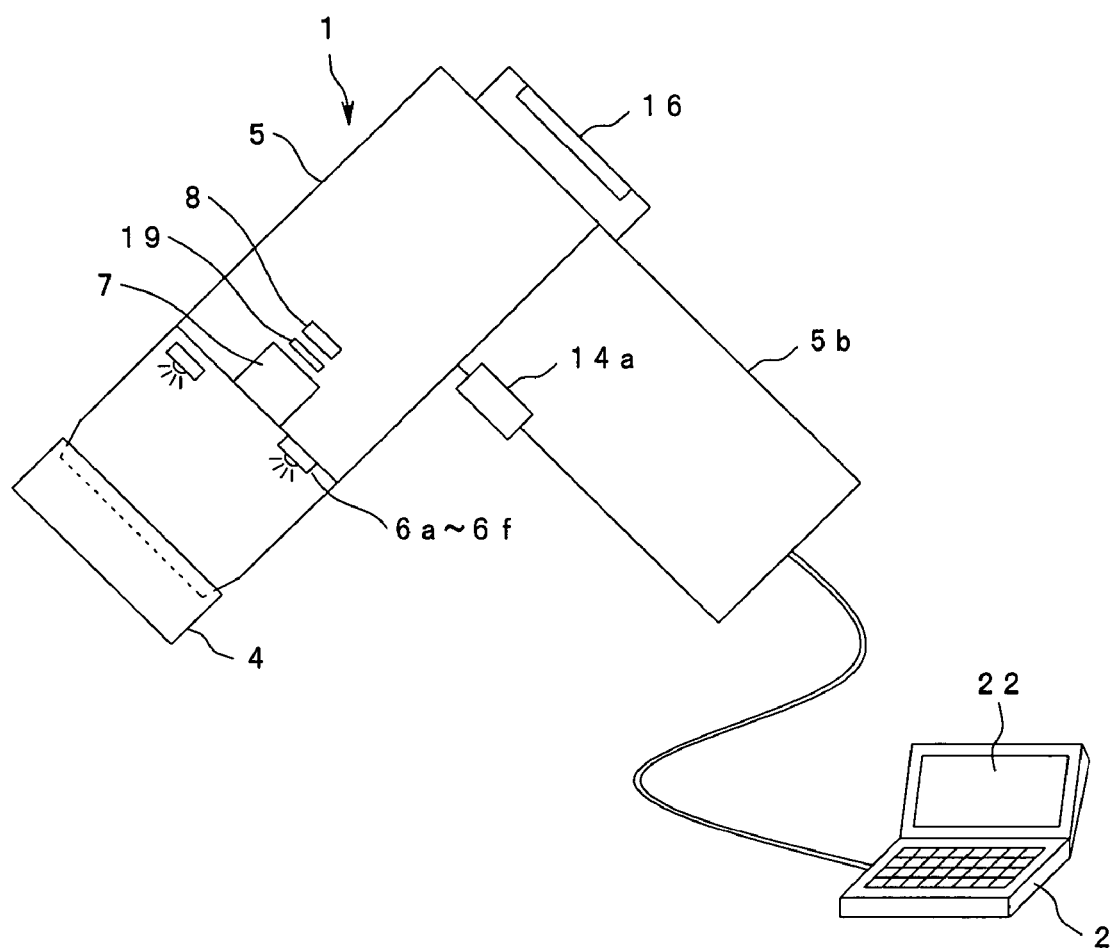
FIG. 22 is a diagram showing an example of a state of using the image processing system according to the third embodiment.

FIGS. 21 to 36 relate to the third embodiment of the present invention. FIG. 21 is a block diagram showing the configuration of an image processing system. FIG. 22 is a diagram showing an example of a state of using the image processing system. According to the third embodiment, the same components as those according to the first embodiment are designated by the same reference numerals and are not described. Mainly, only different portions are described.

The third embodiment uses the basic configuration according to the first embodiment. Further, according to the third embodiment, a 3-band color filter array is arranged onto the image pick-up surface of the CCD.

Referring to FIGS. 21 and 22, the photographing apparatus 1 comprises a 3-band (RGB) color filter array 19 (abbreviated to a CFA in the drawings) near the CCD 8 on the optical path on which the image pick-up optical system 7 forms the subject image, and a single-plate color image pick-up device is provided as the image pick-up device.

FIG. 23 is a graph showing the light-emitting spectrums of the first to sixth LEDs 6a to 6f and the spectroscopic sensitivity characteristics of the CCD 8, the spectroscopic sensitivity characteristics passing through the color filter array 19.

With respect to the light-emitting spectrums of the 6-primary-color LEDs shown by the curves fL1 to fL6 as shown according to the first embodiment, curves fSB, fSG, and fSR shown in FIG. 23 denote the total spectroscopic sensitivity characteristics which are obtained by the transmittance distribution of the color filter array 19 and the light-receiving sensitivity distribution of the CCD 8.

Among the curves fSB, fSG, and fSR, the curve fSB indicating a spectroscopic band area corresponding to a blue color filter includes the two curves fL1 and fL2, and receives the light emitted by the first LED 6a and the second LED 6b. The curve fSG indicating a spectroscopic band area corresponding to a green color filter includes the two curves fL3 and fL4, and receives the third LED 6c and the fourth LED 6d. The curve fSR indicating a spectroscopic band area corresponding to a red color filter includes the two curves fL5 and fL6, and receives the fifth LED 6e and the sixth LED 6f.

The total spectroscopic sensitivity characteristics are not necessarily independently separated and may be partly overlaid at the peripheral portion. Further, similarly to the first embodiment, the light-emitting spectrums of the first to sixth LEDs 6a to 6f may be partly overlaid. Of course, the number of LED types is not limited to six and a proper number of LEDs may be combined.

Next, the operation for capturing the image will be described.

Similarly to the first embodiment, in the image processing system the capturing mode of the monitoring image and the capturing mode of the spectroscopic image are switched to capture the image.

Figure 26:
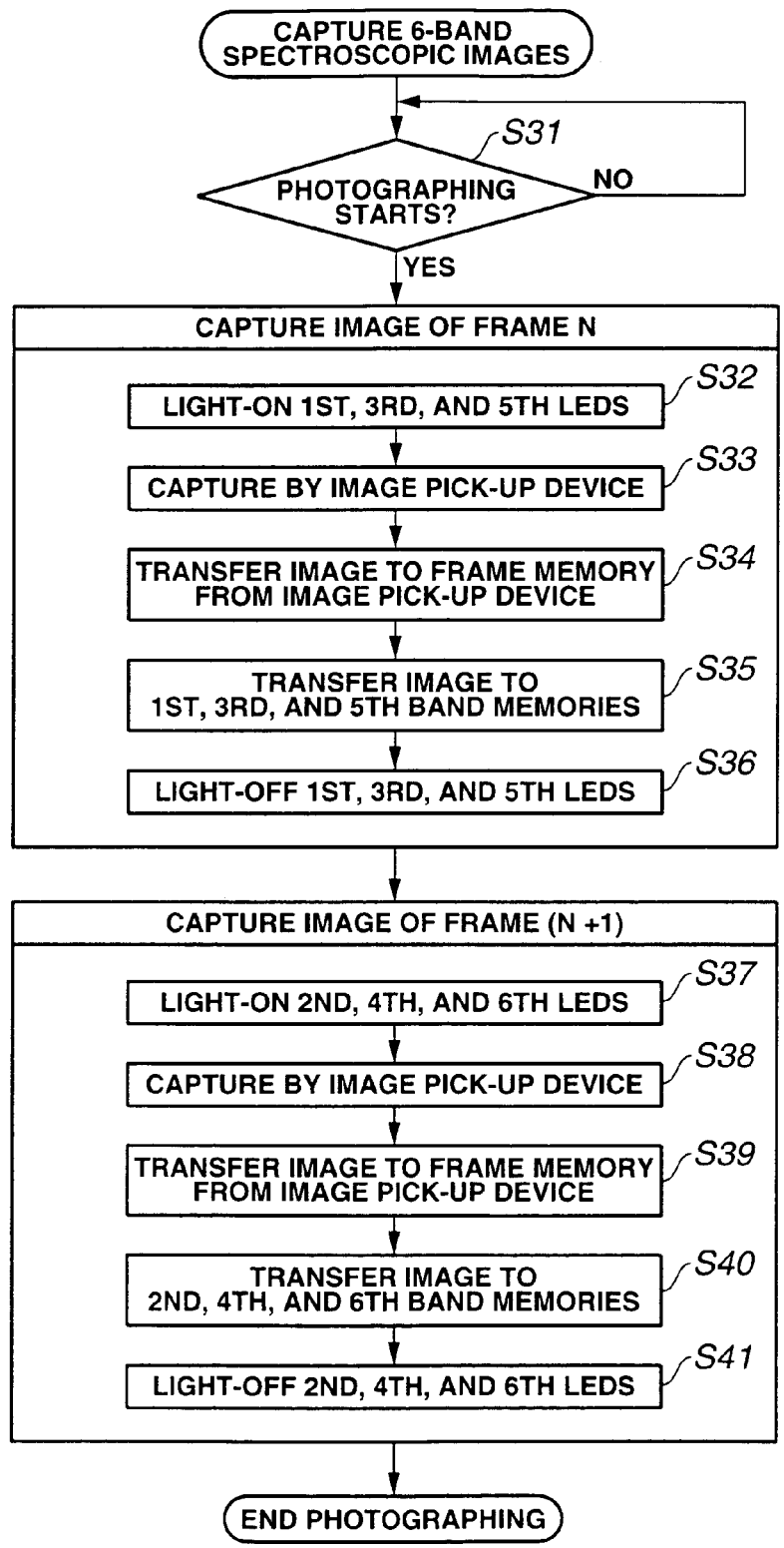
FIG. 26 is a flowchart showing the operations for light emission of LEDs and for image capturing by an image pick-up device, upon capturing the 6-band spectroscopic images according to the third embodiment.
Figure 27:
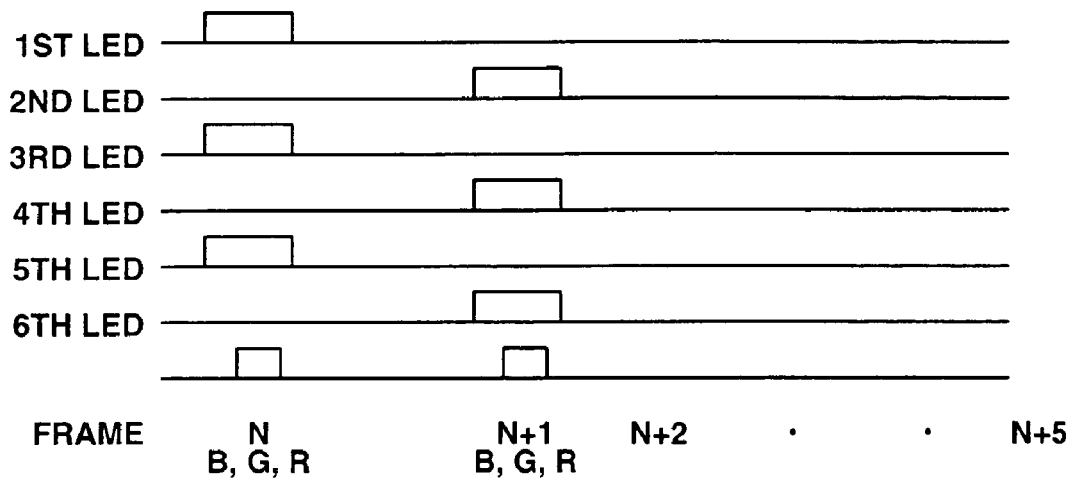
FIG. 27 is a timing chart showing states of the operations for light emission of the LEDs and for image capturing by the image pick-up device upon capturing the 6-band spectroscopic images according to the third embodiment.

The operation of the capturing mode of the spectroscopic image will be described with reference to FIGS. 24, 26, and 27. FIG. 24 is a graph showing the spectroscopic characteristics of the spectroscopic images of frames upon creating the 6-band spectroscopic images. FIG. 26 is a flowchart showing the operations for light emission of LEDs upon capturing the 6-band spectroscopic images and for image capturing by an image pick-up device. FIG. 27 is a timing chart showing states of the operations for light emission of the LEDs upon capturing the 6-band spectroscopic images and for image capturing by the image pick-up device.

As mentioned above according to the first embodiment, the photographing button 14a is pressed, thereby switching the mode to the capturing mode of the spectroscopic image. Then, it is determined whether or not the image pick-up operation of the spectroscopic image starts (step S31).

The image pick-up operation of the spectroscopic image starts, then, the image of the frame N is captured, and the image of a frame (N+1) is thereafter captured.

The capturing operation of the image of the frame N starts and then the first LED 6a, the third LED 6c, and the fifth LED 6e are simultaneously lit-on (refer to FIG. 24(A)) (step S32). After the light-on operation, the CCD 8 starts to pick-up the image (refer to FIG. 27) (step S33).

After the image pick-up operation of the CCD 8 ends, the image data is read from the CCD 8, is converted into the digital data by the A/D converter 9, and is stored in a predetermined storage area (frame memory) in the memory 11 via the bus 10 (step S34).

The image data stored in the frame memory is classified every primary color, and is stored in the predetermined storage area (first, third, and fifth memories) in the memory 11 (step S35).

Then, the first LED 6a, third LED 6c, and fifth LED 6e are lit-off (step S36) and thus the capturing operation of the images of the frame N ends.

The capturing operation of the image of the next frame (N+1) is basically similar to the capturing operation of the image of the frame N, only different in the lit-on LED and the memory area in which the picked-up image data is transferred.

That is, the second LED 6b, the fourth LED 6d, and the sixth LED 6f are simultaneously lit-on (refer to FIG. 24(B)) (step 37). After starting the light-on operation, the image pick-up operation of the CCD 8 starts (refer to FIG. 27) (step S38).

After the image pick-up operation of the CCD 8 ends, the image data is read from the CCD 8, is converted into the digital data by the A/D converter 9, and is stored in a predetermined storage area (frame memory) in the memory 11 via the bus 10 (step S39).

The image data stored in the frame memory is classified every primary color, and is stored in the predetermined storage area (second, fourth, and sixth memories) in the memory 11 (step S40).

Then, the second LED 6b, fourth LED 6d, and sixth LED 6f are lit-off (step S41) and thus the capturing operation of the images of the frame (N+1) ends.

Although not shown, the image capturing timing of the LEDs and the CCD is not limited to this and, identically, the LEDs may be lit-on after starting capturing the image by the image pick-up device and the operation for capturing the image by the image pick-up device may end after the light-off operation of the LED.

The images of the primary colors stored in the first to sixth memories in steps S35 to S40 are subjected to the interpolation in the photographing apparatus 1 or the processing apparatus 2 if necessary because of the lack of a pixel in accordance with the alignment of the primary colors in the color filter array 19.

The 6-band subject spectroscopic images stored in the memory 11 are sent to the processing apparatus 2 and are subjected to the color reproduction and image processing by a processing program. The processing result is displayed on the display 22 by another processing program or is transferred to the photographing apparatus 1 and is displayed on the LCD monitor 16.

Figure 28:
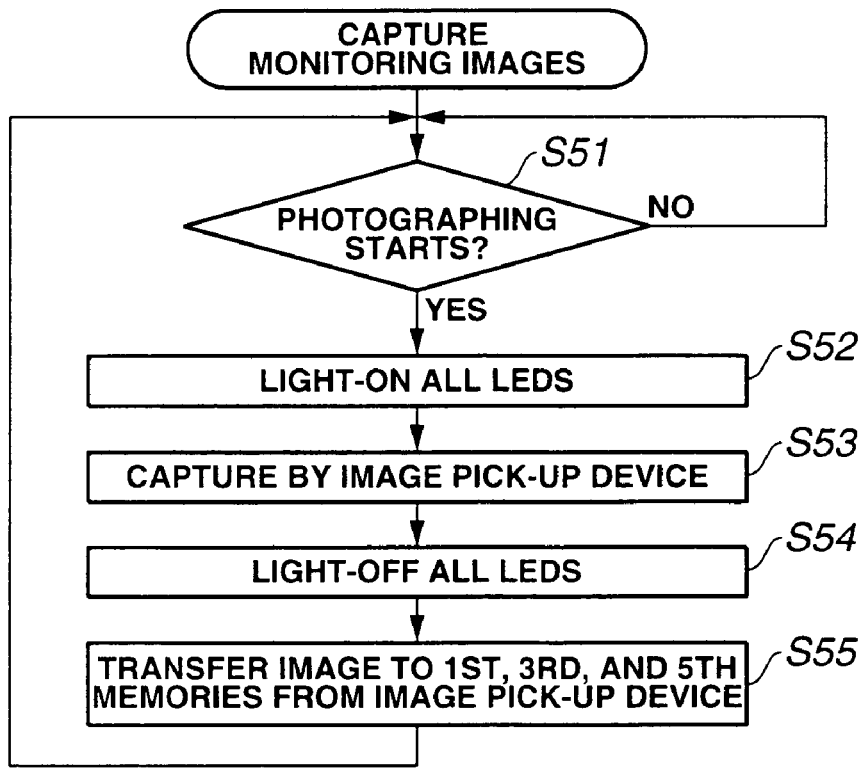
FIG. 28 is a flowchart showing the operations for light emission of the LEDs and for image capturing by the image pick-up device, upon capturing the monitoring image according to the third embodiment.
Figure 29:
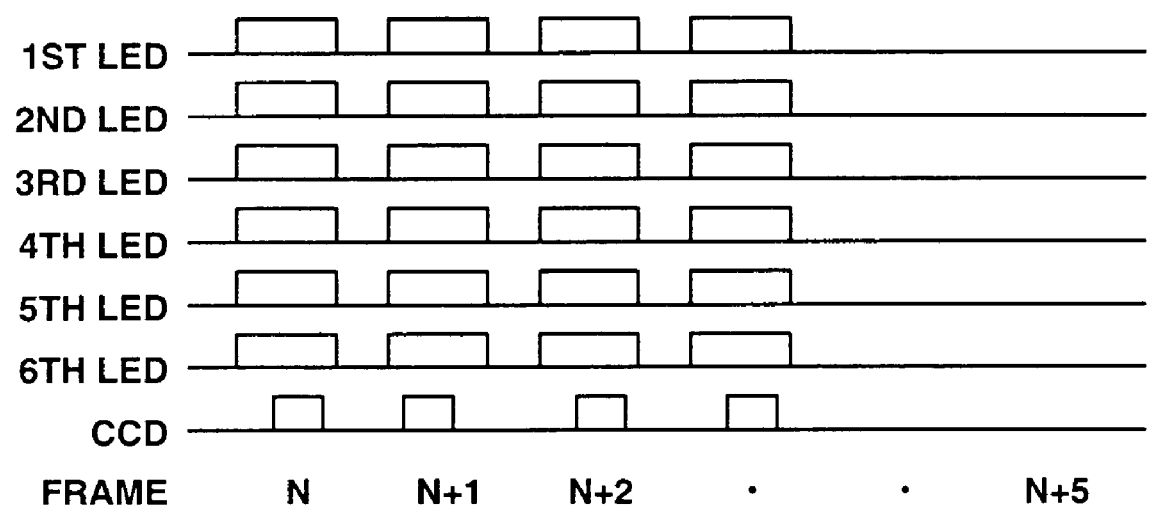
FIG. 29 is a timing chart showing states of the operations for light emission of the LEDs and for image capturing of the image pick-up device, upon capturing the monitoring image according to the third embodiment.

Next, a description is given of the operation of the capturing mode of the monitoring image with reference to FIGS. 25, 28, and 29. FIG. 25 is a graph showing the spectroscopic characteristics of the frames upon creating the monitoring image. FIG. 28 is a flowchart showing the operations for light emission of the LEDs upon capturing the monitoring image and for image capturing by the image pick-up device. FIG. 29 is a timing chart showing states of the operations or light emission of the LEDs upon capturing the monitoring image and for image capturing by the image pick-up device.

Similarly to the first and second embodiments, according to the third embodiment, the general RGB images are assumed and the primary colors for light emission are selected so that the first LED 6a and the second LED 6b correspond to the blue (B), the third LED 6c and the fourth LED 6d correspond to the green (G), and the fifth LED 6e and the sixth LED 6f correspond to the red (R).

The power switch is turned on, thereby setting the capturing mode of the monitoring image. Alternatively, the capturing mode of the spectroscopic image ends, thereby returning the mode to the capturing mode of the monitoring image. Thus, the start for picking-up the monitoring image is waited (step S51).

Promptly, the image pick-up operation starts and all the first to sixth LEDs 6a to 6f are lit-on (refer to FIG. 25) (step S52). After starting the light-on operation of all the first to sixth LEDs 6a to 6f, the image pick-up operation by the CCD 8 starts (refer to FIG. 29) (step S53).

After ending the image pick-up operation by the CCD 8, then, all the first to sixth LEDs 6a to 6f are lit-off (step S54). The image data is read from the CCD 8, is converted into the digital data by the A/D converter 9, and is stored in the predetermined storage areas (first, third, and fifth memories) in the memory 11 via the bus 10 (step S55).

During setting the capturing mode of the monitoring image, the processing returns to step S51, the above-mentioned operations are repeated, and thus the moving image is captured.

The thus-obtained image is converted into the monitoring image data, and is displayed on the LCD monitor 16 via the monitor I/F 15. In this case, the monitoring image is displayed on the display 22 in the processing apparatus 2.

In the timing chart shown in FIG. 29, the power consumption is reduced by lighting-on and lighting-off the first to sixth LEDs 6a to 6f every image pick-up operation performed by the CCD 8. During setting the capturing mode of the monitoring image, the first to sixth LEDs 6a to 6f may be continuously lit-on.

Although not shown, the image capturing timing of the LEDs and the CCD is not limited to this and, identically, the LEDs may be lit-on after starting capturing the image by the image pick-up device and the operation for capturing the image by the image pick-up device may end after the light-off operation of the LEDs.

According to another method for capturing the monitoring image, the continuous capturing mode of the 6-band spectroscopic images enables the creation of the monitoring image by addition of memories of the first and second bands of the 6-band spectroscopic images, addition of memories of the third and fourth bands, and addition of memories of the fifth and sixth bands. In this case, the monitoring image is created only by addition of memories without changing the algorithm of the photographing portion. This is advantageous as a monitoring method upon measuring the continuous spectroscopic images.

Figure 30:
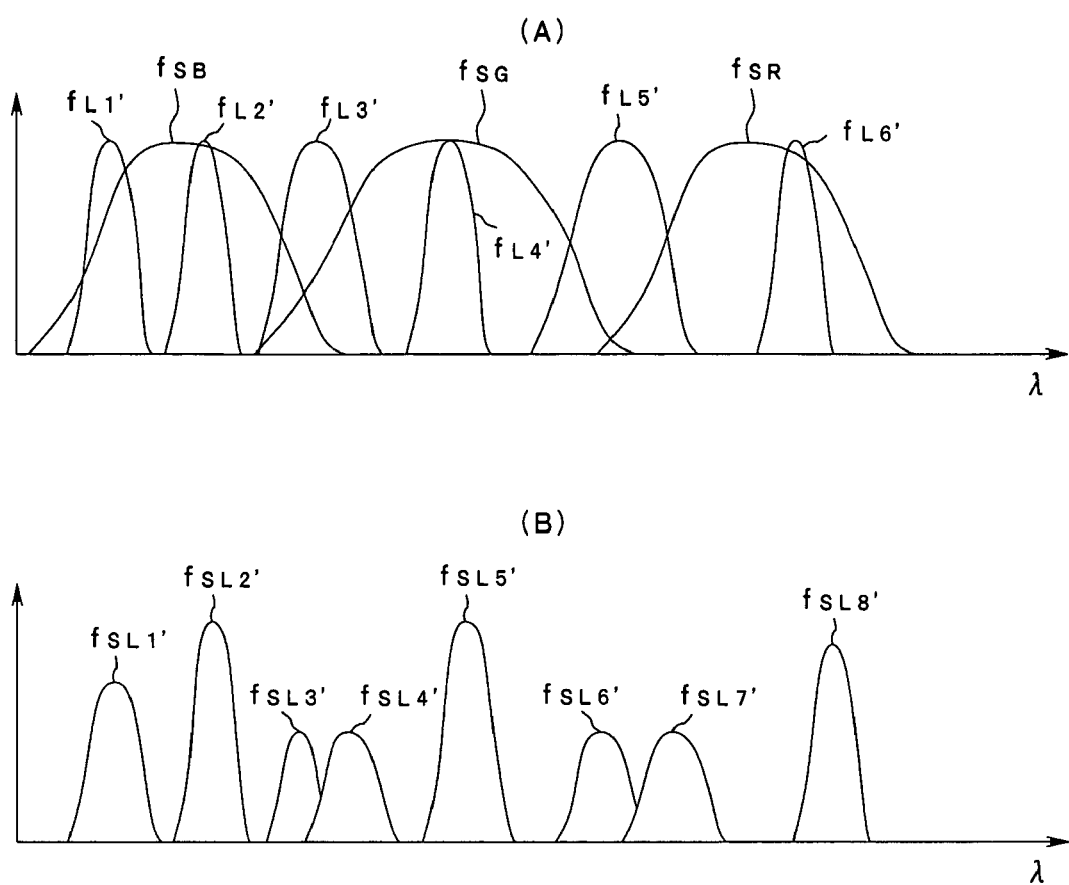
FIG. 30 is a graph showing light-emitting spectrums of the LEDs and the spectroscopic sensitivity characteristics of the CCD through a color filter array, upon creating 8-band spectroscopic images according to the third embodiment.

Next, FIGS. 30 to 36 relate to modifications of the third embodiment. FIG. 30 is a graph showing the light-emitting spectrums of the LEDs and the spectroscopic sensitivity characteristics of the CCD passed through a color filter array, upon creating the 8-band spectroscopic images.

According to one modification of the third embodiment, the LED is arranged with the light-emitting spectroscopic characteristics between the RGB bands detected by the CCD 8 via the color filter array 19. Thus, although the LEDs only emit the light of the six primary colors (6 bands), it is detected that the 8 band signals are outputted.

Referring to FIG. 30(A), with respect to the curves fSB, fSG, and fSR indicating the total spectroscopic sensitivity characteristics obtained by the transmittance distribution of the color filter array 19 and the light-receiving sensitivity distribution of the CCD 8, the spectroscopic characteristics of the light emission of the first to sixth LEDs 6a to 6f are as follows (shown by curves fL1' to fL6').

The curve fSB indicating the spectroscopic band area corresponding to the blue color filter includes the two curves fL1' and fL2', and further includes a part of the curve fL3'.

The curve fSG indicating the spectroscopic band area corresponding to the green color filter includes the curve fL4', and further includes a part of the curve fL3' and a part of the fL5'.

The curve fSR indicating the spectroscopic band area corresponding to the red color filter includes the curve fL6' and further includes a part of the curve fL5'.

As a consequence, the spectroscopic characteristics (curve fL3') of the light emission from the third LED 6c exist between the band through the blue color filter and the band through the green color filter. The spectroscopic characteristics (curve fL5') of the light emission from the fifth LED 6e exist between the band through the green color filter and the band through the red color filter.

With the above-mentioned configuration, referring to FIG. 30(B), the total spectroscopic sensitivity characteristics upon receiving the light emitted from the first to sixth LEDs 6a to 6f by the CCD 8 via the input button unit 19 is 8 bands including a curve fSL1' (formed by the curves fL1' and fSB), a curve fSL2' (formed by the curves fL2' and fSB), a curve fSL3' (formed by the curves fL3' and the curve fSB), a curve fSL4' (formed by the curves fL3' and fSG), a curve fSL5' (formed by the curves fL4' and fSG), a curve fSL6, (formed by the curves fL5' and fSG), a curve fSL7' (formed by the curves fL5' and fSR), and a curve fSL8' (formed by the curves fL6' and fSR).

Figure 32:
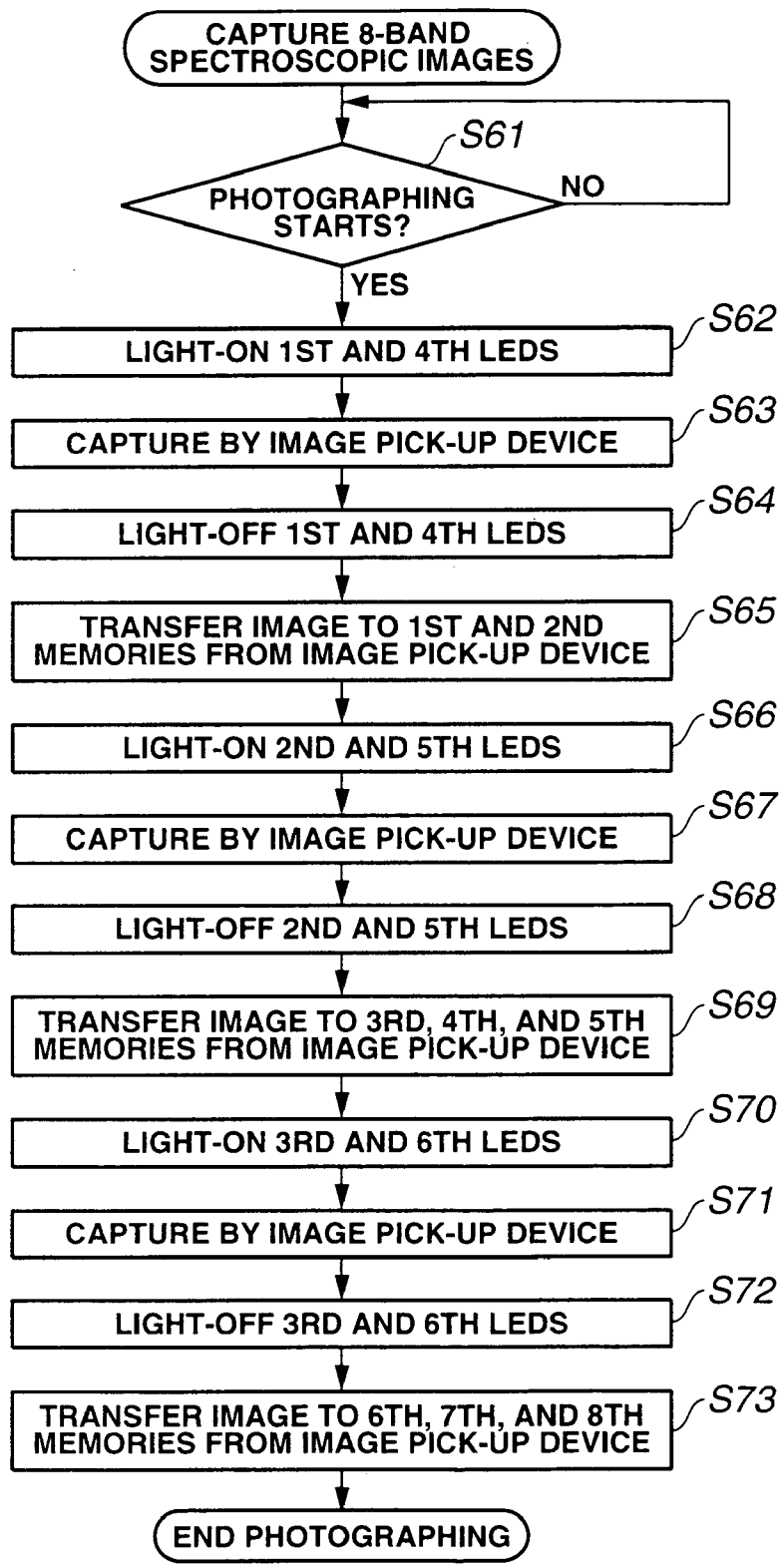
FIG. 32 is a flowchart showing the operation for light emission of the LEDs and for image capturing by the image pick-up device, upon capturing the 8-band spectroscopic images according to the third embodiment.
Figure 33:
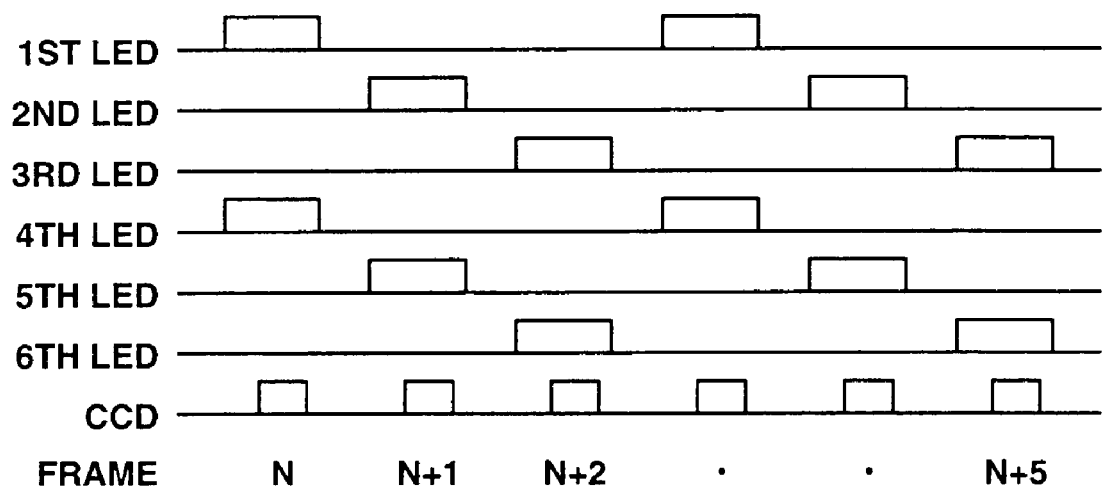
FIG. 33 is a timing chart showing a state of the operations for light emission of the LEDs and for image capturing by the image pick-up device, upon capturing the 8-band spectroscopic images according to the third embodiment.

Next, the operation for capturing the 8-band spectroscopic image will be described with reference to FIGS. 31 to 33. FIG. 31 is a graph showing the spectroscopic characteristics of the spectroscopic images of frames, upon creating the 8-band spectroscopic images. FIG. 32 is a flowchart showing the operation for light emission of the LEDs and for image capturing by the image pick-up device, upon capturing the 8-band spectroscopic images. FIG. 33 is a timing chart showing a state of the operations for light emission of the LEDs and for image capturing by the image pick-up device, upon capturing the 8-band spectroscopic images.

According to another modification of the third embodiment, the storage areas including first to eighth memories are arranged in the photographing apparatus 1 to pick-up the 8-band spectroscopic images.

The photographing button 14a is pressed and thus the mode is switched to the capturing mode of the spectroscopic image. Then, it is determined whether or not the image pick-up operation of the spectroscopic image starts (step S61).

The image pick-up operation of the spectroscopic image starts. Then, referring to FIG. 31(A), the operation for capturing the image of the frame N starts. The first LED 6a and the fourth LED 6d are simultaneously lit-on (step S62). After starting the light-on operation, the image pick-up operation of the CCD 8 starts (refer to FIG. 33) (step S63).

After the image pick-up operation of the CCD 8 ends, the first LED 6a and fourth LED 6d are lit-off (step S64). The image data is read from the CCD 8, is converted into the digital data by the A/D converter 9, and is stored in predetermined storage areas (first and second memories) in the memory 11 via the bus 10 (step S65). Thus, the operation for capturing the image of the frame N ends (operation for capturing the image of the 2-band subject spectroscopic images ends).

Next, referring to FIG. 31(B), the operation for capturing the image of the frame (N+1) starts, and the second LED 6b and the fifth LED 6e are simultaneously lit-on (step S66). After starting the light-on operation, the image pick-up operation by the CCD 8 starts (refer to FIG. 33) (step S67).

After the image pick-up operation of the CCD 8 ends, the second LED 6b and fifth LED 6e are lit-off (step S68). The image data is read from the CCD 8, and is stored in predetermined storage areas (third, fourth, and fifth memories) in the memory 11 (step S69). Thus, the operation for capturing the image of the frame (N+1) ends (operation for capturing the image of the 3-band subject spectroscopic images ends).

Further, referring to FIG. 31(C), the operation for capturing the image of the frame (N+2) starts, and the third LED 6c and the sixth LED 6f are simultaneously lit-on (step S70). After starting the light-on operation, the image pick-up operation by the CCD 8 starts (refer to FIG. 33) (step S71).

After the image pick-up operation of the CCD 8 ends, the third LED 6c and sixth LED 6f are lit-off (step S72). The image data is read from the CCD 8, and is stored in predetermined storage areas (sixth, seventh, and eighth memories) in the memory 11 (step S73). Thus, the operation for capturing the image of the frame (N+2) ends (operation for capturing the image of the 3-band subject spectroscopic images ends).

Upon continuously capturing the spectroscopic images like the moving image, the operation from the frame N to the frame (N+2) is repeated.

Although not shown, the image capturing timings of the LEDs and the CCD are not limited to the foregoing. Identically, the LEDs are lit-on after starting capturing the image by the image pick-up device and the image capturing by the image pick-up device ends after the light-off operation of the LEDs.

The 6-band subject spectroscopic images stored in the memory 11 are sent to the processing apparatus 2 and are subjected to the color reproduction and image processing by a processing program. The processing result is displayed on the display 22 by another processing program or is transferred to the photographing apparatus 1 and is displayed on the LCD monitor 16.

Figure 34:
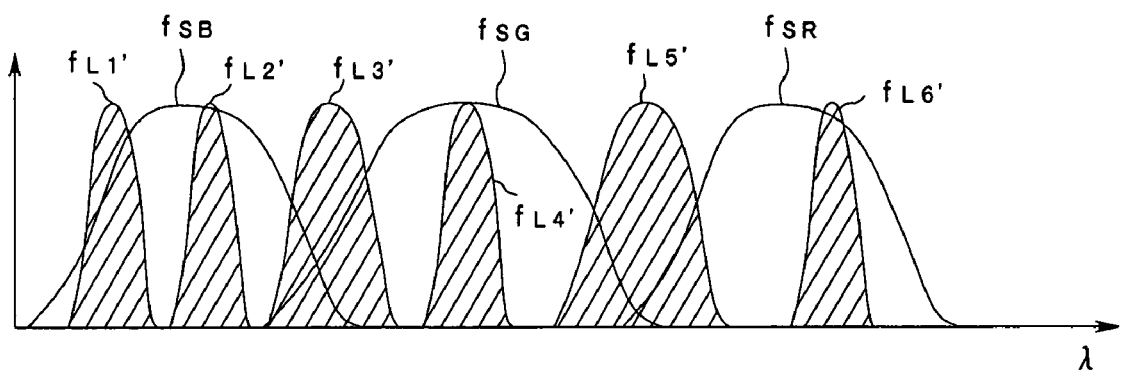
FIG. 34 is a graph showing the spectroscopic characteristics of the spectroscopic images every frame, upon creating the monitoring image according to the third embodiment.
Figure 35:
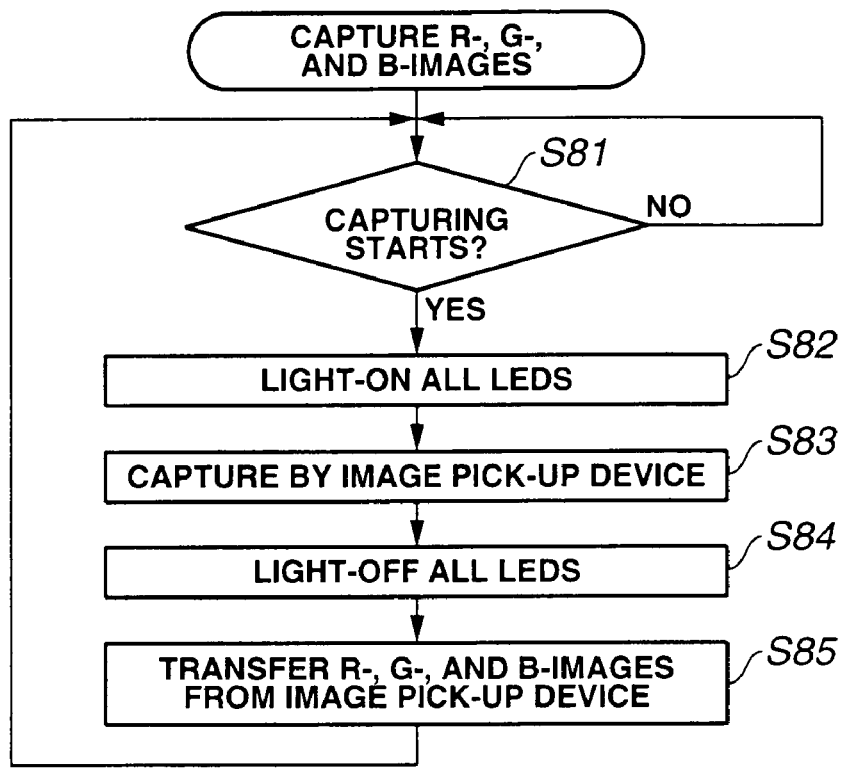
FIG. 35 is a flowchart showing the operations for light emission of the LEDs and for image capturing by the image pick-up device, upon capturing the monitoring image according to the third embodiment.
Figure 36:
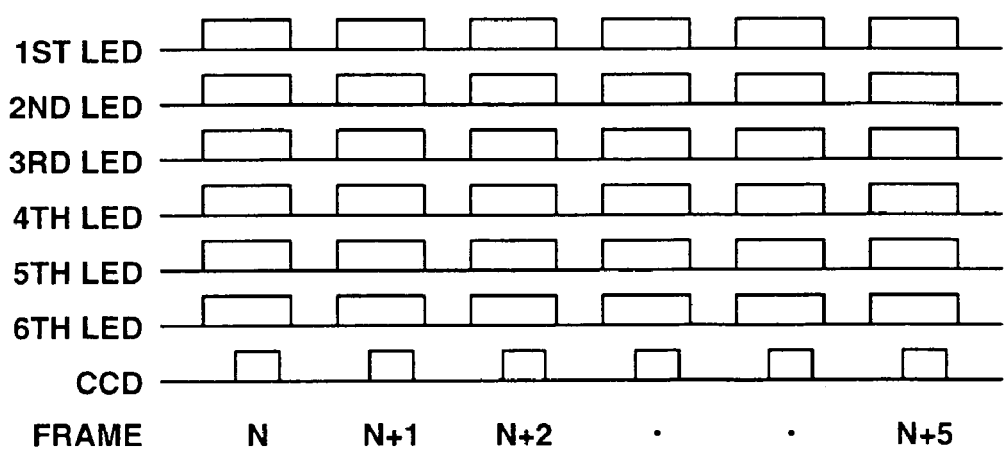
FIG. 36 is a timing cart showing states of the operations for light emission of the LEDs and for image capturing by the image pick-up device, upon capturing the monitoring image according to the third embodiment.

Next, a description is given of the operation of the capturing mode of the monitoring image with reference to FIGS. 34 to 36. FIG. 34 is a graph showing the spectroscopic characteristics of the spectroscopic images of the frames, upon creating the monitoring image. FIG. 35 is a flowchart showing the operations for light emission of the LEDs and for image capturing by the image pick-up device, upon capturing the monitoring image. FIG. 36 is a timing chart showing the state of the operations for light emission of the LEDs and for image capturing by the image pick-up device, upon capturing the monitoring image.

The power switch is turned on, thereby setting the capturing mode of the monitoring image. Alternatively, the capturing mode of the spectroscopic image ends, thereby returning the mode to the capturing mode of the monitoring image. Thus, the start for picking-up the monitoring image is waited (step S81).

Promptly, the image pick-up operation starts and all the first to sixth LEDs 6a to 6f are lit-on (refer to FIG. 34) (step S82). After starting the light-on operation of all the first to sixth LEDs 6*a* to 6*f*, the image pick-up operation by the CCD 8 starts (refer to FIG. 36) (step S83).

After ending the image pick-up operation by the CCD 8, then, all the first to sixth LEDs 6*a* to 6*f* are lit-off (step S84). The image data is read from the CCD 8, is converted into the digital data by the A/D converter 9, and is stored in a predetermined storage area in the memory 11 via the bus 10 (step S85).

Herein, the first to sixth LEDs 6*a* to 6*f* are lit-on and are lit-off every image pick-up operation by the CCD 8, thereby reducing the power consumption. However, similarly to the description with reference to FIG. 29, the first to sixth LEDs 6*a* to 6*f* may be continuously lit-on during setting the capturing mode of the monitoring image.

Although not shown, the image capturing timings of the LEDs and the CCD are not limited to the foregoing. Identically, the LEDs are lit-on after starting capturing the image by the image pick-up device and the image capturing by the image pick-up device ends after the light-off operation of the LEDs.

Until resetting the capturing mode of the monitoring image, the processing returns to step S81, then the above-mentioned operation is repeated, and the image data for moving image is continuously captured.

The captured images are converted into the monitoring image data, and are displayed on the LCD monitor 16 via the monitor I/F 15. In this case, by the setting, the monitoring image is displayed on the display 22 of the processing apparatus 2.

As mentioned above using an example, the image pick-up device is a simple-plate image pick-up device which is formed by the combination with the 3-band color filter array. However, the present invention is not limited to this and may be a three-plate 3-band image pick-up device comprising a spectroscopic unit, such as a spectroscopic mirror or spectroscopic prism, which performs the spectroscopy of the incident light into a plurality of wavelengths, and a plurality of image pick-up devices which pick-up the image of the light of the plurality of wavelength bands which are divided by the spectroscopic unit. Alternatively, the image pick-up devices may be a two-plate image pick-up device. Further, the color filter is not limited to a primary color system filter of three RGB bands and may be a complementary color system filter.

The 8-band subject spectroscopic image data is captured from the LEDs of the 6-band light-emitting spectrums. However, the present invention is not limited to this. Arbitrary subject spectroscopic image data may be captured by the combination. For example, the light source may be only the third LED and the fifth LED, namely, 2-band light source. In the case of the light source having the 2 bands, as shown by the curves fSL3', fSL4', fSL6' and fSL7', the 4-band subject spectroscopic images are captured. In addition, the light source may be used by various combination.

According to the third embodiment, the same advantages as those first and second embodiments are obtained. Further, the use of the color image pick-up device reduces the number of image pick-up times necessary for capturing the subject spectroscopic image, and the moving image is easily color-reproduced at the high fidelity level.

Further, the light-emitting spectrums of the LEDs exist over the spectroscopic sensitivity distributions of the light received by the color image pick-up device. Thus, the 8-band subject spectroscopic image data is captured by using the LEDs of the 6-band light-emitting spectrum.

Figure 37:
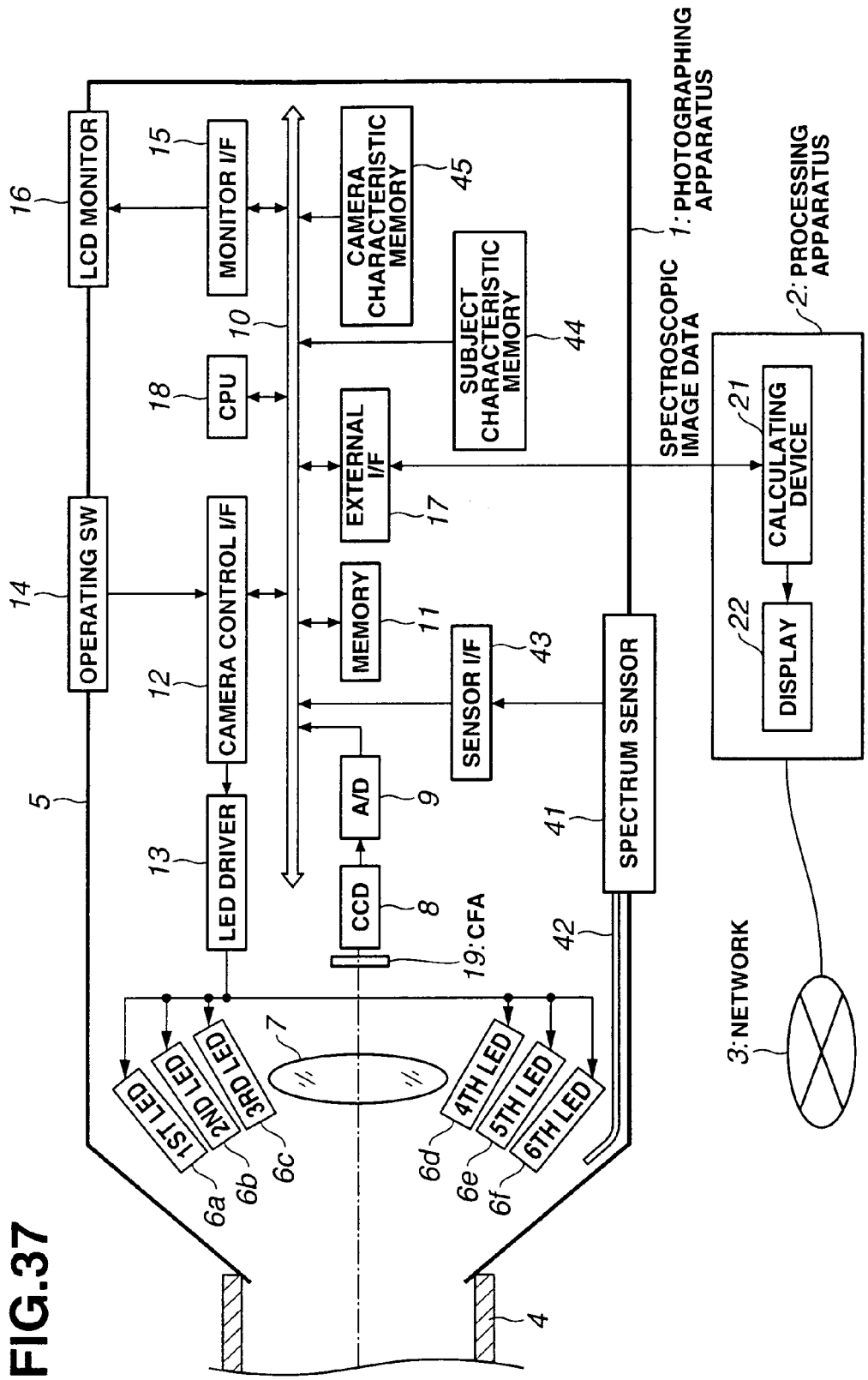
FIG. 37 is a block diagram showing the configuration of an image processing system according to the fourth embodiment of the present invention.

FIGS. 37 to 42 relate to the fourth embodiment of the present invention. FIG. 37 is a block diagram showing the configuration of an image processing system. According to the fourth embodiment, the same components as those according to the first to third embodiments are designated by the same reference numerals, a description thereof is omitted, and mainly different portions are described.

The fourth embodiment uses the basic configuration according to the third embodiment. Further, according to the fourth embodiment, the image processing system comprises a spectrum sensor.

Referring to FIG. 37, the photographing apparatus 1 in the image processing system comprises: a spectrum sensor 41 which senses the light spectrum distribution; a probe 42 which guides the sensed light to the spectrum sensor 41; a sensor I/F 43 which converts an output from the spectrum sensor 41 into a digital signal, processes it, and outputs it; a subject characteristic memory 44 which stores the subject characteristic; and a camera characteristic memory 45 which stores camera characteristic, in addition to the configuration according to the third embodiment shown in FIG. 21.

The spectrum sensor 41 senses only the spectrum, not capturing the light as the image, different from the configuration for capturing the 6-band spectroscopic image by the CCD 8 with the first to sixth LEDs 6*a* to 6*f*.

The spectrum sensor 41 covers the entire range of the visible light serving as the light sensing range (380 nm to 800 nm), sensors the spectrum by a grating method with a resolution of 5 nm. Thus, the specific spectrum data can be captured. Although the grating-method spectrum sensor is used as an example, the spectrum sensor 41 may be another.

The probe 42 uses a flexible optical fiber (or optical fiber bundle). However, the probe 42 is not limited to this and any probe for guiding the sensed light can be widely used.

With the above-mentioned configuration, the optical spectrum can be sensed by sensing the light from the subject. In the meantime, a standard white board is used in place of the subject, thereby measuring the spectrum characteristic of the illuminating light.

Specifically, external illuminating light is shielded by using the abutting portion 4 or the like and the spectrum is sensed by sequentially emitting the light of the first to sixth LEDs 6*a* to 6*f*. Thus, the spectrum characteristics of the first to sixth LEDs 6*a* to 6*f* are estimated. The degradation of the light-emitting device and the change in spectrum characteristics due to the evironmental change of the temperature are sensed. Further, since the profile of the illuminating spectrum which reflects the characteristic change, the color is accurately reproduced at the high fidelity level.

Further, the ambient illuminating light is sensed and the spectrum characteristics of the exterior lighting are measured.

Figure 38:
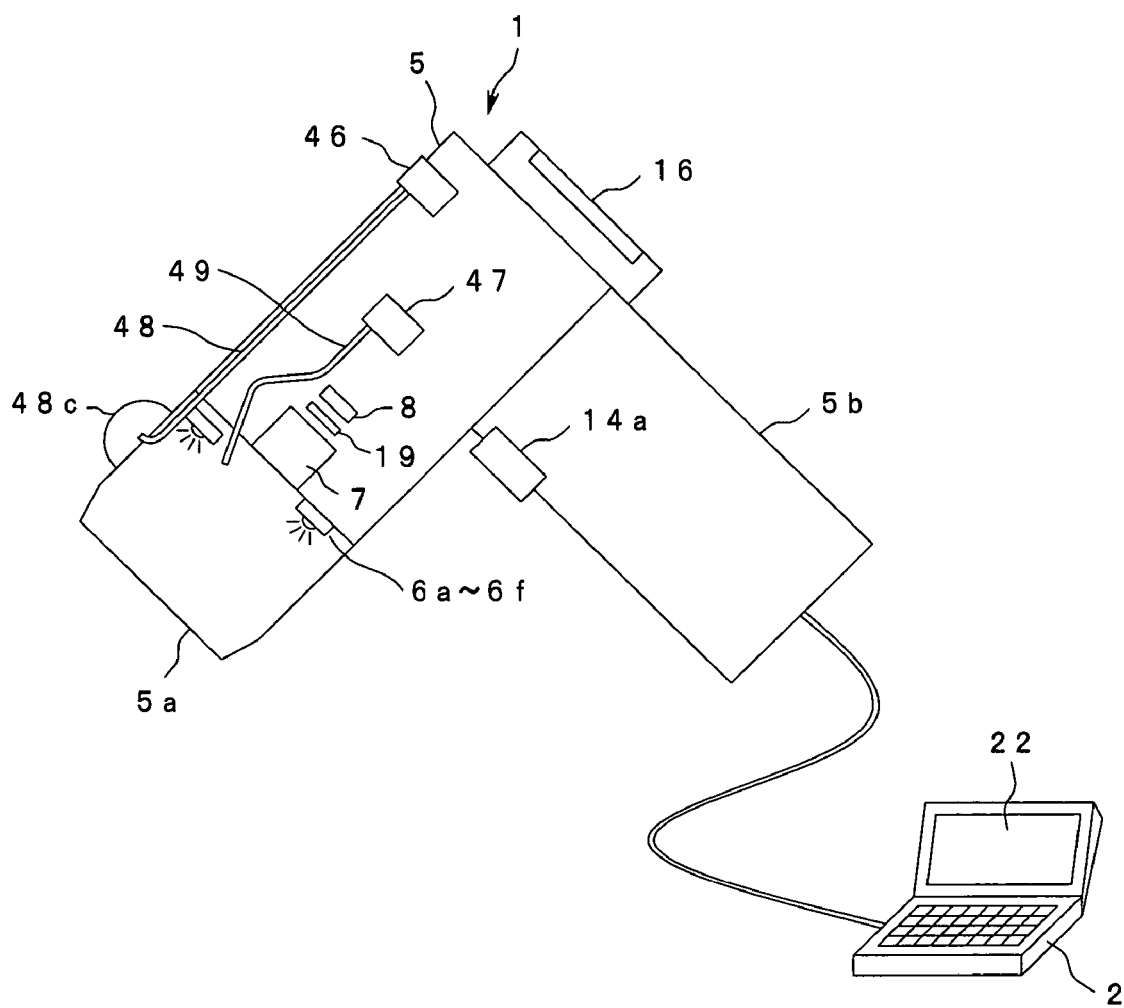
FIG. 38 is a diagram showing an example state of using the image processing system comprising a plurality of spectrum sensors according to the fourth embodiment.

Next, FIG. 38 is a diagram showing one example of a state of using the image processing system having a plurality of spectrum sensors.

Referring to FIG. 38, the specific arrangement of the spectrum sensor is shown. Here, two spectrum sensors, namely, a first spectrum sensor 47 and a second spectrum sensor 46 are used.

The first spectrum sensor 47 is arranged to sense the spectroscopic spectrum of the subject portion, and the tip of an optical fiber 49 serving as a probe is arranged at the incident position of the subject light via the projecting port 5*a* of the casing 5, near the first to sixth LEDs 6*a* to 6*f*.

As mentioned above, the first spectrum sensor 47 has the standard white board arranged, in place of the subject, thereby being used to sense the illuminating spectrums of the first to sixth LEDs 6*a* to 6*f*. Further, the tip of the first spectrum sensor 47 has a lens or the like as will be described later, thereby directly capturing spectroscopic reflecting spectrums of a spot (specific portion) of the subject.

Thus, the spectrum data such as the painting color of a vehicle, painting color of the building, spectroscopic characteristics of food, or dyeing of the cloths is directly obtained and is used as data for examination and confirmation.

The second spectrum sensor 46 is arranged to sense the illuminating light spectrum of the environment under which the subject is placed. The tip of an optical fiber 48 as a probe is exposed to the outer surface of the casing 5. Further, an integrating sphere 48c which is white and semi-transparent covers the tip of the optical fiber 48. The use of the second spectrum sensor 46 enables the capturing of the illuminating spectrums upon photographing the subject apart from the photographing apparatus 1 only with sunlight or room light. Thus, simultaneously with the photographing operation of the subject image, the profile of the illuminating spectrum of the ambient illuminating light in this case can be created. Therefore, if the ambient illuminating light changes, in accordance therewith, the color is automatically reproduced at the high fidelity level in real time.

Further, the spectrum of ambient light of the photographing apparatus 1 is sensed and is compared with the spectrums of the LEDs included in the photographing apparatus 1. Thus, the ambient light and the LED light are adaptively switched for the image pick-up operation. For example, the ambient light is used upon picking-up the moving images of RGB. In this case, the power consumption is reduced by not emitting the light of the LED in the photographing apparatus 1.

Figure 39:
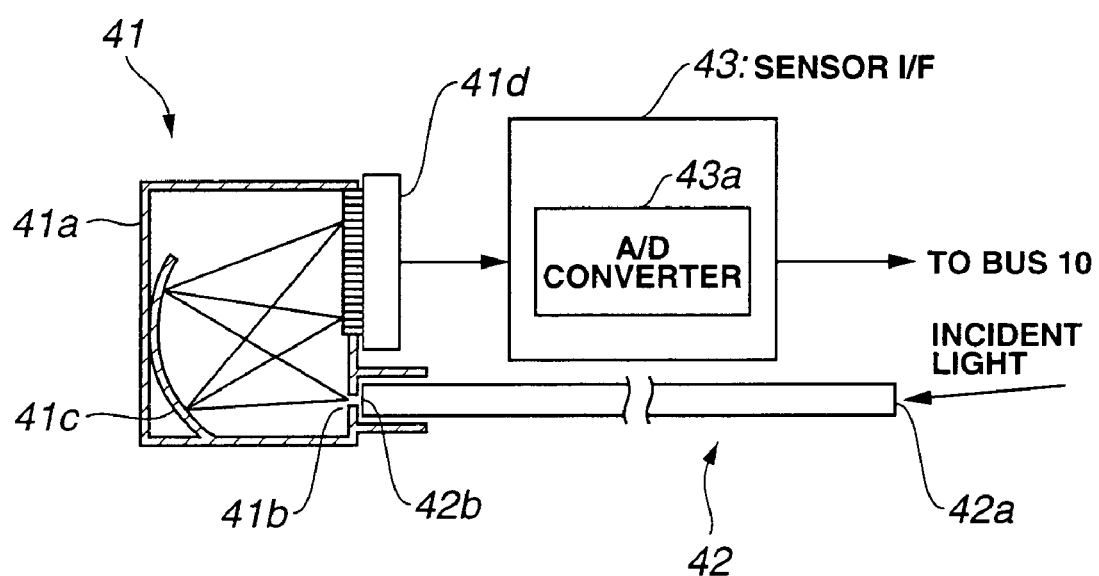
FIG. 39 is a sectional view showing an example configuration of the spectrum sensor according to the fourth embodiment.

FIG. 39 is a sectional view showing an example configuration of the spectrum sensor 41.

In the probe 42, the light is incident on an incident end 42a, and the light is outputted from an output end 42b.

The spectrum sensor 41 comprises: a box 41a; an incident-light slit 41b which is arranged as an opening at one end of the box 41a and on which the light is outputted from the output end 42b of the probe 42 serving as slit light; a grating 41c which is arranged in the box 41a, performs the stereoscopy of the slit light incident from the incident-light slit 41b in accordance with the wavelength, and reflects in the different directions and collects the light; and a photodiode array 41d which is attached to the box 41a, receives the light collected at positions varied depending on the wavelengths by the grating 41c, and outputs a signal in accordance with the strength of the received light.

Thus, the photodiode array 41d photoelectrically converts the light with the wavelengths varied depending on the light receiving positions, and outputs the signal in accordance with the strength.

The sensor 43 comprises an A/D converter 43a which converts an analog signal outputted from the photodiode array 41d into a digital signal. The digital signal after the conversion is outputted to the CPU 18 or the like via the bus 10. The CPU 18 receives the digital signal as spectrum information indicating the strength of the wavelength, and analyzes the information.

Figure 40:
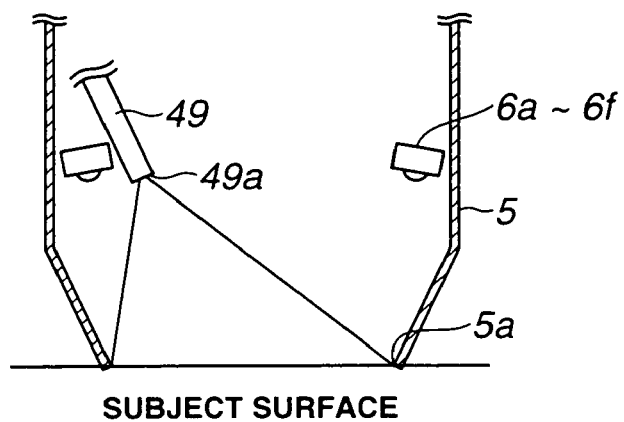
FIG. 40 is a sectional view showing a state of an incident end of an optical fiber connected to the spectrum sensor according to the fourth embodiment.

FIG. 40 is a sectional view showing a state of an incident end 49a of the optical fiber 49 connected to the first spectrum sensor 47. Referring to FIG. 40, the image pick-up optical system 7 and the like are not shown.

The light from an angle range is incident on the incident end 49a of the optical fiber 49. In the example shown in FIG. 40, the reflecting light from the subject surface serving as the photographing target, incident via the projecting port 5a of the casing 5, reaches the incident end 49a.

With the configuration shown in FIG. 40, the standard white board is used as the subject, the spectrums of the LED illumination are sensed and information on the color change due to the aging change is obtained.

Figure 41:
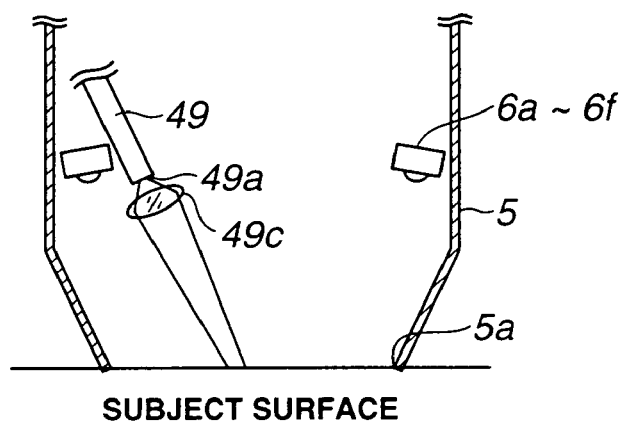
FIG. 41 is a sectional view showing an example configuration for arranging an optical system for sensor near the incident end of the optical fiber connected to the spectrum sensor according to the fourth embodiment.

FIG. 41 is a sectional view showing an example configuration of arranging an optical system 49c for sensor near the incident end 49a of the optical fiber 49 connected to the spectrum sensor 47. Referring to FIG. 41, the image pick-up optical system 7 and the like are not shown.

Referring to FIG. 41, the optical system 49c for sensor comprising a lens and the like are arranged to the incident end 49a of the optical fiber 49 connected to the first spectrum sensor 47. Therefore, beams incident on the incident end 49a are limited to the light from a range of the subject. As mentioned above, the spectrum at the specific position of the subject is measured with the resolution of the high wavelength.

Figure 42:
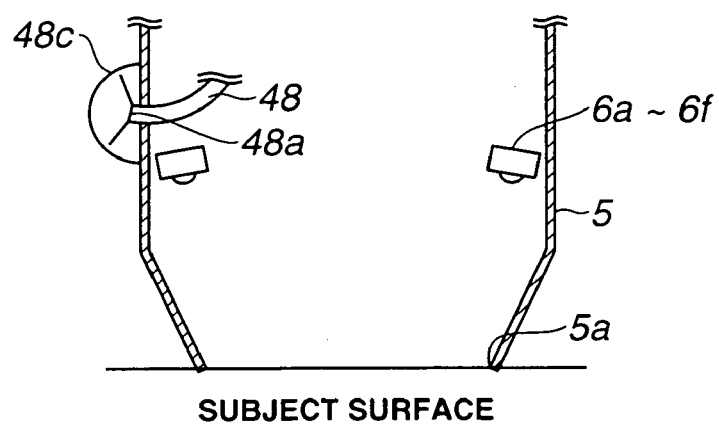
FIG. 42 is a sectional view showing a state of the incident end of the optical fiber connected to the spectrum sensor arranged for obtaining ambient light according to the fourth embodiment.

FIG. 42 is a sectional view showing a state of an incident end 48a of the optical fiber 48 connected to the second spectrum sensor 46 arranged for capturing the ambient light. Referring to FIG. 42, the image pick-up optical system 7 and the like are not shown.

As mentioned above, the incident end 48a of the optical fiber 48 for input is exposed to the outer surface of the casing 5 and has the integrating sphere 48c which is white and is semi-transparent to surround the incident end 48a.

With the above-mentioned configuration, the ambient illuminating light is illuminated to the integrating sphere 48c, thus, the light is diffused and passed, and the light is incident on the incident end 48a of the optical fiber 48. The incident light is transmitted by the optical fiber 48 and the spectrums are measured by the second spectrum sensor 46.

According to the fourth embodiment, the same advantages as those according to the first to third embodiments are obtained. The spectrum sensor is arranged. Thus, the spectrum distribution of the subject light is obtained, the spectrum distribution of the LEDs is obtained, and the color is accurately reproduced in real time.

The use of the optical system for sensor enables the spectrum distribution of the specific portion of the subject to be obtained. As mentioned above, the optical system for sensor has the resolution of 5 nm. Therefore, it is possible to obtain the specific spectrum data of the specific portion of the subject and the detailed diagnosis or determination is performed by the obtained data.

Further, the profile of the illuminating spectrum of the ambient illuminating light is obtained in real time because the spectrum of the ambient illuminating light can be sensed.

Next, a description is given of an image processing system according to a fifth embodiment of the present invention.

Figure 43:
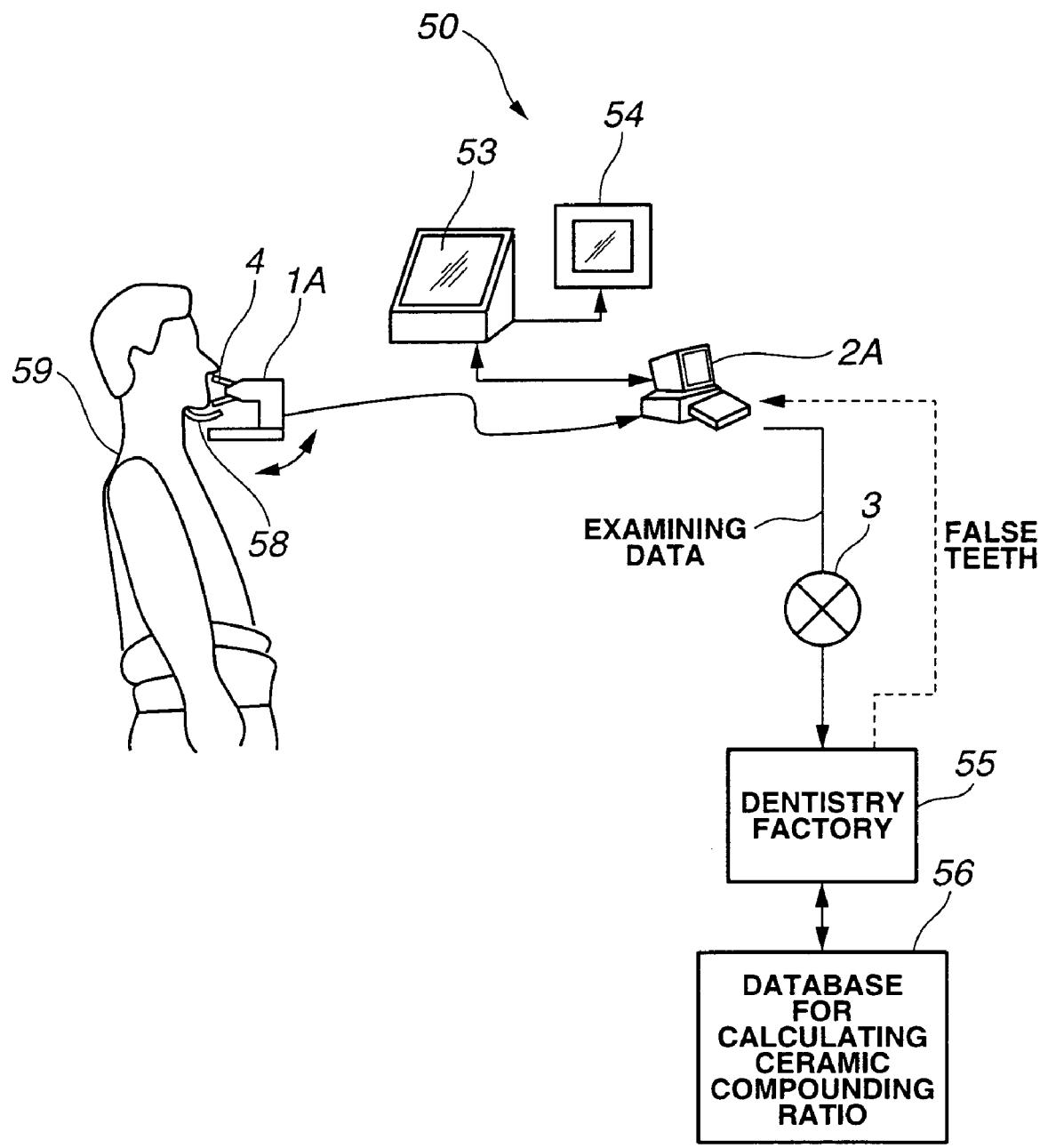
FIG. 43 is a diagram showing the configuration of an image processing system for dentistry according to a fifth embodiment of the present invention.
Figure 44:
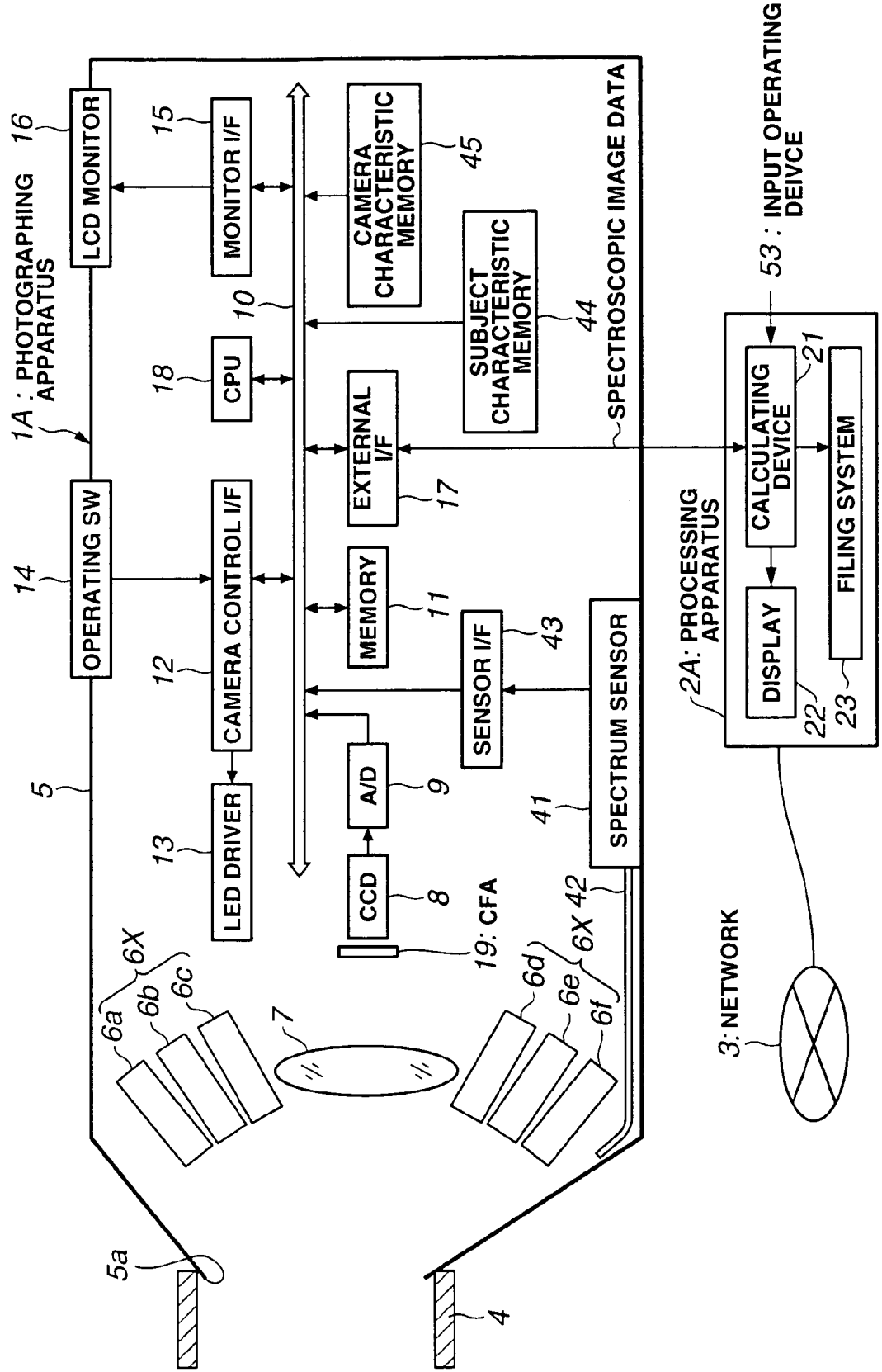
FIG. 44 is a block diagram showing the configuration of a photographing apparatus in the image processing system for dentistry shown in FIG. 43.

FIG. 43 is a diagram showing the system configuration of an image processing system for dentistry according to the fifth embodiment of the present invention. FIG. 44 is a block diagram showing the configuration of a photographing apparatus in the image processing system for dentistry.

An image processing system 50 for dentistry according to the fifth embodiment captures the spectroscopic image information of the tooth of the patient 59 upon creating the false tooth and an implant, reproduces the color at high fidelity level, and exchange the spectroscopic image information with a dentistry factory 55 via the network 3, thereby performing the whitening processing as the dental esthetics.

Referring to FIG. 43, the image processing system 50 for dentistry comprises: a photographing apparatus (hand held multi-spectrum scope, abbreviated to an HMSC) 1A; a processing apparatus 2A serving as an image processing unit, which has an image memory and calculates and manages the image data captured by the photographing apparatus 1A; a touch-panel input operating device 53 for camera photographing operation; a calibration monitor 54 for displaying the color reproducing state; the network 3 for connecting the processing apparatus 2A to a dentistry factory (communication device) 55; and a database 56 for calculating a ceramic compounding ratio provided for the dentistry factory 55.

In the photographing apparatus 1A, a plurality of LEDs 6X with different spectroscopic distribution characteristics are light sources, and the subject image (tooth image of the patient 59 in this case) illuminated by the light sources is captured via the image pick-up optical system 7. Then, the CCD 8 serving as the image pick-up device converts the captured subject image into an image pick-up signal, and is stored in the memory 11 as the image data. The image data is transferred to the image memory in the processing apparatus 2A via the external I/F 17. The photographing apparatus 1A has the same configuration as that of the photographing apparatus 1 (shown in FIGS. 1, 17, 21, and 37) in the image processing system according to the first to fourth embodiments. Referring to FIG. 44, the same components are designated by the same reference numerals.

Referring to FIG. 44, the processing apparatus 2A serving as the image processing unit comprises the calculating device 21 and the display 22 applied in the image processing unit 2 of the image processing system according to the first embodiment and a filing system 23 for dentistry.

The calculating device 21 performs the color reproduction calculating processing of the subject and the image determining and calculating processing (quantitative determination) based on the spectroscopic image data and the like captured by the photographing apparatus 1A. The image determining and calculating processing performs, for example, determining the tooth whitening level and tooth tone, the correlation and the entropy analysis between the crista cutis and the sulcus cutis on the skin surface. The calculating device 21 has the same configuration and functions as those of the calculating device 21 in the processing apparatus 2A in the image processing system according to the first embodiment.

The filing system 23 for dentistry is a system for data filing of the calculating results of the numerical value management before/after the whitening of the patient tooth, whitening frequency, and false tooth ceramic composition, and includes image filing software. A predetermined memory portion in the filing system 23 records and captures, into predetermined portions of the image filing software, the image data photographed by the photographing apparatus 1 with the operation of the operating switch 14.

Next, a description is given of the processing operation of the image processing system 50 for dentistry according to the fifth embodiment of the present invention.

In the dentist, upon creating the false tooth matching the tooth color of the patient 59 in the image processing system 50 for dentistry, the tone or whitening of the tooth of the patient 59 is measured. The jaw portion of the patient 59 is placed on a fixing table 58 and the head is fixed. The fixing table 58 has a photographing apparatus 51 attached. The abutting portion 4 having the shading property of the disposable material is abutted to the mouth of the patient 59 and the periphery of the tooth into which the false tooth in the mouth is inputted is set to a photographing state for the photographing apparatus 1. As mentioned above, the photographing apparatus 51 is fixed, thereby preventing the deviation of the subject position upon photographing.

By operating the touch-panel input operating device 53, a light-emitting mode of the LEDs 6X in the photographing apparatus 1 is selected and is designated. The light-emitting mode includes, for example, a mode for sequentially lighting-on each of the LEDs 6X for the single primary color, a mode for selecting the LED and lighting-on it, and a mode for simultaneously lighting-on all the LEDs and the like. The light-emitting modes designate the spectroscopic image capturing mode, the monitoring image capturing mode, or the number of spectroscopic bands in the spectroscopic image capturing mode.

After that, the light-on operation of the LEDs 6X starts by operating the input operating device 53. This operation is performed by the operating switch 14 in the photographing apparatus 1.

When the spectroscopic image capturing mode is selected, the subject image signal of the tooth of the patient 59 is captured by lighting-on the LEDs 6X via the CCD 8, and is stored in the memory 11 as the spectroscopic image data. The spectroscopic image data is transferred to the processing apparatus 2, and the color-reproduction calculating unit 33 (refer to FIG. 12) performs the XYZ estimation and calculation. The image in which the color is reproduced at high fidelity level of the tooth of the patient 59 is displayed on the display 22 or the calibration monitor 54.

When the capturing mode of the monitoring image is selected, the normal display image is displayed on the display 22. The spectroscopic image capturing mode and the monitoring image capturing mode are exchanged by the input operating device 53.

Further, the image determining and calculating unit 34 (refer to FIG. 13) in the processing apparatus 2A calculates for determining the spectroscopic image data based on the spectroscopic image data, thereby obtaining the grade data on the tone of the color of the tooth of the patient 59. The grade data is used for the shading guide for comparing the tone of the tooth color, and the value of the grade data is displayed on the calibration monitor 54. The processing apparatus 2A calculates using the grade data for ceramic compound of the false tooth and obtains the data false-tooth ceramic compound.

Examining data as the grade data on the tooth color tone, the color reproducing image data on the tooth of the patient 59, and the false-tooth ceramic composition data are transferred to a computer unit in the dentistry factory 55 via the network 3.

In the dentistry factory 55, a specific ceramic composition rate is searched from the database 56 for calculating the ceramic compounding ratio based on the examining data and the false-tooth ceramic composition data. The false tooth is created based on the ceramic composition rate. The created false tooth is sent to the dentist, and is further sent to the patient 59.

In the curing processing, the data on the tooth color and the color reproducing image are displayed on the calibration monitor 54 via the input operating device 53 with respect to the patient 59, and the curing processing is displayed with respect to the patient 59 and the acceptation by the patient 59 is obtained.

The image processing system 50 for dentistry is applied not only to the creation of the false tooth of the patient 59 but also to the whitening curing of the tooth. That is, the tooth of the patient 59 before/after the whitening processing is photographed by the photographing apparatus 1A and the above-mentioned image calculating processing is executed. Thus, the color reproducing image data indicating the whitening result and the grade data on the tooth color are obtained. The numeric data before/after the whitening curing is displayed on the calibration monitor 54, and the curing for the patient 59 in the informed consent is possible. Further, it is possible to visually check the change, due to the aging change and whitening frequency, in the color reproducing image data and the grade data in the curing processing. The data in the curing processing is stored.

In the image processing system 50 for dentistry according to the fifth embodiment, the color reproducing image data at high fidelity level and the grade data obtained by the processing apparatus 2A are not influenced from the normal room light and, therefore, there is no individual difference without the influence of the ambient light, unlike the comparison data using the conventional shading guide. Further, the using camera and film don't influence the color reproducing image and grading data. Furthermore, since the calibration monitor 54 observes the curing process, the curing of the patient 59 in the informed consent is possible.

The touch-panel input operating device 53 is used, and the abutting portion 4 attached to the tip of the photographing portion in the photographing apparatus 1A is disposable. Thus, the hospital infection is prevented.

The image processing system 50 for dentistry is applied to another field of the dentistry. In the case of applying the image processing system 50 for dentistry to the dermatology, the skin during the curing is photographed, the image reproducing image data is precisely obtained, and the change in skin is recorded without the variation due to the illumination. Further, in the case of applying the image processing system 50 for dentistry to the skin diagnosis system, the skin color is accurately reproduced under the normal standard illumination and the skin is reproduced under the specific illumination.

Next, a description is given of an image processing system according to a sixth embodiment of the present invention with reference to FIGS. 45 to 48.

Figure 45:
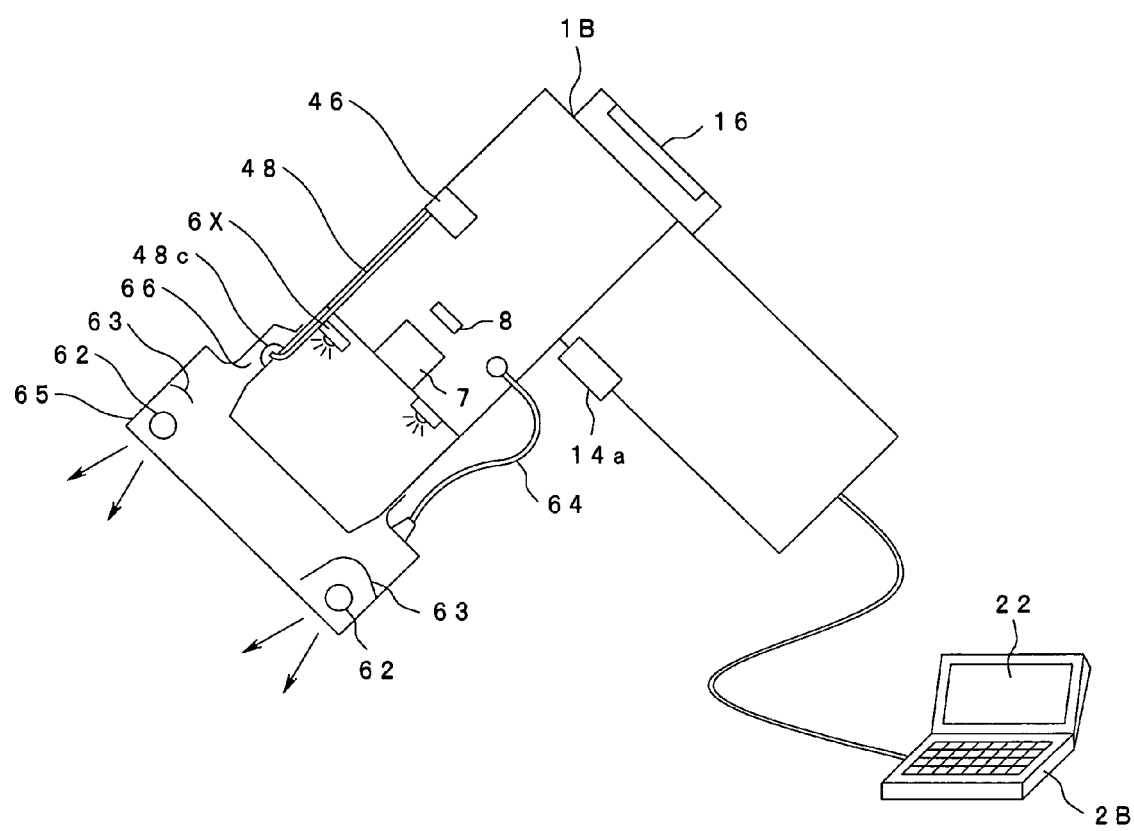
FIG. 45 is a diagram showing the configuration of an image processing system according to a sixth embodiment of the present invention.
Figure 46:
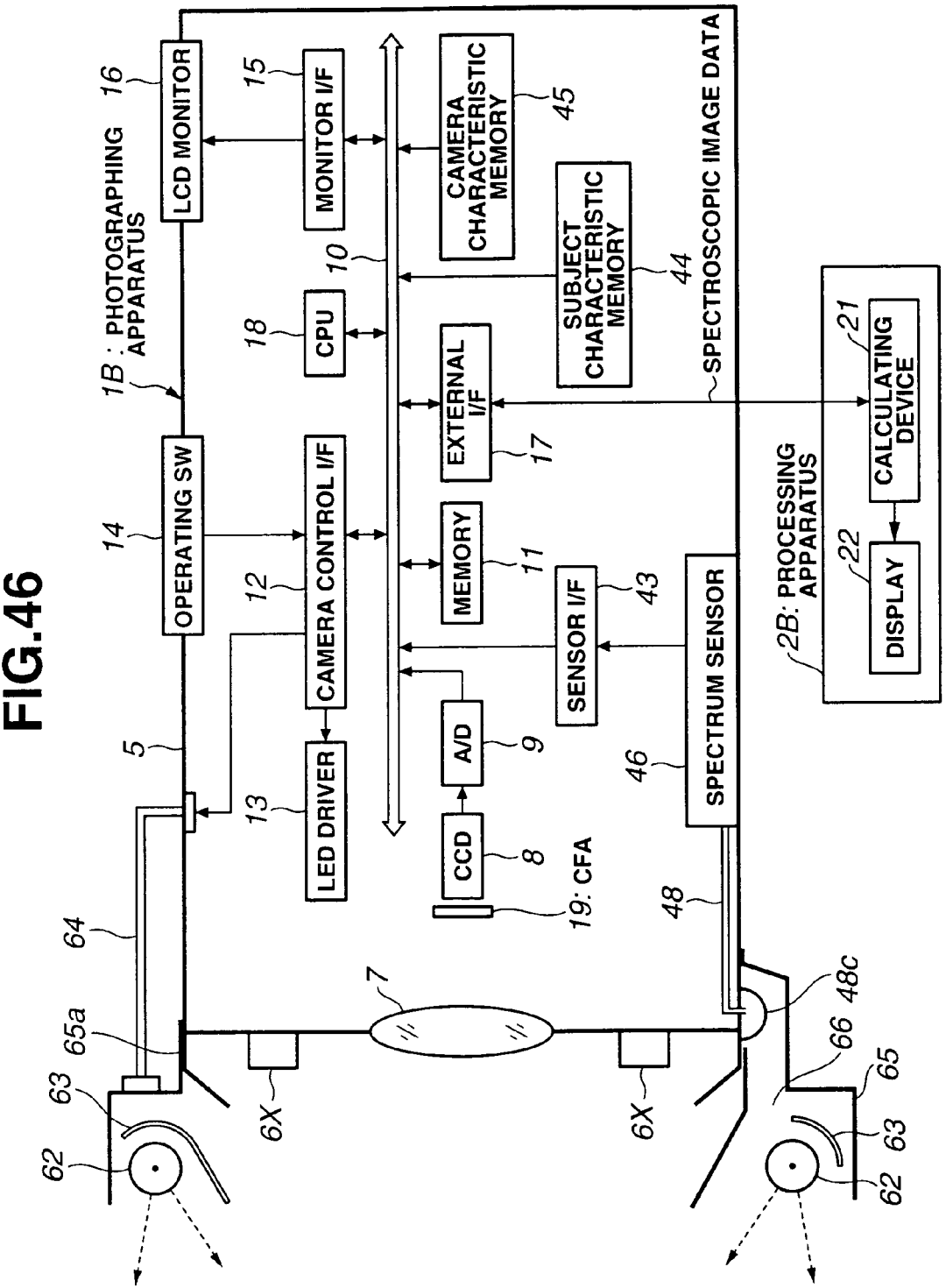
FIG. 46 is a block diagram showing the image processing system shown in FIG. 45.
Figure 47:
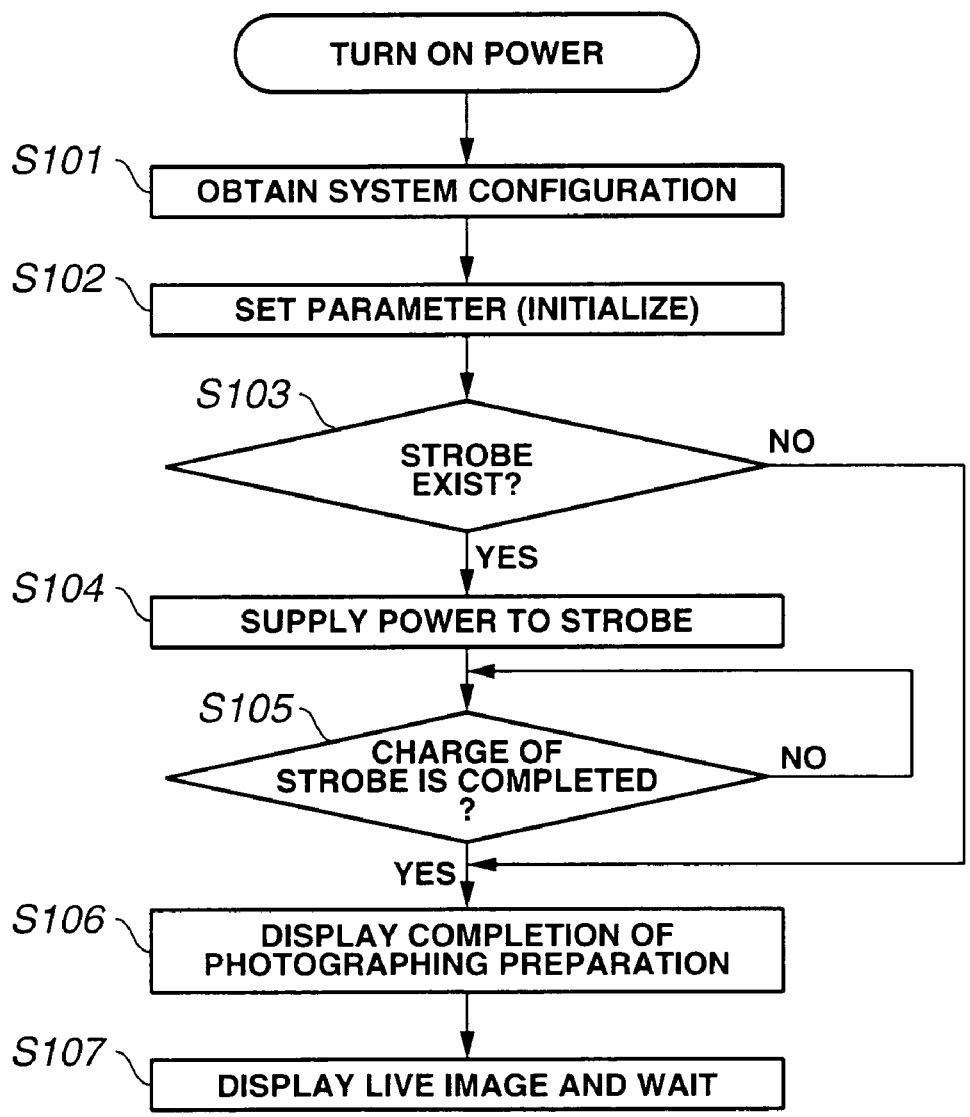
FIG. 47 is a flowchart for a photographing waiting processing routine in photographing processing of a photographing apparatus in the image processing system shown in FIG. 45.
Figure 48:
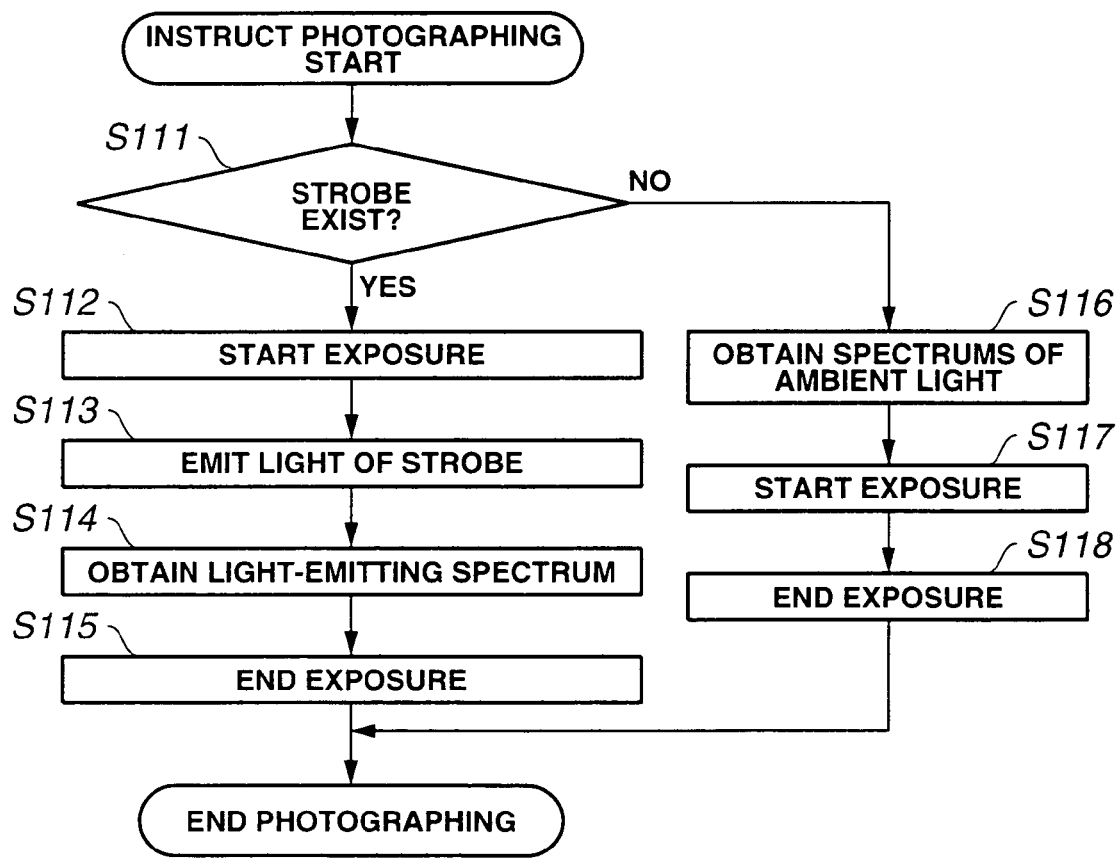
FIG. 48 is a flowchart for a photographing routine in the photographing processing in the photographing apparatus in the image processing system shown in FIG. 45.

FIG. 45 is a diagram showing the configuration of the image processing system according to the sixth embodiment. FIG. 46 is a block diagram showing the configuration of the image processing system. FIGS. 47 and 48 are flowcharts of the photographing processing in the photographing apparatus of the image processing system, FIG. 47 is the flowchart for a photographing waiting routine, and FIG. 48 is the flowchart for a photographing routine.

Referring to FIGS. 45 and 46, the image processing system according to the sixth embodiment is an image capturing unit, and comprises: a photographing apparatus 1B which photographs an image with the illuminating light of LED or the illuminating light of strobe; and a processing apparatus 2B, serving as the image processing unit, having an image memory, which obtains the color reproducing image data at high fidelity level from the spectroscopic image signal obtained by the photographing of the photographing apparatus 1B.

The photographing apparatus 1B has the same configuration and functions as those of the photographing apparatus 1 (refer to FIG. 38) having the color CCD and the sensor of the illuminating light in the image processing system according to the fourth embodiment. Further, a strobe light-emitting device 65 serving as an external strobe device is attached to the photographing apparatus 1B. Referring to FIG. 46, the same reference numerals in the photographing apparatus 1B as those in the photographing apparatus 1 denote the same components.

The processing apparatus 2B has the same configuration and functions as those of the processing apparatus 2 in the image processing system according to the fourth embodiment.

In the photographing apparatus 1B, the image of the close subject is photographed with the built-in LED illumination. When the distance to the subject is several cm to several m, the illuminating light of the built-in LED does not reach the subject. In this case, the strobe light-emitting device 65 is attached to the photographing apparatus 1B, then, a strobe light-emitting tube emits the light, and the photographing operation is performed.

The strobe light-emitting device 65 is attached in front of the casing 5 forming the device main body of the photographing apparatus 1B. However, when the strobe light-emitting device 65 is not attached to the photographing apparatus 1B, the integrating sphere 48c is externally exposed and therefore the second spectrum sensor 46 in the photographing apparatus 1B senses the spectrums of the ambient light. Further, when the strobe light-emitting device 65 is attached to the photographing apparatus 1B, the strobe light is partly guided to the integrating sphere 48c and therefore the second spectrum sensor 46 senses the spectrums of the strobe light.

Referring to FIG. 46, the strobe light-emitting device 65 comprises an attaching portion 65a which is detachably attached to the front portion of the casing 5 in the photographing apparatus 1B, a reflecting umbrella 63, a ring strobe light-emitting tube 62, a strobe light-emitting circuit (not shown) having a capacitor for light-emitting charge, and a connecting cable 64 for electrically connecting (power and control signal) the photographing apparatus 1B to the strobe light-emitting circuit.

After attaching the strobe light-emitting device 65, the photographing apparatus 1B is electrically connected to the strobe light-emitting device 65 by the connecting cable 64 via a connector. In addition, an electrode portion for connection is arranged to the attaching portion of the strobe device, and the electrode portion may be automatically connected, upon attaching the strobe light-emitting device 65 to the casing 5.

The CPU 18 on the photographing apparatus 1B side recognizes, via the camera control I/F 12, the electric connection using the connecting cable 64 or the electric connection as a result of attaching the strobe light-emitting device 65 to the casing 5, and a strobe identification code is sensed. The strobe identification code enables the update of the system configuration of the photographing apparatus that is currently stored.

The rear side of the reflecting umbrella is partly opened and thus a light guiding path 66 for guiding the strobe light to the back is formed. In the light emission of the strobe, the strobe light partly passes through the light guiding path 66, is incident on the integrating sphere 48c serving as a sensing portion arranged to the tip of the flash 48 of the spectrum sensor 46, and the spectrum sensor 46 senses the spectrum components of the strobe light.

Next, a description is given of the photographing processing operation of the photographing apparatus 1B with the above configuration according to the sixth embodiment with reference to the flowcharts shown in FIGS. 47 and 48.

Upon capturing the spectroscopic image data of the subject by the photographing apparatus 1B, a power switch of the photographing apparatus 1B is turned on. As a result of turning on the power switch, the photographing preparing processing routine shown in FIG. 47 starts under the control of the CPU 18.

In step S101, the CPU 18 fetches system configuration data. In step S102, a parameter is set (initialized). In step S103, it is checked whether or not the strobe light-emitting device 65 is attached to the photographing apparatus 1B. When the strobe is not attached to the photographing apparatus 1B, the processing jumps to step S106. However, when the strobe is attached, the processing advances to step S104.

In step S104, the power is supplied to the strobe light-emitting circuit, thereby starting the charge of the capacitor for charge of light emission. In step S105, it is confirmed that the charge is completed. Then, the processing advances to step S106 whereupon the end of photographing preparation is displayed on the LCD monitor 16. In step S107, the LCD monitor 16 is set to a live screen display state and waits.

A photographing person presses the photographing button 14*a* of the photographing apparatus 1B, then, an instructing signal of the photographing start is inputted. Thus, the photographing processing routine shown in FIG. 48 starts under the control of the CPU 18.

In step S111, it is checked whether or not the strobe is attached. When the strobe is not attached, the processing jumps to step S116. When the strobe is attached, the processing advances to step S112.

In step S112, the exposure of the CCD 8 starts. Further, in step S113, the light emission of the strobe of the strobe light-emitting device 65 starts. In step S114, the light emitted by the strobe partly passes through the light guiding portion 66, and is captured from the integrating sphere 48*c* to the spectrum sensor 46. The spectroscopic spectrum data of the strobe emitted-light is obtained. After predetermined exposure time, in step S115, the exposure ends and the photographing processing ends.

If the processing jumps to step S116, because the strobe light-emitting device 65 is not attached, the spectrum sensor 46 obtains the spectroscopic spectrum data of the ambient light. In step S117, the LEDs 6X emit the light in the desired light-emitting mode, and the exposure of the CCD 8 starts. In step S118, the exposure ends and then the photographing processing ends.

Although not shown in FIG. 46, the photographing apparatus 1B includes the spectrum sensor 47 as shown in FIG. 38. The spectrum sensor 47 simultaneously obtains the spectroscopic spectrum data of the illuminating light of the LEDs 6X.

After ending the photographing processing, the photographing image data captured in the memory 11 in the photographing apparatus 1B and the spectroscopic spectrum data of the illuminating light are transferred to the processing apparatus 2B via the external I/F 17. Further, the spectroscopic spectrum data of the illuminating light, the camera characteristic data, and the subject communication data are added to the photographing image data, and the spectroscopic image data is calculated and is obtained.

In the image processing system according to the sixth embodiment, even when the distance to the subject is relatively far and the light emitted by the LEDs 6X has insufficient luminance, the subject is photographed by attaching the strobe light-emitting device 65 to the photographing apparatus 1B. Further, the spectroscopic image data is calculated based on the spectroscopic spectrum data of the strobe light, which is obtained every light emission of the strobe. Therefore, it is possible to reproduce the color at high fidelity level based on the spectroscopic image data of which the variation in light-emitting space is corrected and the variation in spectrums of the light emission of the strobe light-emitting device 65 is corrected.

Next, a description is given of an image processing system according to a seventh embodiment of the present invention with reference to FIGS. 49 to 52.

Figure 49:
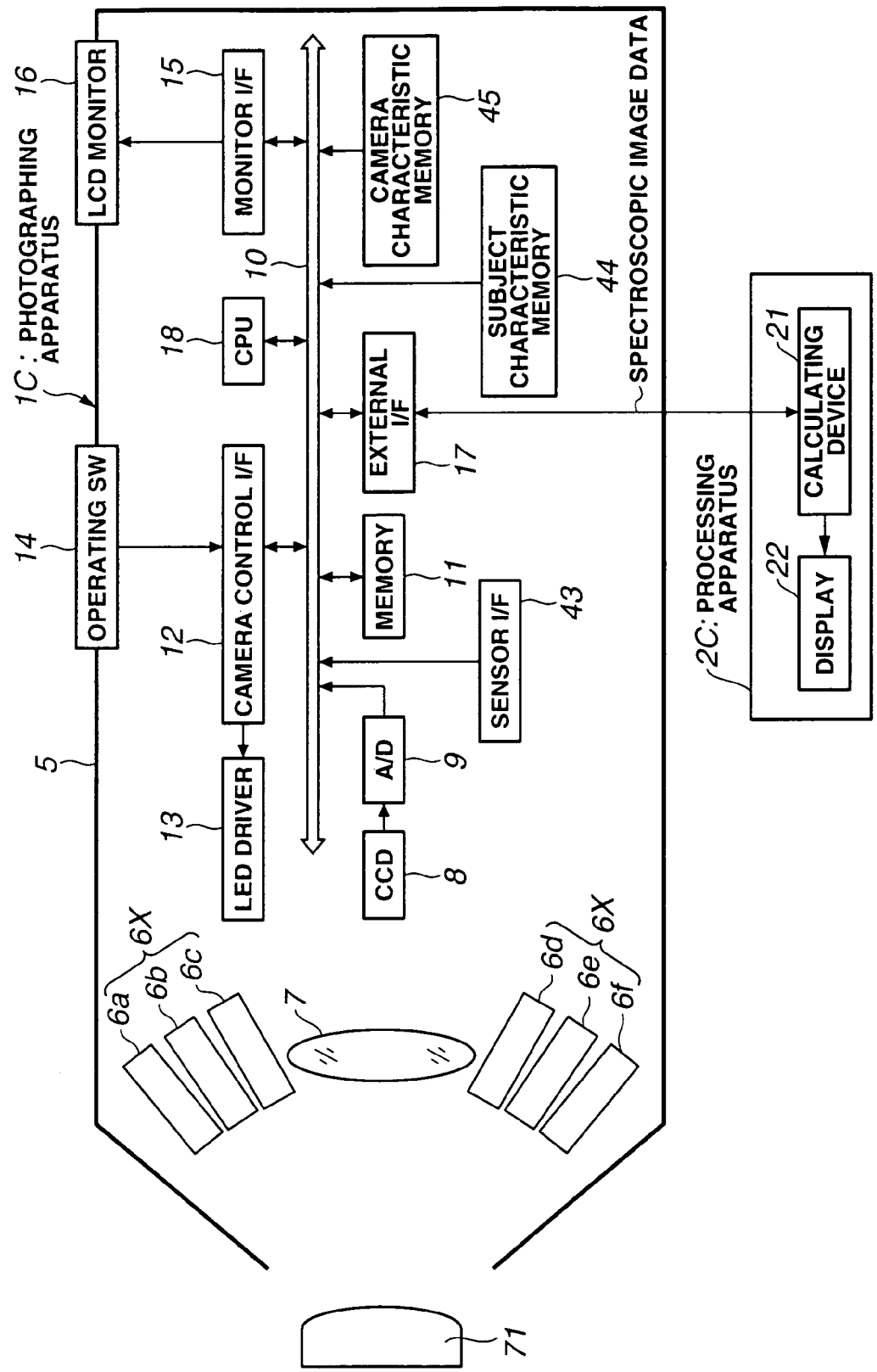
FIG. 49 is a block diagram showing the configuration of an image processing system according to a seventh embodiment of the present invention.
Figure 50:
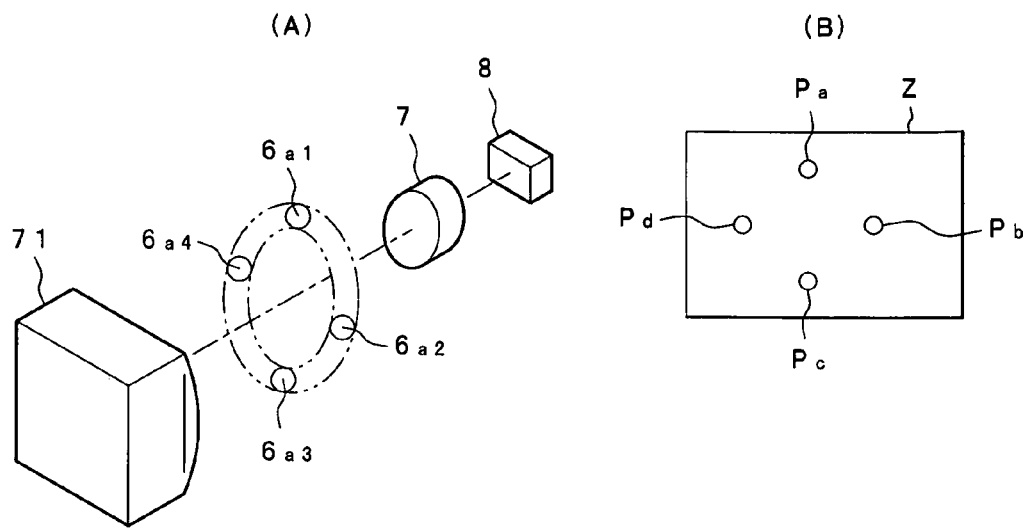
FIG. 50 is a diagram showing states of illuminating a regular-reflection subject with LED light of colors by a photographing apparatus in the image processing system shown in FIG. 49.
Figure 51:
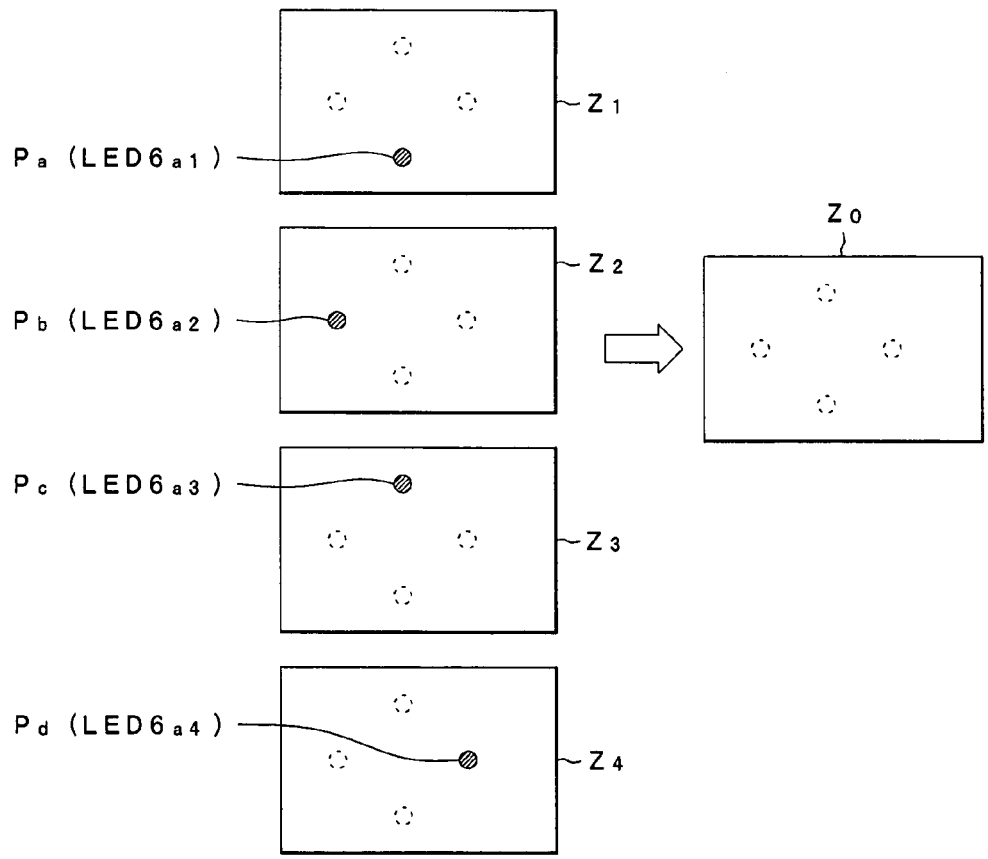
FIG. 51 is a diagram showing a subject image with the regular-reflection portion with the illumination of the LEDs of colors formed on the CCD upon illuminating the regular-reflection subject with the LEDs of colors by the photographing apparatus in the image processing system shown in FIG. 49 and a subject image from which the regular-reflection portion is removed by the photographing apparatus in the image processing system.
Figure 52:
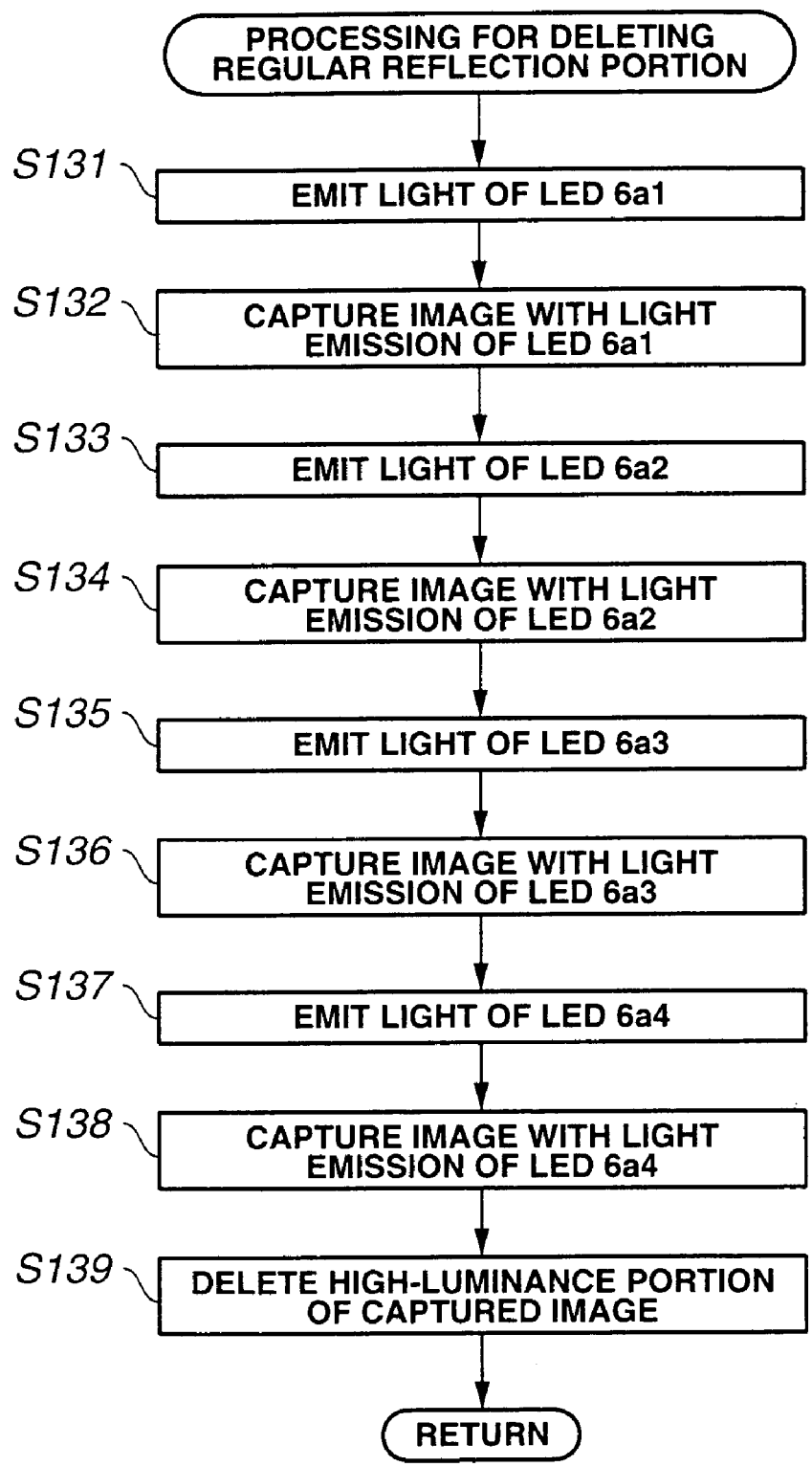
FIG. 52 is a flowchart of processing for removing the regular-reflection portion by the photographing apparatus in the image processing system shown in FIG. 49.

FIG. 49 is a block diagram showing the configuration of the image processing system according to the seventh embodiment. FIG. 50(A) and FIG. 50(B) are diagrams showing the states of illuminating with the LED light of colors the regular-reflection subject. FIG. 50(A) is a diagram showing the arrangement of the subject that regularly reflects when forming the image, the LEDs of colors, and the CCD. FIG. 50(B) is a diagram showing the image having a portion of regular reflection, whose image is formed on the CCD. FIG. 51 is a diagram showing the subject image having the portion of regular reflection being illuminated by the LEDs of colors on the image forming surface of the CCD and the subject image in which the portion of regular reflection is deleted from the subject image by the photographing apparatus in the image processing system. FIG. 52 is a flowchart for processing for deleting the portion of regular reflection by the photographing apparatus.

Referring to FIG. 49, the image processing system according to the seventh embodiment comprises: a photographing apparatus 1C, serving as an image capturing unit, which photographs the spectroscopic image that is not influenced by the regular reflection; and a processing apparatus 2C, serving as an image processing unit, which has an image memory and obtains the color reproducing image data at high fidelity level from the subject spectroscopic image signal photographed by the photographing apparatus 1C.

The processing apparatus 2C has the same configuration and functions as those of the processing apparatus 2 applied in the image processing system according to the first embodiment, and may be a personal computer.

Referring to FIG. 49, the photographing apparatus 1C has the same configuration as that of the photographing apparatus 1 (refer to FIGS. 1, 17, 21, and 37) in the image processing system according to the first to fourth embodiments. However, in the photographing apparatus 1C, the regular-reflection image data obtained as mentioned later is processed. The same components in the photographing apparatus 1C as those in the photographing apparatus 1 are designated by the same reference numerals.

In the photographing apparatus 1C, when a subject 71 has a curved surface with gloss, which performs regular reflection, the high-luminance portion which performs regular reflection by the illuminating light from the LEDs 6X is deleted from the image data, and the image data without the regular-reflection portion is obtained by the combining processing. Hereinbelow, the image processing will be described.

As an example, when the illuminating light from different LEDs 6*a*1 to 6*a*4 arranged like a ring is irradiated to the subject 71 which performs regular reflection, the LEDs emit the light having the same wavelength. The regular reflection is performed by the subject 71, colored high-luminance points form an image at different position on the image forming surface of the CCD 8. That is, on an image Z in FIG. 50(B), high-luminance points Pa, Pb, Pc, and Pd are generated, corresponding to the LEDs 6*a*1, 6*a*2, 6*a*3, and 6*a*4.

In the photographing apparatus 1C, the high-luminance points Pa, Pb, Pc, and Pd caused by the regular reflection are removed by the deletion of the portion of regular reflection. The deletion will be described with reference to FIG. 51. The regular-reflection image of the subject 71 by the light emitted by the LED 6*a*1 is shown by the high-luminance point Pa on a CCD image forming surface Z1. Similarly, the regular-reflection image of the subject 71 by the light emitted by the LEDs 6*a*2, 6*a*3, and 6*a*4 are shown by the high-luminance points Pb, Pc, and Pd on CCD image forming surfaces Z2, Z3, and Z4. The remaining image data which is obtained by removing the image data at the high-luminance points Pa, Pb, Pc, and Pd is added or is averaged, thereby obtaining the corrected spectroscopic image data (on a CCD image forming surface Z0) of the subject 71 with no high-luminance portion of the regular reflection.

The deletion of the regular-reflection portion will be described with reference to the flowchart in FIG. 52. In step S131, the LED 6*a*1 is lit-on. In step S132, the image data is obtained. Then, the LEDs 6*a*2, 6*a*3, and 6*a*4 are sequentially lit-on in steps S133 to S138, and the image data is obtained when the LEDs emit the light. In step S139, the image data obtained by removing the high luminance portion from the obtained image data is created, thereby obtaining the spectroscopic image data which is obtained by removing the regular-reflection portion. In the above-mentioned example, although the number of LEDs serving as the light source is four, the same processing is executed with another number of LEDs.

In the photographing apparatus 1C in the image processing system according to the seventh embodiment, the subject 71 performs regular reflection of the light and then the obtained image data is subjected to the deletion of the regular reflection. Thus, the spectroscopic image data without the regular reflection is obtained.

Figure 53:
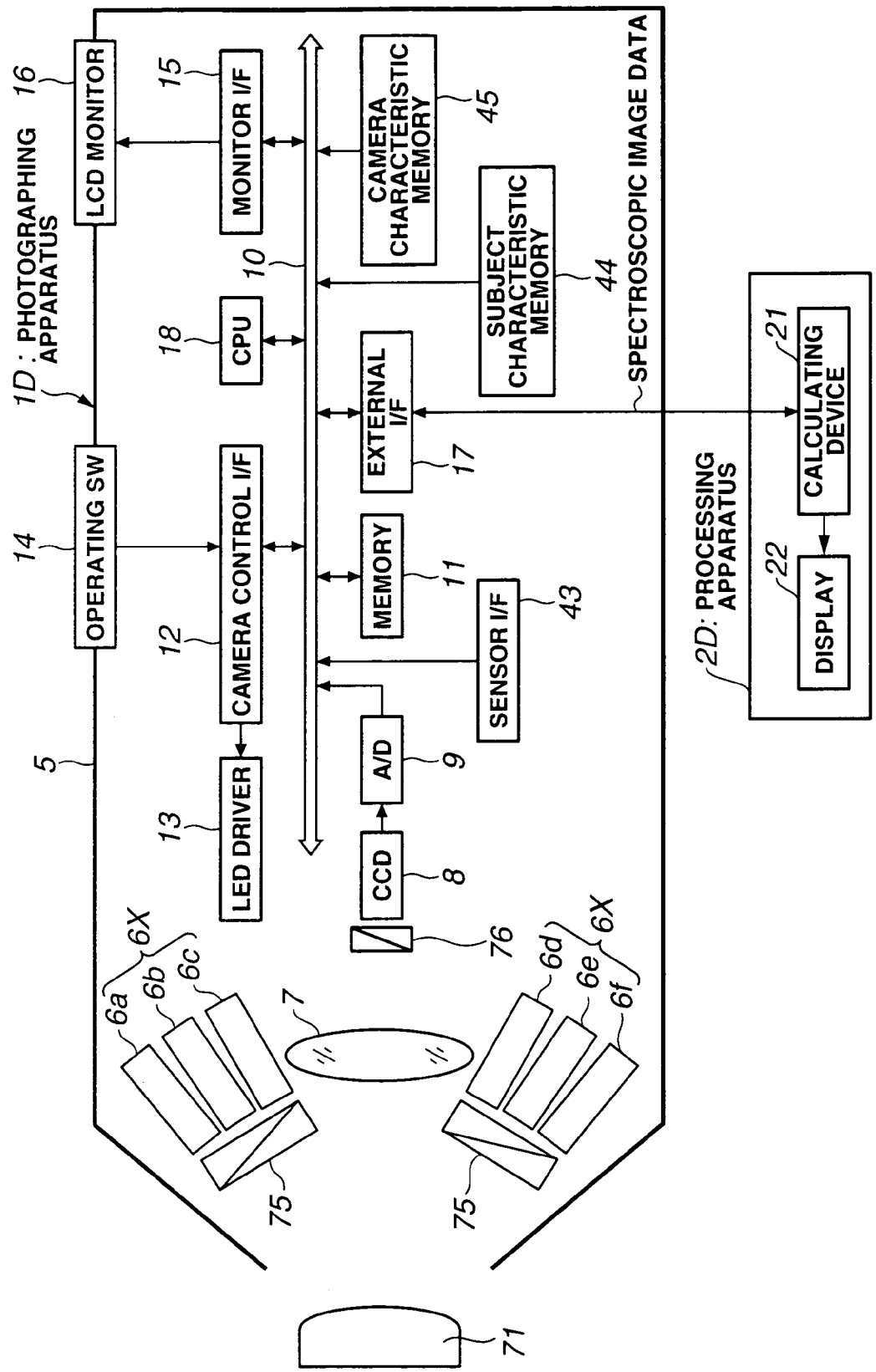
FIG. 53 is a block diagram showing an image processing system according to an eighth embodiment of the present invention.
Figure 54:
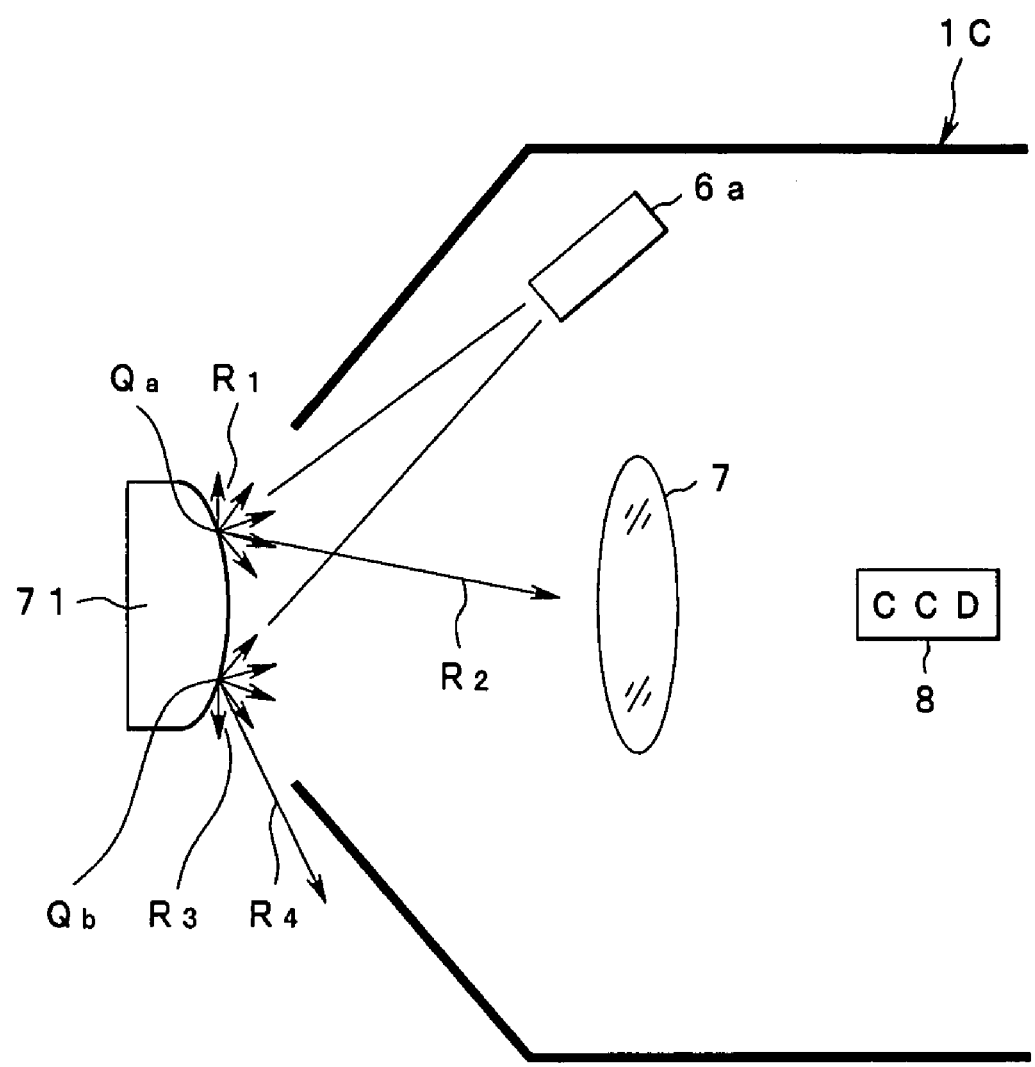
FIG. 54 is a diagram showing a light reflecting state on the regular-reflection subject in the case of photographing the regular-reflection subject by the photographing apparatus in the image processing system shown in FIG. 53.

Next, a description is given of an image processing system according to an eighth embodiment with reference to FIGS. 53 and 54.

FIG. 53 is a block diagram showing the image processing system according to the eighth embodiment. FIG. 54 is a diagram showing the light reflecting state of the regular-reflection subject.

Referring to FIG. 53, the image processing system according to the eighth embodiment comprises: a photographing apparatus 1D, serving as an image capturing unit, which photographs the spectroscopic image of the regular-reflection subject; and a processing apparatus 2D, serving as an image processing unit, which obtains the color reproducing image data at high fidelity level from the spectroscopic image signal of the subject which is photographed by the photographing apparatus 1D.

The processing apparatus 2D has the same configuration and functions as those of the processing apparatus 2 in the image processing system according to the first embodiment, and may be a personal computer.

Referring to FIG. 53, the photographing apparatus 1D has the same configuration as that of the photographing apparatus 1 (refer to FIGS. 1, 17, 21, and 37) in the image processing system according to the first to fourth embodiments. Further, in order to cut-off the regular-reflection light, the photographing apparatus 1D has a first polarizing plate 75 serving as reflected light rejecting means which is rotatable in front of the LEDs 6X as the illuminating light sources and a second polarizing plate 76 serving as reflected light rejecting means in front of the CCD 8.

The same components in the photographing apparatus 1D are designated by the same reference numerals.

In the case of obtaining the spectroscopic image data, diffused and reflected light based on the spectroscopic reflecting rate of the subject surface is sensed and the spectroscopic image data is obtained. However, when the surface of the subject 71 has the surface similar to the mirror, referring to FIG. 54, the illuminating light emitted to the subject 71 from the LED 6a is reflected as diffused and reflected light R1 and R3 (shown by short arrows in FIG. 54) at points Qa and Qb of the subject surface. However, the illuminating light is partly reflected as regular-reflection light R2 and R4 (shown by long arrow in FIG. 54). The regular-reflection light R2 and R4 are reflected in the symmetrical direction of an incident angle of the illuminating light, and have the same spectrums as those of the illuminating light. The components of regular-reflection light R2 and R4 are larger than those of the diffused and reflected light R1 and R3 and therefore becomes the obstacle of the measurement of the spectroscopic reflectance of the subject. The regular-reflection light R4 is not influenced from the measurement because the reflecting direction is not in that of the CCD 8 side. The regular-reflection light R2 is transmitted through the image pick-up optical system 7 and is captured in the CCD 8, and a portion at the point Qa is photographed at a high-luminance point. Therefore, the spectroscopic image data is not properly obtained unless the regular-reflection light component caused depending on the surface state of the subject 71 is removed.

Then, the photographing apparatus 1D according to the eighth embodiment comprises the first polarizing plate 75 in front of the LEDs 6X and the second polarizing plate 76 in front of the CCD 8. Thus, the regular-reflection light component is cut-off to prevent the incident state on the CCD 8. That is, the first polarizing plate 75 polarizes the illuminating light from the LEDs 6X. The light diffused and reflected by the surface of the subject 71 has various polarizing directions. However, the regular-reflection light is incident on the image pick-up optical system 7 while the polarizing state is kept. The first polarizing plate 75 is arranged by adjusting the rotating position with respect to the second polarizing plate 76. The polarized regular-reflection light is removed by the second polarizing plate 76. Only the diffused and reflected light is incident on the CCD 8 and the subject image with no high-luminance portion due to the regular reflection is photographed.

In the case of applying the photographing apparatus 1D in the image processing system according to the eighth embodiment, even if the subject 71 has the gloss surface, the photographed image does not have the high-luminance portion due to the regular reflection, and the spectroscopic image data is properly obtained to reproduce the color at high fidelity level.

In the photographing apparatus 1D, the second polarizing plate 76 is arranged between the image pick-up optical system 7 and the CCD 8. However, with the same effect, the second polarizing plate 76 is arranged to the subject 71 side in front of the image pick-up optical system 7.

Figure 55:
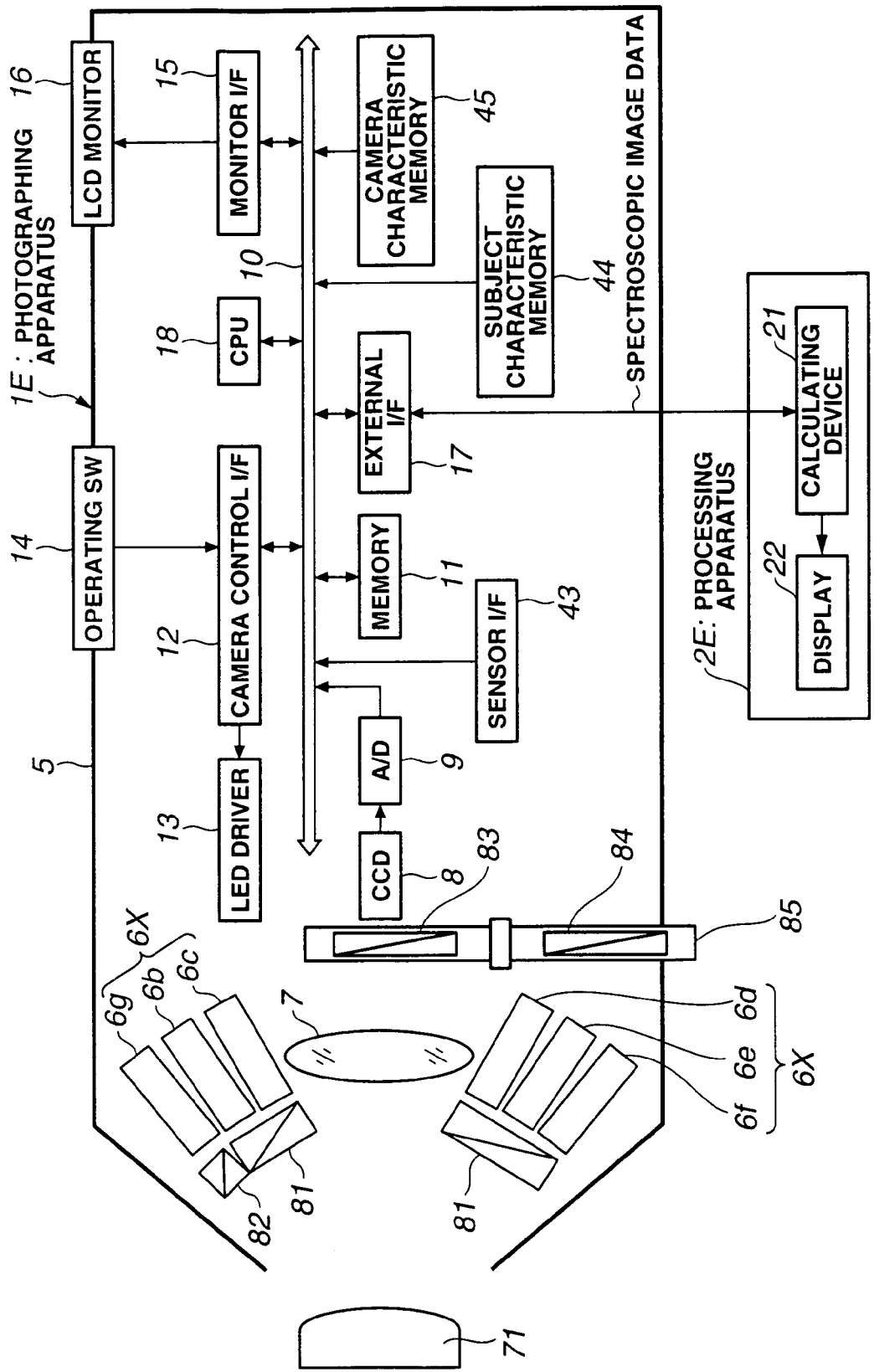
FIG. 55 is a block diagram showing the configuration of an image processing system according to a ninth embodiment of the present invention.
Figure 56:
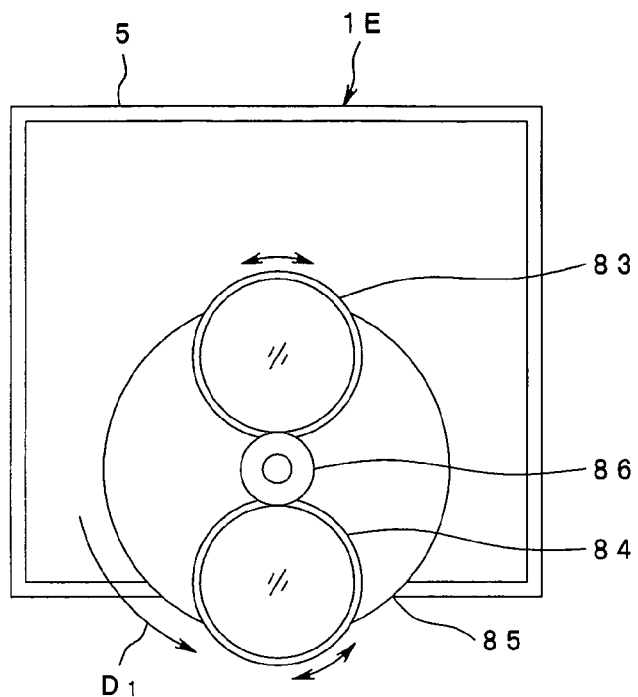
FIG. 56 is a front view showing a second polarizing plate arranged in front of a CCD in a photographing apparatus in the image processing system shown in FIG. 55.

Next, a description is given of an image processing system according to a ninth embodiment with reference to FIGS. 55 and 56.

FIG. 55 is a block diagram showing the configuration of the image processing system according to the ninth embodiment. FIG. 56 is a front view showing the second polarizing plate arranged in front of the CCD in the photographing apparatus in the image processing system.

Referring to FIG. 55, the image processing system according to the ninth embodiment comprises: a photographing apparatus 1E, serving as an image capturing unit, which photographs the spectroscopic image of the visible light and the near infrared light of the regular-reflection subject; and a processing apparatus 2E, serving as an image processing unit, which obtains the color reproducing image data at high fidelity level from the spectroscopic image signal of the subject which is photographed by the photographing apparatus 1E.

The processing apparatus 2E has the same configuration and functions as those of the processing apparatus 2 in the image processing system according to the first embodiment, and may be a personal computer.

Referring to FIG. 55, the photographing apparatus 1E has the same configuration as that of the photographing apparatus 1 (refer to FIGS. 1, 17, 21, and 37) applied in the image processing system according to the first to fourth embodiments. Further, in the photographing apparatus 1E, the LEDs 6X serving as the visible light sources of the illuminating light and an LED 6g serving as the near infrared light source are arranged around the image pick-up optical system 7. Furthermore, in order to cut-off the regular-reflection light, the photographing apparatus 1E has a first polarizing plate 81 serving as reflected light rejecting means in front of the LEDs 6X and a second polarizing plate 82 in front of the CCD 8. In addition, the CCD 8 has, in front thereof, a rotatable polarizing dial 85

(refer to FIG. 56) having second polarizing plates 83 and 84 serving as the reflected light rejecting means.

The same components in the photographing apparatus 1E are designated by the same reference numerals. Only different processing portions are described.

In the photographing apparatus 1E, the spectroscopic image data of the visible light is obtained by lighting-on the LEDs 6X. Further, the spectroscopic image data of the near infrared light is obtained by lighting-on the LED 6g.

In this case, when the subject is the subject 71 having the gloss, the regular-reflection light is captured and the image data has the high-luminance portion. However, in the photographing apparatus 1E, the regular-reflection light is removed not only from the subject image of the visible light but also from the subject image of the infrared light. In any case, the spectroscopic image data with no high-luminance portion is properly captured.

In the photographing apparatus 1E, the polarizing plate dial 85 has the second polarizing plate 83 for visible light and the second polarizing plate 84 for near infrared light.

In the case of photographing operation using the visible light from the photographing apparatus 1E, the polarizing plate 85 is manually rotated in the direction of an arrow D1, thereby switching the second polarizing plate 83 for visible light to face the CCD 8. After switching operation, the second polarizing plate 83 for visible light is rotated via a center rotary roller 86 by rotating the second polarizing plate 84 for near infrared light projected to the outside of the photographing apparatus casing. Thus, the first polarizing plate 81 for visible light is adjusted.

The LEDs 6X for visible light are lit-on in a predetermined light-emitting mode and thus the light passed through the first polarizing plate 81 is reflected by the subject 71 and is incident on the image pick-up optical system 7. The diffused light component among the reflected light is transmitted through the second polarizing plate 83. However, the regular-reflection light component is removed by the second polarizing plate 83. Therefore, the CCD 8 converts, into an image pick-up signal, the subject image of the visible light with no high-luminance portion due to the regular reflection, and the spectroscopic image data is captured.

In the case of the photographing operation using the near infrared light, the polarizing plate dial 85 is manually rotated such that the second polarizing plate 84 for near infrared light faces the CCD 8. The second polarizing plate 84 for near infrared light is rotated via the center rotary roller 86 by rotating the second polarizing plate 83 for visible light projected to the outside of the photographing apparatus casing. Thus, the first polarizing plate 82 for near infrared light is adjusted.

The LED 6g for near infrared light is lit-on in a predetermined light-emitting mode. Then, the near infrared light passing through the first polarizing plate 82 is reflected by the subject 71 and is incident on the image pick-up optical system 7. The diffused light component among the near infrared light components is transmitted through the second polarizing plate 84. However, the regular-reflection light component is removed by the second polarizing plate 84. Therefore, the CCD 8 converts, into an image pick-up signal, the subject image of the near infrared light with no high-luminance portion due to the regular reflection, and the spectroscopic image data is captured.

In the photographing apparatus 1E of the image processing system according to the ninth embodiment, the image is photographed with the light source of the near infrared light as well as with the light source of the visible light. Further, the image of the regular-reflection subject with the gloss is captured without the high-luminance portion and the influence of the regular reflection of both light sources, and the spectroscopic image data is captured. Thus, the color is reproduced at high fidelity level.

The photographing apparatus 1E does not need to use such an expensive polarizing plate as the polarizing property overwhelms the entire wavelengths ranging from the visible light to the near infrared light. The inexpensive first polarizing plate 81 and second polarizing plate 83 are used for the light source of the visible light. The first polarizing plate 82 and second polarizing plate 84 for near infrared light are used for the light source of the near infrared light. Therefore, the cost of parts is suppressed.

Figure 57:
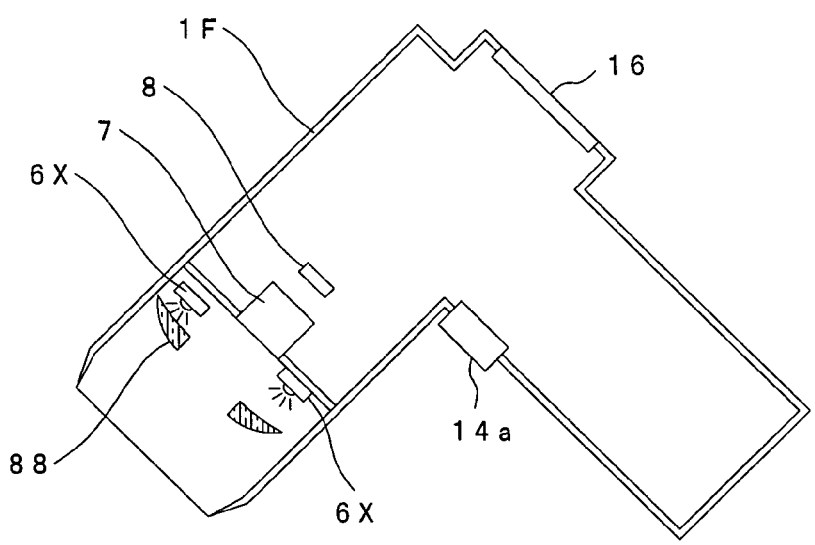
FIG. 57 is a block diagram showing the configuration of an image processing system according to a tenth embodiment of the present invention.

Next, a description is given of an image processing system according to a tenth embodiment with reference to FIGS. 57 to 59.

FIG. 57 is a block diagram showing the configuration of the image processing system. FIGS. 58(A) and 58(B) are diagrams showing shading states of the LED light source before correction in a photographing apparatus of the image processing system. FIGS. 59(A) and 59(B) are diagrams showing the shading state of the LED light source after correction in the photographing apparatus of the image processing system.

The image processing system according to the tenth embodiment comprises: a photographing apparatus 1F, serving as an image capturing unit; and a processing apparatus (not shown), serving as an image processing unit, which obtains the color reproducing image data from the spectroscopic image signal of the subject photographed by the photographing apparatus 1F.

Referring to FIG. 57, the photographing apparatus 1F has the same configuration as that of the photographing apparatus 1 (refer to FIGS. 1, 17, 21, and 37) in the image processing system according to the first to fourth embodiments. Further, the photographing apparatus 1F comprises a shading correcting lens 88 serving as an optical member which reduces the illuminating inhomogeneity in front of the LEDs 6X as the illuminating light sources.

The same components in the photographing apparatus 1F are designated by the same reference numerals. Only different processing portions are described.

In the photographing apparatus 1F, when the shading correcting lens 88 is not attached and the LED 6a and the LED 6d are individually lit-on among the LEDs 6X arranged at the different positions, referring to FIGS. 58(A) and 58(B), different portions of the subject are more brightly illuminated compared with the other portions as shown by the upper left on a screen G1 and the upper right on a screen G2. If these portions are not corrected, the accurate measurement is not possible because the spectrum intensity distributions observed depending on the positions on the screens are varied.

Then, in the photographing apparatus 1F, the shading correcting lens 88 is attached in front of the LEDs 6X. The shading correcting lens 88 is attached, and so the illuminating light from the LED 6a or 6d is adjusted. On screens G3 and G4 shown in FIGS. 59(A) and 59(B), the bright portion is corrected so as to be collected to the center of the screens. The correction of the illuminating light reduces the influence due to the light source position, no error of spectrum strength distribution due to the position on the screen exists, and the correct measurement is performed. Further, the spectroscopic image data is obtained at high fidelity level.

Even with the configuration of the photographing apparatus 1F according to the eighth embodiment, the shading influenced by the illuminating position remains. In this case, a white sheet is photographed as the subject, and shading correcting data for the position on the screen of each of the LEDs 6X is calculated based on the obtained image data. Further accurate correction is possible by the electric shading correction for each LED.

The above example combinedly uses the optical shading correction and image-processing shading correction. However, the same correcting advantage is obtained by the shading correction using only the image processing without using the shading correcting optical system 88.

In place of the shading correcting optical system (lens) 88, a diffusing plate can correct the shading.

Figure 60:
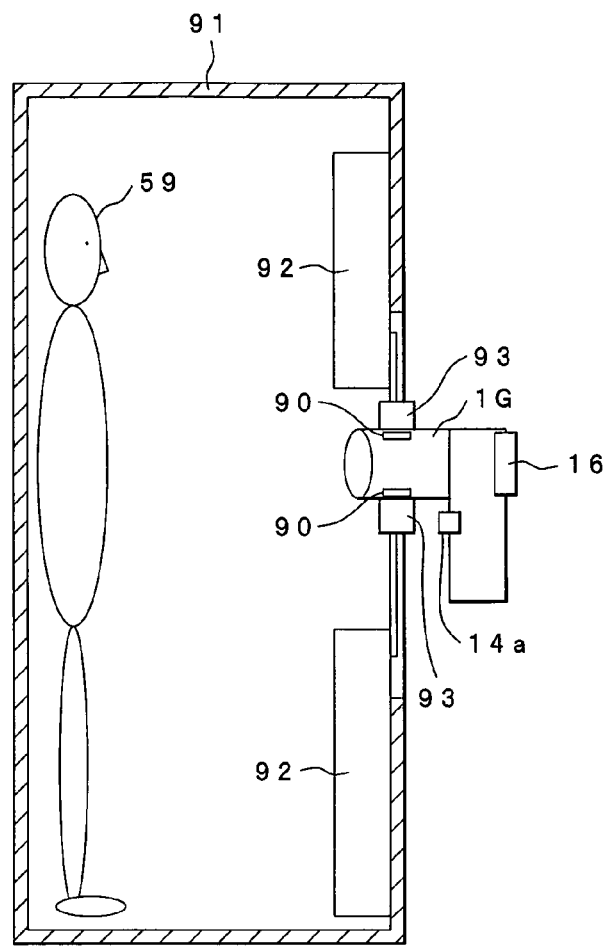
FIG. 60 is a block diagram showing the configuration of an image processing system according to an eleventh embodiment of the present invention.
Figure 61:
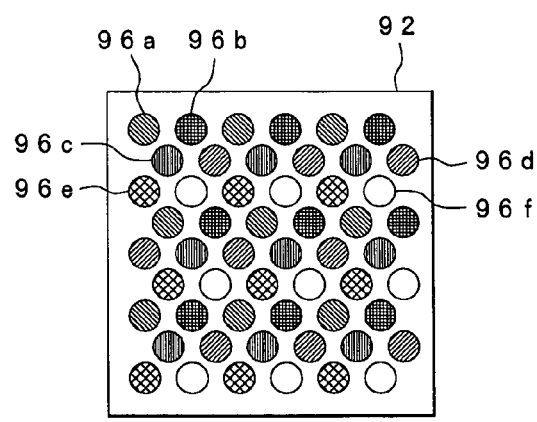
FIG. 61 is a diagram showing the arrangement of an LED light source unit of a photographing apparatus in the image processing system shown in FIG. 60.

Next, a description is given of an image processing system according to an eleventh embodiment of the present invention with reference to FIGS. 60 and 61.

FIG. 60 is a block diagram showing the configuration of the image processing system according to the eleventh embodiment. FIG. 61 is a diagram showing the arrangement of an LED light source unit of a photographing apparatus in the image processing system.

The image processing system according to the eleventh embodiment comprises: a photographing apparatus 1G serving as an image capturing unit; a dark room 91 serving as a photographing room; and a processing apparatus (not shown) serving as an image processing unit which obtains the color reproducing image data at high fidelity level from the spectroscopic image signal of the subject photographed by the photographing apparatus 1G.

Referring to FIG. 60, the photographing apparatus 1G has the same configuration as that of the photographing apparatus 1 (refer to FIGS. 1, 17, 21, and 37) in the image processing system according to the first to fourth embodiments. Further, the photographing apparatus 1G comprises a connecting terminal portion (contact portion) 90 connected to the illuminating light source in the dark room 91. The same components in the photographing apparatus 1G as those in the photographing apparatus 1 are designated by the same reference numerals.

The processing apparatus has the same configuration and functions as those of the processing apparatus 2 in the image processing system according to the first embodiment, and may be a personal computer.

The dark room 91 has a space for the patient 59, and has the structure that is shaded from the outside. The dark room 91 further has a plurality of illuminating devices 92 serving as external illuminating devices.

Referring to FIG. 61, the illuminating devices 92 respectively have a plurality of sets of LEDs 96a to 96f with the same light-emitting wavelengths respectively as those of the LEDs 6a to 6f serving as the LEDs 6X included in the photographing apparatus 1G. In FIG. 61, circular marks denote the LEDs, and the same pattern of the circular mark denotes the LED having the same light-emitting wavelength. Referring to FIG. 61, the LEDs 96a to 96f are uniformly distributed in the illuminating devices 92 without deviation, thus substantially enabling the surface light-emission. The power to the LEDs 96a to 96f is supplied via a connector 93. The connector 93 is connected to the connecting terminal portion 90 on the side of the photographing apparatus 1G when the photographing apparatus 1G is attached in the dark room 91.

In the photographing operation using the photographing apparatus 1G with the above-mentioned configuration, the photographing apparatus 1G is attached in the dark room 91, and the LEDs in the illuminating devices 92 are set to be lit-on. Then, the patient 59 serving as the subject enters the dark room 91.

The LEDs of the illuminating devices 92 are lit-on, a desired portion of the patient 59 is photographed, and the desired spectroscopic image data is captured. The LEDs of the illuminating devices 92 are sequentially lit-on at the light-on timings of the LEDs 6X built in the photographing apparatus 1G, the light-on timings are lit-on in the light-emitting mode of the photographing apparatus 1G.

In the image processing system according to the eleventh embodiment, the color is accurately measured with no influence of ambient light and the color is reproduced at high fidelity level, even when the subject size is large. The dark room 91 may be a compact device having the space for arranging the attaching unit having the connector unit 93 of the photographing apparatus 1G and the illuminating devices 92. The inexpensive image processing system is obtained to photograph the subject with the large size.

By applying the photographing optical system 7 with a wide angle in the photographing apparatus 1G, the photographing range is wide and the large subject, e.g., large material such as a vehicle can be photographed.

Figure 62:
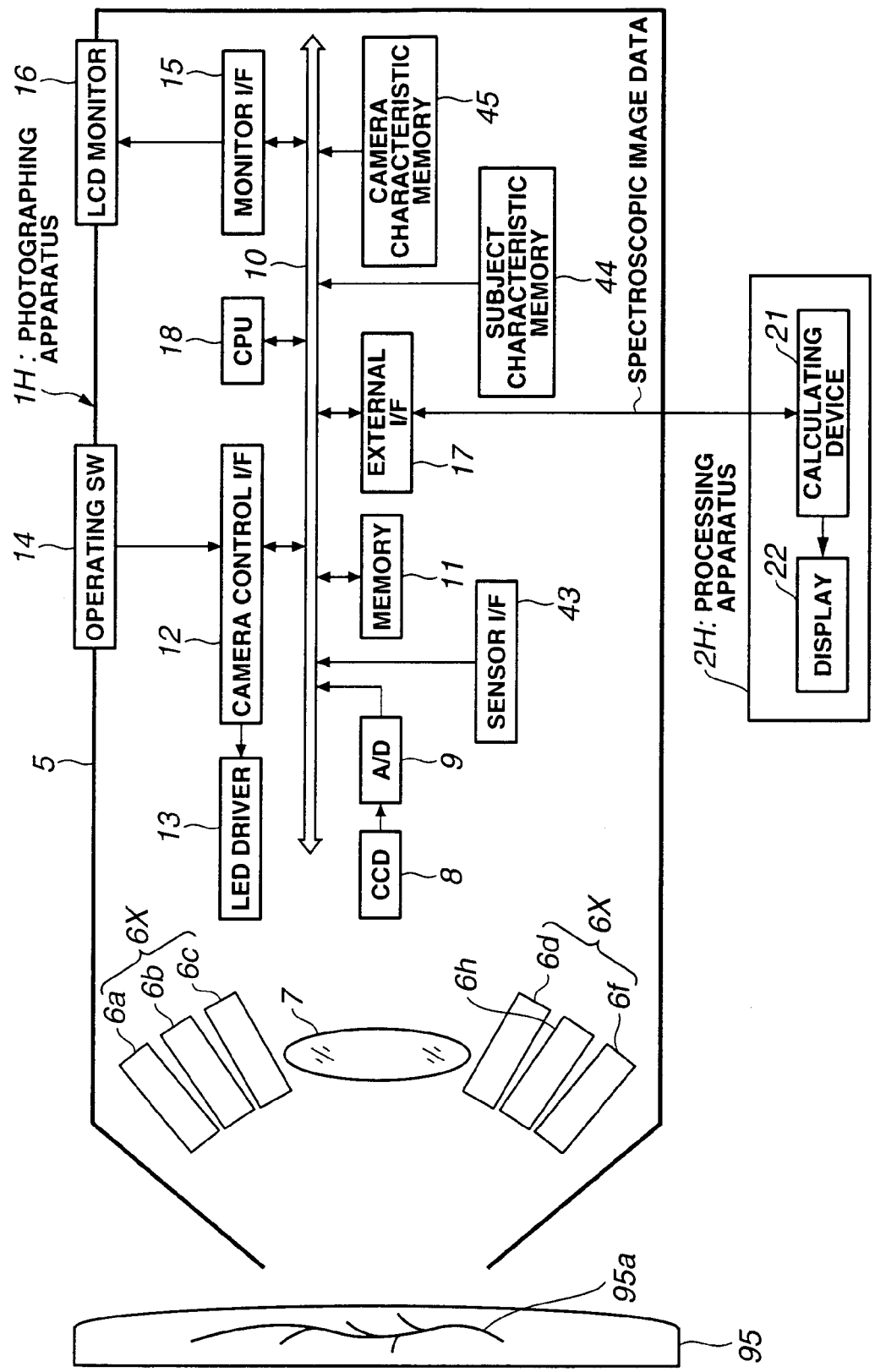
FIG. 62 is a block diagram showing the configuration of an image processing system according to a twelfth embodiment of the present invention.

Next, a description is given of an image processing system according to a twelfth embodiment of the present invention with reference to the block diagram shown in FIG. 62.

The image processing system according to the twelfth embodiment comprises: a photographing apparatus 1H serving as an image capturing unit; and a processing apparatus 2H serving as an image processing unit which obtains the color reproducing image data at high fidelity level from the spectroscopic image signal of the subject photographed by the photographing apparatus 1H and further determines the subject state based on the image data.

Referring to FIG. 62, the photographing apparatus 1H has the same configuration as that of the photographing apparatus 1 (refer to FIGS. 1, 17, 21, and 37) in the image processing system according to the first to fourth embodiments. Further, the photographing apparatus 1H comprises, serving as the illuminating light sources, the plurality of LEDs 6X serving as the light sources of the visible light and a plurality of LEDs 6h serving as near infrared light sources with the center wavelength 780 to 900 nm around the image pick-up optical system 7. The same components in the photographing apparatus 1H as those in the photographing apparatus 1 are designated by the same reference numerals.

The processing apparatus 2H has the same configuration and functions as those of the processing apparatus 2 in the image processing system according to the first embodiment, and may be a personal computer.

In the photographing apparatus 1H, when the LEDs 6X serving as the light sources of the visible light are lit-on in a predetermined light-emitting mode, the spectroscopic image data is captured by the visible light. Further, when the LEDs 6h serving as the light sources of the near infrared light are lit-on and the body surface of a patient 95 as the subject is irradiated, the spectroscopic image data is captured by the near infrared light.

In the photographing operation using the infrared light, the photographing apparatus 1H is set to a near infrared light photographing mode and the LEDs 6h are continuously lit-on. In this state, image data of the body surface of the patient 95 is captured with 30 frames per sec, and is then displayed. The captured image is displayed, as a monochrome image, on the LCD monitor 16 and the display 22 in the processing apparatus 2H.

As compared with the visible light, the near infrared light with the center wavelength 780 to 900 nm of the LEDs 6h reaches the deep portion under the body surface and therefore the state of a blood vessel 95a under the skin is photographed. In a blood flow observing mode, the state of the blood flow of the blood vessel 95a under the skin is observed on the display 22 by using the moving image data with 30 frames per sec. The state of the blood flow can be directly observed on the LCD monitor 16 of the photographing apparatus with the monochrome image.

In the image processing system according to the twelfth embodiment, the determination of the blood flow state can be automatically executed. The photographing person presses the operating switch 14 in the photographing apparatus 1H, thereby lighting-on the LEDs 6h for a predetermined time period. The photographed moving image data using the near infrared light is transferred to the processing apparatus 2H. In the processing apparatus 2H, the blood flow state is determined by calculating the moving image data.

By the calculation of the moving image of the blood flow state in addition to the determination of the blood flow state, the image processing system according to the twelfth embodiment can obtain the pulse rate and the heart rate.

Figure 63:
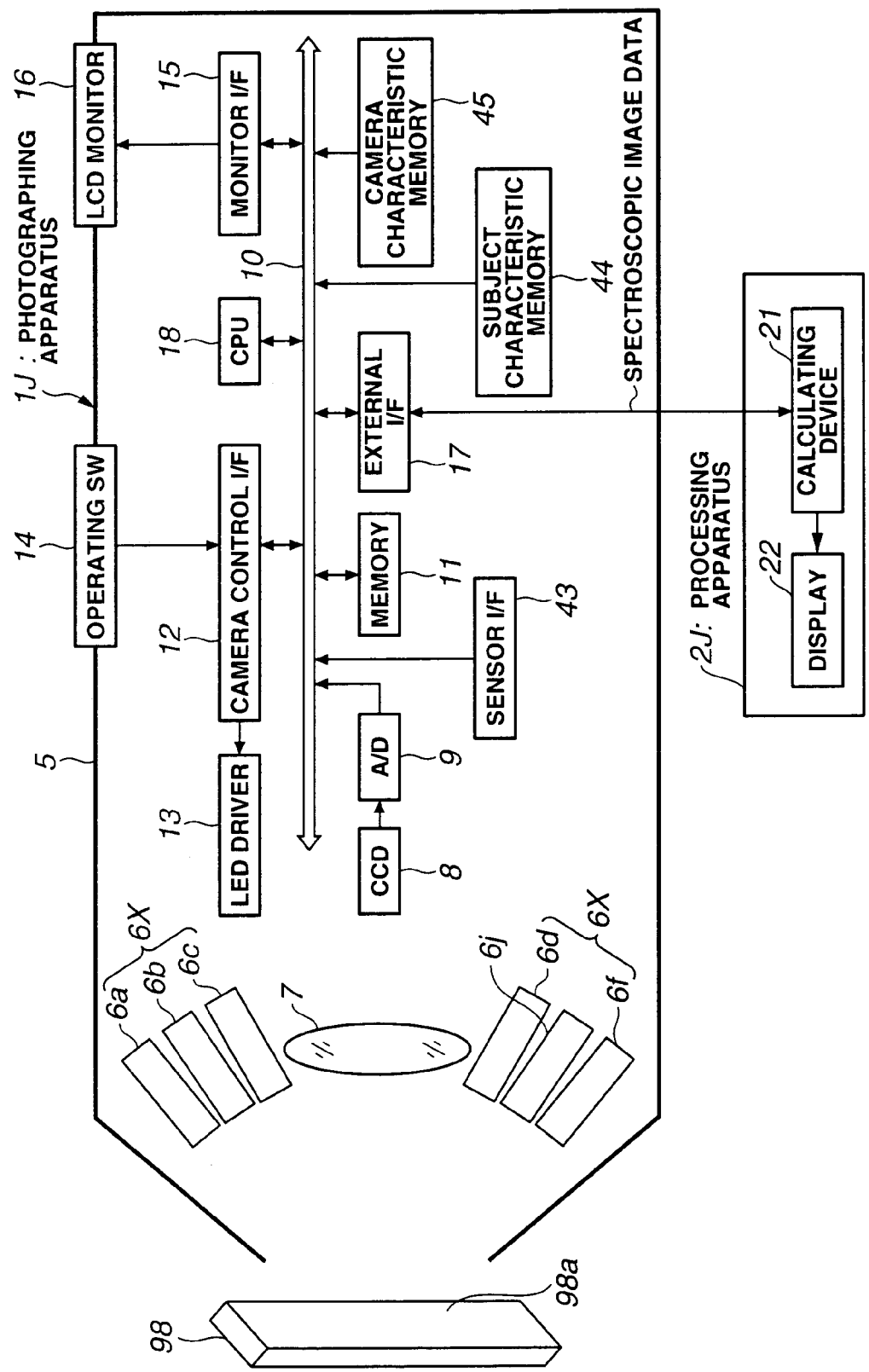
FIG. 63 is a block diagram showing the configuration of an image processing system according to a thirteenth embodiment of the present invention.

Next, a description is given of an image processing system according to a thirteenth embodiment of the present invention with reference to the block diagram shown in FIG. 63.

The image processing system according to the thirteenth embodiment comprises: a photographing apparatus 1J serving as an image capturing unit; and a processing apparatus 2J serving as an image processing unit which obtains the color reproducing image data at high fidelity level from the spectroscopic image signal of the subject photographed by the photographing apparatus 1J and further determines the surface state of the subject based on the image data.

Referring to FIG. 63, the photographing apparatus 1J has the same configuration as that of the photographing apparatus 1 (refer to FIGS. 1, 17, 21, and 37) in the image processing system according to the first to fourth embodiments. Further, the photographing apparatus 1J comprises, serving as the illuminating light sources, the plurality of LEDs 6X serving as the light sources of the visible light and a plurality of LEDs 6j serving ultraviolet light sources with the center wavelength 300 nm to 380 nm around the image pick-up optical system 7. The same components in the photographing apparatus 1J as those in the photographing apparatus 1 are designated by the same reference numerals.

The processing apparatus 2J has the same configuration and functions as those of the processing apparatus 2 in the image processing system according to the first embodiment.

In the photographing apparatus 1J, when the LEDs 6X serving as the light sources of the visible light are lit-on in a predetermined light-emitting mode, the spectroscopic image data is captured by the visible light. Further, when the LEDs 6j serving as the light sources of the ultraviolet light are lit-on and a surface 98a of an examined member 98 as the subject is irradiated, the spectroscopic image data is captured by the ultraviolet light.

In the photographing operation using the ultraviolet light, the photographing apparatus 1J is set to an ultraviolet photographing mode and the LEDs 6j are lit-on. In this state, the image data on the surface 98a of the examined member 98 is captured and is displayed. The captured image is displayed, as the monochrome image, on the LCD monitor 16 and the display 22 of the processing apparatus 2J.

As compared with the visible light, the ultraviolet light with the center wavelength 300 nm to 380 nm of the LEDs 6j is scattered and reflected at the shallow position of the subject surface layer. Therefore, the state of the subject surface such as the fine scratch on the surface is observed with the photographed image.

A modified photographing apparatus may be configured by combining the photographing apparatus 1H and 1J applied in the twelfth and thirteenth embodiments. The photographing apparatus according to the modification comprises, in addition to the LEDs 6X of the visible light serving as the light sources, the LEDs 6h serving as the light sources of the near infrared light, and the LEDs 6j serving as the light sources of the ultraviolet light, around the image pick-up optical system 7.

The photographing apparatus according to the modification enables the single photographing apparatus to capture the spectroscopic image data of various subjects, by performing the observation of the patient blood-flow and the surface-scratch examination of the sensed member and the like.

Figure 64:
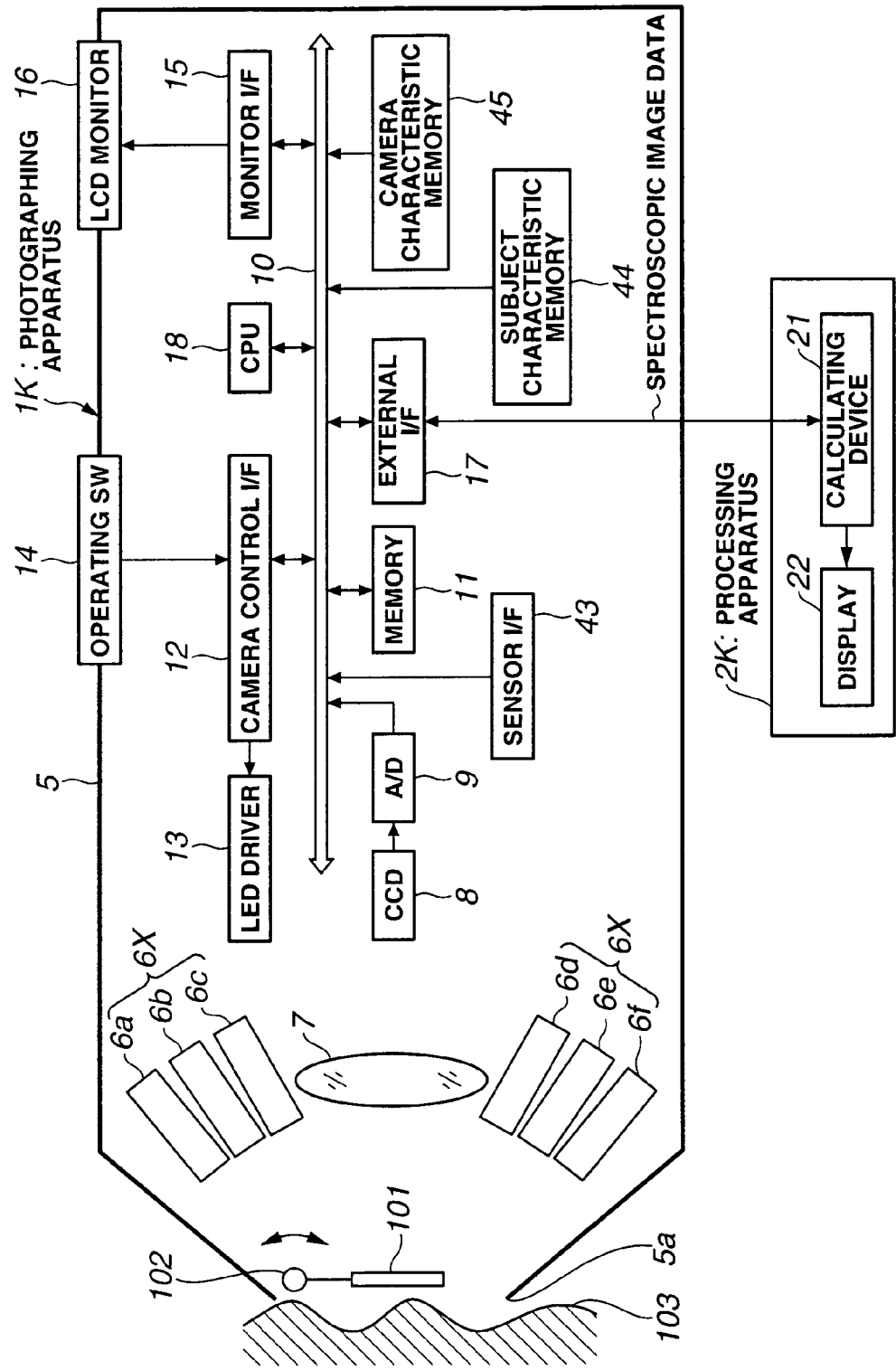
FIG. 64 is a block diagram showing the configuration of an image processing system according to a fourteenth embodiment of the present invention.

Next, a description is given of an image processing system according to a fourteenth embodiment of the present invention with reference to the block diagram shown in FIG. 64.

The image processing system according to the fourteenth embodiment comprises a photographing apparatus 1K serving as an image capturing unit and a processing apparatus 2K serving as an image processing unit which obtains the color reproducing image data at high fidelity level from the spectroscopic image signal of the subject photographed by the photographing apparatus 1K.

Referring to FIG. 64, the photographing apparatus 1K has the same configuration as that of the photographing apparatus 1 (refer to FIGS. 1, 17, 21, and 37) in the image processing system according to the first to fourth embodiments. Further, the photographing apparatus 1K comprises a color chip 101 having the arrangement of calibration standard colors, the color chip 101 being freely rotatably supported by a supporting shaft 102 at the projecting port 5a of the casing 5.

The same components in the photographing apparatus 1K as those in the photographing apparatus 1 are designated by the same reference numerals.

The processing apparatus 2K has the same configuration and functions as those of the processing apparatus 2 in the image processing system according to the first embodiment.

The photographing apparatus 1K according to the fourteenth embodiment does not need the storage and management of the color chip, which is conventionally troublesome, and includes the color chip 101 in the casing 5 to prevent the dirt of the color chip and the deterioration due to the ambient light. When the color chip 101 is not used, it is evacuated from the projecting port 5a of the image pick-up optical system and is accommodated in the casing 5. In the accommodating state, the color chip 101 is evacuated out of the illuminating optical paths of the LEDs 6X, and does not become the obstacle of the illuminating light to a subject 103. Only in the calibration, the color chip 101 is rotated to the position of the projecting port 5a of the image pick-up optical system 7 as shown in FIG. 64. In this state, the image data of the color chip 101 is captured via the CCD 8 and the spectroscopic image data for color calibration is obtained.

In the photographing apparatus 1K according to the fourteenth embodiment, the storage and management of the color chip 101 are not necessary, the dirt is not easily caused because of no manual operation of the hands, the color is not deteriorated because of no exposure to the ambient light, and the color is always accurately calibrated.

In the photographing apparatus 1K according to the fourteenth embodiment, the color chip 101 is rotatably supported to the casing 5. Unlike this, the color chip may be adhered to the inner surface of a lens cap (not shown) attached/detached to/from the projecting port 5a of the casing 5. In this case, the calibration is performed while the lens cap is attached.

Figure 65:
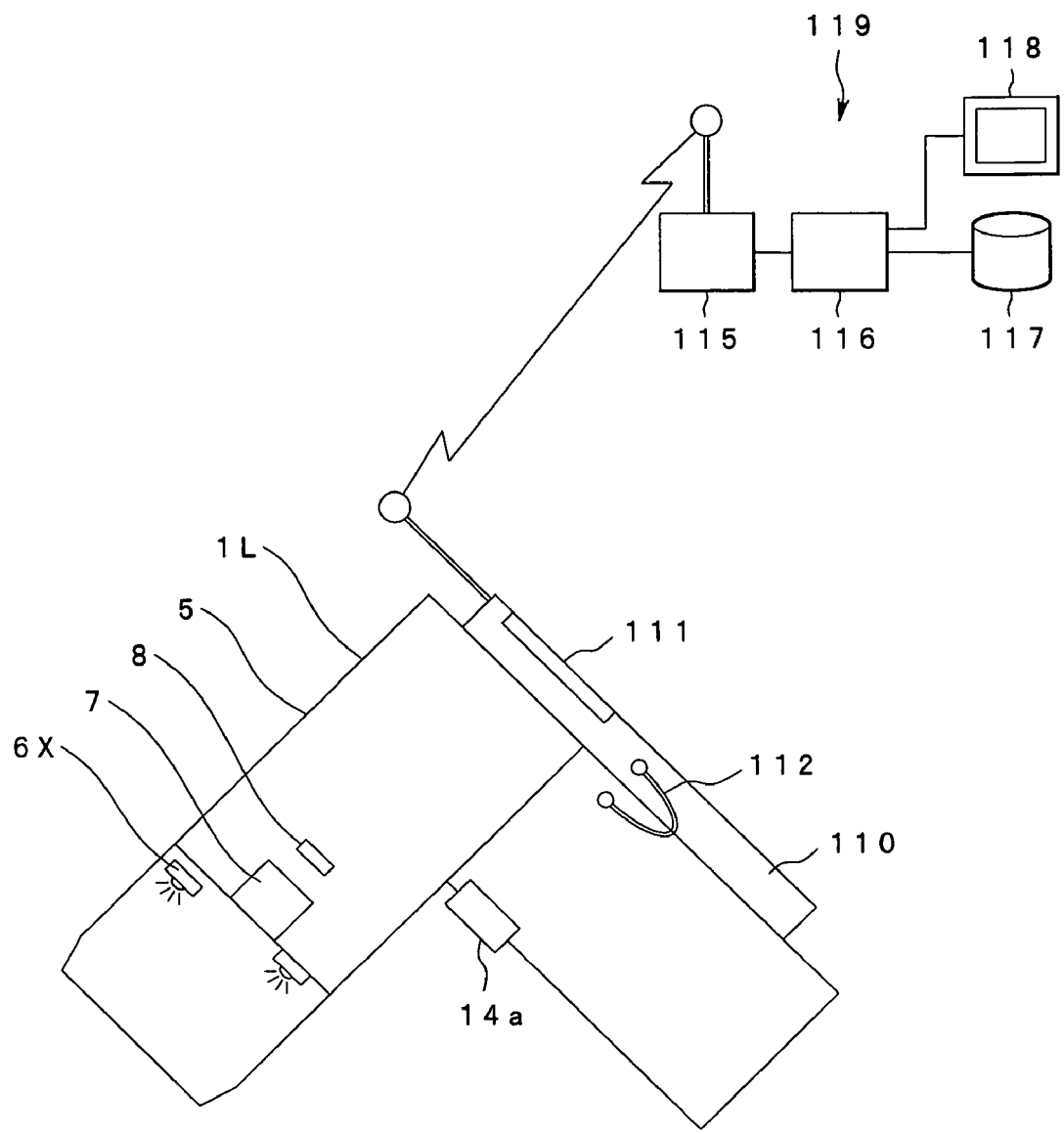
FIG. 65 is a block diagram showing the configuration of an image processing system according to a fifteenth embodiment of the present invention.

Next, a description is given of an image processing system according to a fifteenth embodiment of the present invention with reference to the system block diagram shown in FIG. 65.

The image processing system according to the fifteenth embodiment comprises: a photographing apparatus 1L serving as an image capturing unit; a mobile telephone 110 which is connected to the photographing apparatus 1L via a cable 112; and an in-hospital processing system 119 which can be communicated with the mobile telephone 110.

The in-hospital processing system 119 comprises an in-hospital communication device 115, a processing apparatus 116, a database 117, and a monitor 118.

Referring to FIG. 65, the photographing apparatus 1K has the same configuration as that of the photographing apparatus 1 (refer to FIGS. 1, 17, 21, and 37) in the image processing system according to the first to fourth embodiments. The same components in the photographing apparatus 1K as those in the photographing apparatus 1 are designated by the same reference numerals.

The mobile telephone 110 sends the spectroscopic image data of the affected part of the patient, which is captured by the photographing apparatus 1L, to the in-hospital communication device 115 of the in-hospital processing system 119 via a public communication line. The mobile telephone 110 comprises an LCD monitor 111.

The processing apparatus 116 of the in-hospital processing system 119 is an image processing unit which obtains the color reproducing image data at high fidelity level by using the spectroscopic image signal of the affected part received via the in-hospital communication device 115, and has the same configuration as that of the processing apparatus 2 according to the first embodiment.

Hereinbelow, a description is given of the operation for processing the spectroscopic image data in the image processing system according to the fifteenth embodiment by dividing processing steps into those of the processing of the mobile telephone 110, those of the processing of the in-hospital processing system 119, and those of the processing of the photographing apparatus 1L.

The processing steps of the mobile telephone 110 will be described. First, the mobile telephone 110 is connected to the photographing apparatus 1L. Then, the ID of the photographing apparatus 1L is checked. If the ID of the photographing apparatus 1L is incorrect, an error message is outputted. If the mobile telephone 110 matches the photographing apparatus 1L, the mobile telephone 110 is set to a photographing mode, the monitor 111 of the mobile telephone functions as a monitor of the photographing apparatus 1L, and an operating button of the mobile telephone is set so as to function as an operating switch of the photographing apparatus 1L.

A connecting request is outputted, via the public line, to the in-hospital processing system 119 which has already been set. The identification of the in-hospital processing system 119 ends and then the connection is established.

The monitoring image from the photographing apparatus 1L is displayed on the monitor 111 of the mobile telephone 110, and the photographing preparation is completed.

The user presses the photographing button 14a of the photographing apparatus 1L and then the output of photographed image data from the photographing apparatus 1L is waited. The photographed image data is outputted and then the image data is displayed on the monitor 111. The image data is sent to the in-hospital processing system 119 and the user operation is waited.

The user operation requests the search for the image database of the in-hospital processing system 119. Then, the database 117 of the in-hospital processing system 119 is accessed, information on the database 117 is obtained, and the information is displayed on the monitor 118.

Further, the user operation requests the search for the database 117. The search result from the database is received and is displayed on the monitor 111.

Next, the processing steps on the in-hospital processing system 119 will be described. First, a connecting request from the mobile telephone 110 is received, and the ID of the mobile telephone is checked. If the ID of the mobile telephone is incorrect, an error message is outputted and the connection is disconnected. Further, the ID of the photographing apparatus 1L is checked. If the ID of the photographing apparatus 1L is incorrect, an error message is outputted and the connection is discontinued.

Subsequently, ID information is requested and the ID information inputted by the user is checked. If the ID information is incorrect, an error message is outputted and the connection is discontinued. If the ID information is correct, the connection is established and the sending operation from the mobile telephone 110 is waited.

The photographing apparatus 1L photographs the image and then the image data from the mobile telephone 110 is received.

The received image data is recorded to the database 117 together with the ID of the mobile telephone, the ID of the photographing apparatus, and the ID information of the user. The sending operation from the mobile telephone 110 is waited.

A search request to the database 117 from the mobile telephone 110 is received and then the data is searched in the database 117. The search result is sent to the mobile telephone 110 and the sending operation from the mobile telephone 110 is waited.

Next, the processing steps of the photographing apparatus 1L will be described. The mobile telephone 110 is connected and the ID of the mobile telephone 110 is checked.

The image data from the photographing apparatus 1L enters a photographing state when the image data as live image data is sent to the mobile telephone 110. The operation of the photographing button 14a or photographing request from the mobile telephone 110 is waited.

The user executes the photographing operation, thereby the LEDs 6X serving as the light source units of the photographing apparatus 1L are lit on according to a predetermined sequence. Then, the photographing operation is executed, and the obtained photographed image data is sent to the mobile telephone 110.

With the configuration of the image processing system according to the fifteenth embodiment, the liquid crystal monitor does not need to be arranged to the photographing apparatus 1L, and the photographing apparatus 1L is constructed inexpensive. Further, the cable is not in the connection to the in-hospital processing system 119 and therefore the degree of handling freedom is high in the photographing operation. Since the public line is used as a communication line, the range of using place is wide. The operating button of the mobile telephone 110 is used and therefore more complicated character information such as the patient name or condition is inputted.

Further, voice data may be inputted together with the image data by using a microphone of the mobile telephone 110. In this case, information such as a comment using voice data can be inputted. Further, the operation can be performed by voice. Thus, the convenience is improved.

The mobile telephone 110 may be a PHS used in the hospital or a terminal device of LAN or a PDA device.

Figure 66:
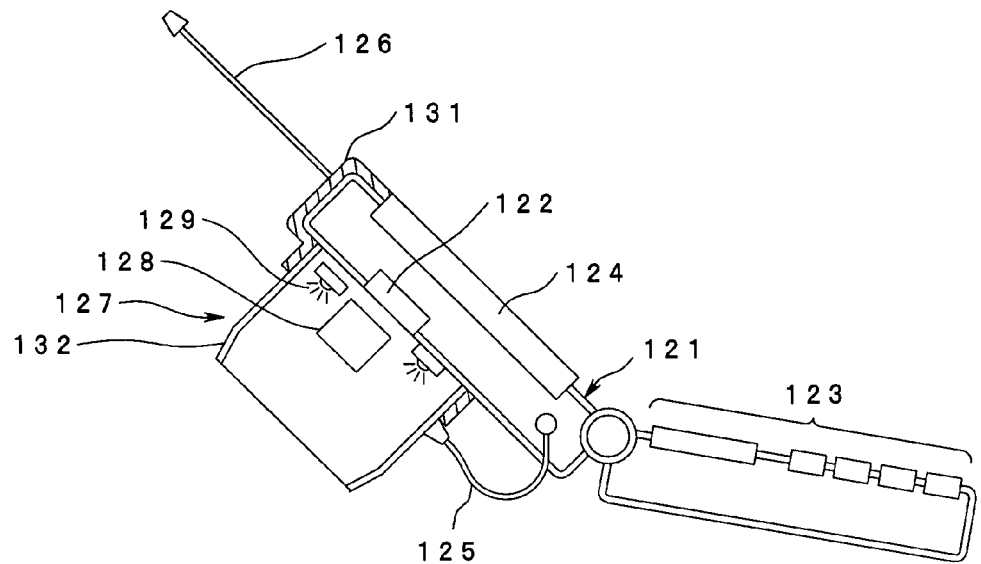
FIG. 66 is a block diagram showing the configuration of an image processing system according to a sixteenth embodiment of the present invention.

Next, a description is given of an image processing system according to a sixteenth embodiment of the present invention with reference to the block diagram in FIG. 66 showing the configuration of an image capturing unit in the image processing system.

Referring to FIG. 66, the image processing system according to the sixteenth embodiment comprises: a mobile telephone with camera 121 to which an LED illuminating unit 127 serving as an image capturing unit is attached; and an in-hospital processing system 119 which can communicate with the mobile telephone 121.

The in-hospital processing system 119 has the same system as that shown in FIG. 65 according to the fifteenth embodiment, and comprises an in-hospital communication device 115, a processing apparatus 116, the database 117, and the monitor 118.

When the LED illuminating unit 127 is attached to the mobile telephone with camera 121, the mobile telephone with camera 121 has the same photographing processing function as that of the photographing processing unit of the photographing apparatus 1 (refer to FIG. 1) in the image processing system according to the first embodiment. That is, the mobile telephone with camera 121 comprises a camera lens 122 serving as a photographing optical system, an LCD monitor 124, an operating switch 123, an antenna 126, and a connector unit. Further, the mobile telephone with camera 121 contains a CCD, an A/D converting circuit, an image data memory, a camera control I/F, a data receiving/transmitting circuit, a monitor I/F, an external I/F, a CPU which controls the mobile telephone and the like.

The LED illuminating unit 127 attachable to the mobile telephone with camera 121 is fixed to a main body of the mobile telephone with camera 121 by using a unit fixing metal fitting 131. Further, in the state in which the LED illuminating unit 127 is attached, the LED illuminating unit 127 comprises a close-up lens 128 facing the camera lens 122, LEDs 129 arranged along the outer circumference of the close-up lens, a shading cylinder 132 externally arranged to the LEDs 129, and a connecting cable 125 connected to a connector unit of the mobile telephone with camera 121.

The LEDs 129 have different spectroscopic distribution characteristics, similarly to those of the LEDs 6X arranged to the photographing apparatus 1 according to the first embodiment, and comprise a plurality of sets of 6 types of LEDs similar to the LEDs 6a and 6b as the blue light sources with different wavelengths, the LEDs 6b and 6c as the green light sources with different wavelengths, and the LEDs 6e and 6f as the red light sources with different wavelengths.

Next, a description is given of the photographing operation using the image processing system with the above-mentioned configuration according to the sixteenth embodiment.

The LED illuminating unit 127 attached to the mobile telephone with camera 121 is directed to the body surface of the patient as the subject, and then the operating switch 123 is operated. Further, the LEDs 129 are lit-on in a predetermined light-emitting sequence in the selected light-emitting mode. Further, the CCD (not shown) arranged to the mobile telephone 121 captures the photographed image data of the body surface of the patient upon the light emission of the LEDs. The image data is temporarily stored in a memory in the mobile telephone 121.

After that, the spectroscopic image data is sent to the in-hospital processing system 119 from the antenna 126 via the public line by operating the operating switch 123. On the in-hospital processing system 119 side, the imaging processing is performed based on the spectroscopic image data and the color reproducing processing is executed with high accuracy.

The data reception and transmission between the mobile telephone 121 and the in-hospital processing system 119 is similar to that in the case according to the eleventh embodiment.

The image processing system according to the twelfth embodiment does not need any dedicated photographing apparatus. The attachment of the LED illuminating unit 127 to the conventional mobile telephone with the camera results in the function of the photographing apparatus in the image processing system, and an inexpensive system using the public line is provided.

The mobile telephone 121 may be another terminal device with the camera function, a LAN terminal device, or a PDA device.

Figure 67:
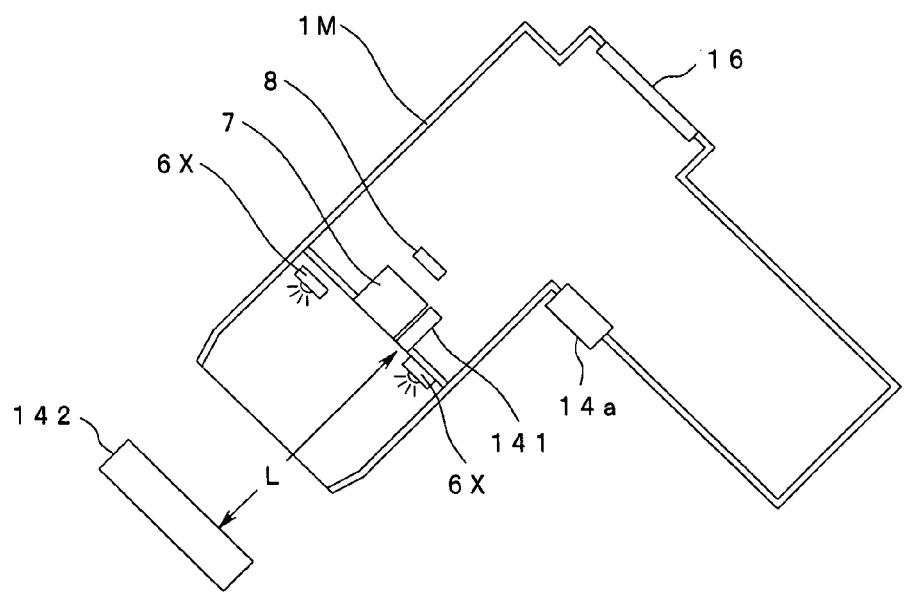
FIG. 67 is a block diagram showing the configuration of an image processing system according to a seventeenth embodiment of the present invention.

Next, a description is given of an image processing system according to a seventeenth embodiment of the present invention with reference to the block diagram in FIG. 67 showing the configuration of a photographing apparatus in the image processing system.

The image processing system according to the seventeenth embodiment comprises: a photographing apparatus 1M serving as an image capturing unit; and a processing apparatus (not shown) serving as an image processing unit which obtains the color reproducing image data at high fidelity level from the spectroscopic image signal of the subject photographed by the photographing apparatus 1M.

Referring to FIG. 67, the photographing apparatus 1M has the same configuration as that of the photographing apparatus 1 (refer to FIGS. 1, 17, 21, and 37) in the image processing system according to the first to fourth embodiments. Further, the photographing apparatus 1M comprises a distance measuring sensor 141, serving as distance measuring means, which measures a photographing distance L serving as an apart distance between the photographing apparatus 1M and a subject 142. The same components in the photographing apparatus 1M as those in the photographing apparatus 1 are designated by the same reference numerals.

The processing apparatus according to the seventeenth embodiment has the same configuration and functions as those of the processing apparatus 2 in the image processing system according to the first embodiment.

The photographing operation in the image processing system according to the seventeenth embodiment is performed by the following processing steps.

First, the user sets the photographing apparatus 1M to the subject 142 serving the patient body, measures the photographing distance by using the distance measuring sensor 141, and registers the measuring result. The difference from the target photographing distance is displayed on the LCD monitor 16 with a reference symbol. The user moves the photographing apparatus 1M while viewing the display on the LCD monitor 16. When the photographing distance matches the target one, such a fact is displayed on the LCD monitor 16. The photographing apparatus 1M waits for the photographing operation. The user operates the photographing button 14a and then the photographing operation starts.

In the image processing system according to the seventeenth embodiment, when the distance to the subject is determined by using the function for measuring the distance to the subject so as to photograph the same portion of the subject 142 serving as the patient body, the image size is the same as that compared with the previously-photographed image data, and the comparison is excessively easy.

Next, a description is given of the photographing apparatus in the image processing system according to a modification of the seventeenth embodiment.

The photographing operation in the photographing apparatus 1M according to the modification is executed by the following processing steps. That is, the user designates the previously-photographed image data, desired information on the photographing distance is obtained from the designated image data, and the obtained information is displayed on the LCD monitor 16.

The user obtains with the photographing apparatus 1M, the information on the actual photographing distance upon photographing the subject by determining the approximate distance with eye measurement, and a magnification correcting coefficient is calculated based on the actual photographing distance and the desired photographing distance. The LCD monitor 16 displays the image, of the same size with the previously-photographed image after correcting the magnification of the image that is actually photographed based on the calculated magnification correcting coefficient.

By roughly setting the distance to the subject 142 with the function of the photographing apparatus 1M according to the modification, the image data with the same magnification as that of the previous image is observed.

Figure 68:
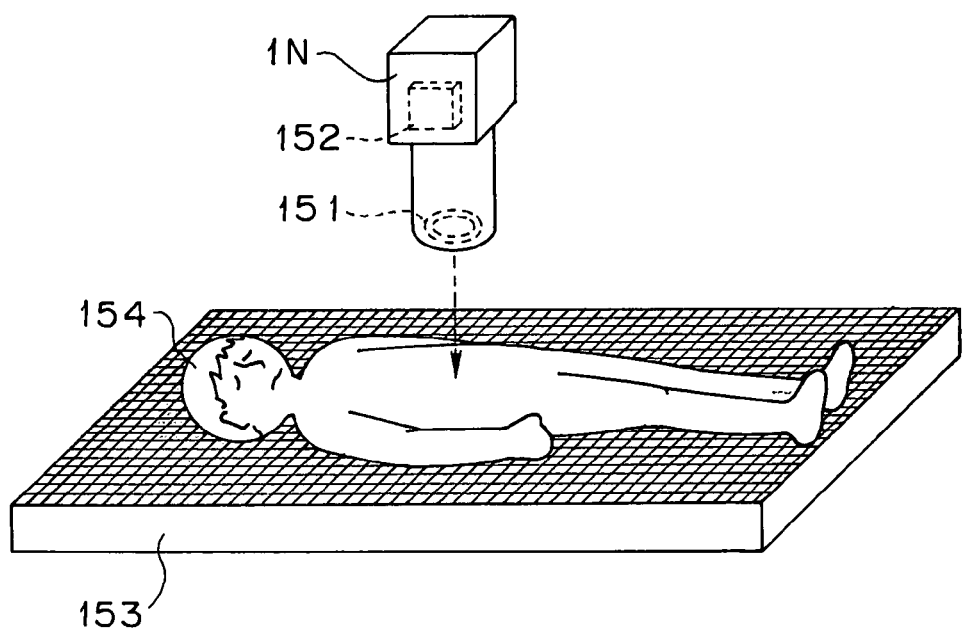
FIG. 68 is a block diagram showing the configuration of an image processing system according to an eighteenth embodiment of the present invention.

Next, a description is given of an image processing system according to an eighteenth embodiment of the present invention with reference to the diagram indicating a diagnostic state generated by using the system shown in FIG. 68.

The image processing system according to the eighteenth embodiment comprises: a photographing apparatus 1N serving as an image capturing unit; a diagnostic bed with digitizer 153, and a processing apparatus (not shown) serving as an image processing unit which obtains the color reproducing image data at high fidelity level from the spectroscopic image signal of the subject photographed by the photographing apparatus 1N.

Referring to FIG. 68, the photographing apparatus 1N has the same configuration as that of the photographing apparatus 1 (refer to FIGS. 1, 17, 21, and 37) in the image processing system according to the first to fourth embodiments. Further, the photographing apparatus 1N contains a position sensing coil 151, serving as subject portion sensing means which senses the coordinates of the photographing apparatus 1N at the tip of a barrel of the photographing apparatus 1N; and an angle sensor 152 which senses the position of the photographing apparatus 1N using the gravity or the like.

The same components in the photographing apparatus 1N as those in the photographing apparatus 1 are designated by the same reference numerals.

The processing apparatus according to the eighteenth embodiment has the same configuration and functions as those of the processing apparatus 2 in the image processing system according to the first embodiment.

The photographing apparatus 1N according to the eighteenth embodiment is assumed to be used for the diagnosis in a clinic or the like. A digitizer device for generating the magnetic field from a plurality of positions is attached to the diagnostic bed with digitizer 153, and which senses the position of the sensing coil 151 of the photographing apparatus 1N and so the position of the photographing apparatus 1N. Further, the angle sensor 152 of the photographing apparatus 1N senses the direction of the photographing apparatus 1N with respect to the horizontal direction.

In the photographing operation using the photographing apparatus 1N, a patient 154 of the subject for diagnosis is laid at a predetermined position of the diagnostic bed with digitizer 153. In this state, the photographing apparatus 1N photographs the image, thereby sensing the relative positional coordinates between the patient 154 and the photographing apparatus 1N in the photographing operation and the inclination of the photographing apparatus 1N. The sensed data is recorded together with the image data. The photographed portion of the patient is automatically recorded based on the sensed data. Therefore, the photographed position of the affected part and the photographed direction are confirmed every captured image data. It is possible to prevent the deviation in photographed portion and the change in photographing direction. Therefore, the correct diagnosis is executed.

Figure 69:
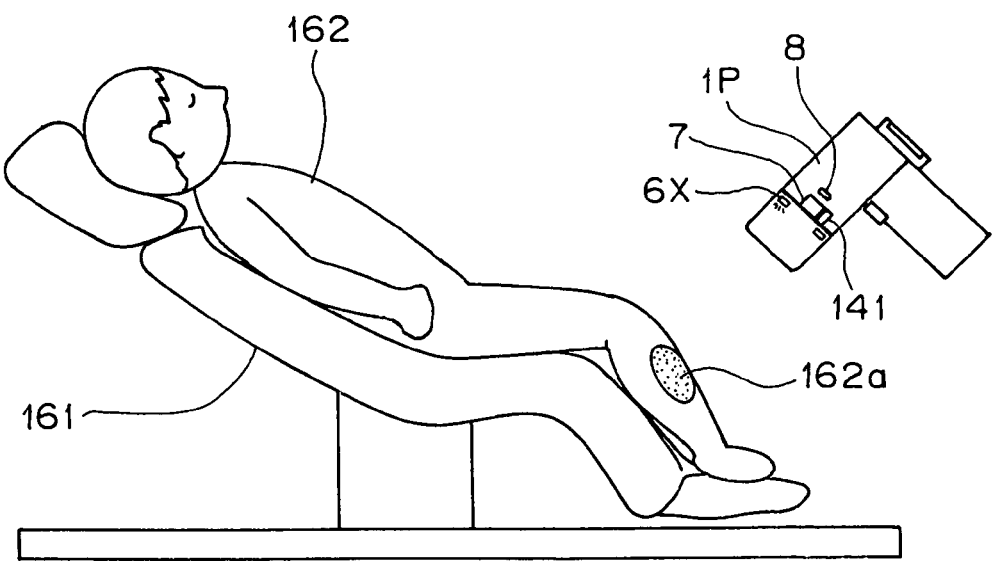
FIG. 69 is a block diagram showing the configuration of an image processing system according to a nineteenth embodiment of the present invention.

Next, a description is given of an image processing system according to a nineteenth embodiment of the present invention with reference to the diagram indicating a diagnostic state generated by using the system shown in FIG. 69.

The image processing system according to the nineteenth embodiment comprises: a photographing apparatus 1P serving as an image capturing unit; a processing apparatus (not shown) serving as an image processing unit which obtains the color reproducing image data at high fidelity level from the spectroscopic image signal of the subject photographed by the photographing apparatus 1P; and a diagnostic chair 161.

The photographing apparatus 1P has the same configuration as that of the photographing apparatus 1 (refer to FIGS. 1, 17, 21, and 37) in the image processing system according to the first to fourth embodiments. Further, the photographing apparatus 1P contains an optical pattern projecting device (not shown), serving as subject portion detecting means, the optical pattern projecting device projects a specific optical pattern to the subject. However, the optical pattern projecting device may be not contained in the photographing apparatus 1P and may be fixed.

The same components in the photographing apparatus 1P as those in the photographing apparatus 1 are designated by the same reference numerals.

The processing apparatus according to the nineteenth embodiment has the same configuration and functions as those of the processing apparatus 2 in the image processing system according to the first embodiment.

According to the eighteenth embodiment, the digitizer for specifying the photographing position is applied. However, according to the nineteenth embodiment, the photographing portion of the spectroscopic image data is specified by referring to the image photographed in a state in which the specific optical pattern is projected to the patient.

That is, in the photographing operation using the photographing apparatus 1P in the image processing system according to the nineteenth embodiment, referring to FIG. 69, a patient 162 serving as the subject sits on the diagnostic bed 161. Then, the photographing apparatus 1P is set so that an affected part 162a of the patient 162 can be photographed. Then, the specific optical pattern is projected to the patient 162 from the optical pattern projecting device. The periphery of the affected part 162a in the state that optical pattern is being projected is once photographed in the monitoring image capturing mode. The spectroscopic image data is captured by the photographing operation with the illuminating light of the LEDs 6X in the spectroscopic image capturing mode while the photographing apparatus 1P is being kept from moving.

In the image processing system according to the nineteenth embodiment, it is possible to accurately specify the photographed portion of which the spectroscopic image data is captured using the projected image of the optical pattern.

According to one modification, a photographing apparatus in the image processing system is proposed as follows.

That is, the photographing apparatus according to the modification of the nineteenth embodiment comprises: a temperature sensor for measuring the body temperature at the tip of the device main body; a pulse sensor for sending the pulses;

and a microphone (sensor) namely, an auscultation function, for sensing Korotkoff sounds upon measuring the blood pressure, breath sounds and heart sounds at the chest region, and abdominal noises at the abdominal region. These sensors capture data on the body temperature, pulses, and heart beats in addition to the spectroscopic image data of the subject. The data on the body temperature, pulses, and heart beats upon photographing operation of the affected part of the patient is simultaneously stored in the memory with a correlation with the spectroscopic image data. Thus, the data on the body temperature, pulses, and heart beats, which is measured every day by the sensors in the photographing apparatus can be sent to the medical service providers via the public line and therefore the home health management is finely realized.

In the image processing system according to the embodiments, the photographing apparatus serving as the image capturing unit and the processing apparatus serving as the image processing unit are separately arranged. However, the photographing apparatus and the processing apparatus may be integrated, thereby being configured as a single portable device. In this case, the image processing is simultaneously performed while photographing so that the image processing system is easily handled depending on the using purpose.

The present invention is not limited to the above embodiments and can be variously modified without departing the spirit of the present invention.

INDUSTRIAL APPLICABILITY

In the image processing system according to the present invention, as mentioned above, the image processing system with the compact and portable size and light weight reproduces the colors at high fidelity level and is preferable as an information communication device.

The invention claimed is:

1. An image processing system comprising:
   an image capturing unit; and
   an image processing unit,
   the image capturing unit comprising:
   an illuminating light source including a plurality of light-emitting devices which respectively emit illumination lights having a plurality of different characteristics of spectroscopic distributions;
   an image pick-up optical system which forms an image of a subject illuminated by the illuminating light source;
   an image pick-up device which picks up the subject image formed by the image pick-up optical system and obtains a subject signal; and
   a control unit which controls light emission by the plurality of light-emitting devices and image pick-up by the image pick-up device and which switches the image capturing unit between a spectroscopic image capturing mode in which it obtains a still image of a subject spectroscopic image and a moving image capturing mode in which it obtains a moving image thereof;
   wherein, in the spectroscopic image capturing mode, the control unit controls the plurality of light-emitting devices to sequentially emit light according to the different characteristics of spectroscopic distributions by a plurality of times interlocking the light emission with an exposure timing of the image pick-up device thereby causing the image pick-up device to obtain a plurality of subject spectroscopic images; and
   wherein, in the moving image capturing mode, the control unit is arranged to cause light emission of a light-emitting device for a single specific primary color or cause light emission of light-emitting devices for a plurality of specific primary colors selected from the plurality of light-emitting devices, or cause sequential light emission of a group of R devices, a group of G devices, and a group of B devices selected from the plurality of light-emitting devices, group by group, and to cause the image pick-up device to obtain a moving image; and
   the image processing unit comprising:
   an image identification calculating unit which calculates grade data to be used to determine a grade of a color of the subject based on one or more of the subject spectroscopic images captured by the image capturing unit when operating in the spectroscopic image capturing mode.

2. The image processing system according to claim 1, wherein the grade data indicates a grade of a shading guide and wherein the subject is a tooth and; and
   wherein the image processing system compares the color of the tooth and the grade data.

3. The image processing system according to claim 1, wherein the image processing unit calculates a ceramic compounding ratio of a false tooth based on the grade data to obtain false tooth ceramic compounding ratio data.

4. The image processing system according to claim 3, further comprising a computer connected to the image processing unit through a network, wherein the image processing unit transfers the grade data and the false tooth ceramic compounding ratio data to the computer.

5. The image processing system according to claim 4, further comprising a ceramic compounding ratio calculation database connected to the computer, wherein the computer searches for the ceramic compounding ratio from the ceramic compounding ratio calculation database based on the grade data and the false tooth ceramic compounding ratio data.

6. The image processing system according to claim 1, further comprising a display unit connected to the image processing unit, wherein the image identification calculating unit calculates the grade data before and after treatment of the subject, and the display unit displays the grade data calculated before and after the treatment of the subject.

7. The image processing system according to claim 1, wherein the image capturing unit further comprises an abutting portion formed in a cylindrical shape which abuts the subject.

8. The image processing system according to claim 7, wherein the abutting portion is configured to be detachably attached to the image capturing unit.

9. The image processing system according to claim 1, wherein the image capturing unit further comprises reflected light rejecting means for preventing the illuminating light source from being photographed with the subject.

10. The image processing system according to claim 1, wherein the image capturing unit further comprises an optical member which reduces the illuminating unhomogeneity between the illuminating light source and the subject.

11. The image processing system according to claim 1, wherein the plurality of illuminating light sources include at least one of: (i) a light source with a center wavelength of 780 to 900 nm, and (ii) a light source with a center wavelength of 300 to 380 nm.

12. The image processing system according to claim 1, wherein the image capturing unit and the image processing unit are integrally formed.

13. The image processing system according to claim 1, wherein the image capturing unit includes a color chip for calibration in the image processing unit.

14. The image processing system according to claim 1, wherein the image capturing unit comprises a portable terminal device having a photographing function, and wherein an illuminating light source unit having the plurality of illuminating light sources as one unit is attachable to the portable terminal device.

15. The image processing system according to claim 1, wherein the image processing unit comprises image filing software, and image data photographed upon operating the photographing operating unit is recorded in accordance with the image filing software.

16. The image processing system according to claim 1, wherein the image capturing unit further comprises subject portion sensing means for obtaining positional information of the subject.

17. The image processing system according to claim 1, wherein the image capturing unit further comprises distance measuring means for managing a size of the subject in the photographed image.

18. The image processing system according to claim 17, wherein the image capturing unit further comprises a monitor which displays the image of the subject, and wherein the image capturing unit controls the monitor to display a difference between a photographing distance measured by the distance measuring means and a target photographing distance.

19. The image processing system according to claim 17, wherein the image capturing unit further comprises a monitor which displays the image of the subject, and wherein the image capturing unit controls the monitor to display an indication that the photographing distance measured by the distance measuring means matches a target photographing distance.

20. The image processing system according to claim 17, wherein the image capturing unit further comprises a monitor which displays the image of the subject, and wherein the image capturing unit obtains information of a desired photographing distance from images previously picked up, calculates a magnification correcting coefficient based on information of an actual photographing distance measured by the distance measuring means and the desired photographing distance information, and controls the monitor to display the image of the subject with a magnification corrected based on the magnification correcting coefficient.

* * * * *